(12) United States Patent
Barron et al.

(10) Patent No.: US 11,639,897 B2
(45) Date of Patent: May 2, 2023

(54) CONTAMINATION LOAD SENSING DEVICE

(71) Applicant: Vyv, Inc., Latham, NY (US)

(72) Inventors: Robert Barron, Boulder, CO (US); Cori J. Winslow, Rensselaer, NY (US)

(73) Assignee: Vyv, Inc., Latham, NY (US)

( * ) Notice: Subject to any disclaimer, the term of this patent is extended or adjusted under 35 U.S.C. 154(b) by 0 days.

(21) Appl. No.: 16/833,082

(22) Filed: Mar. 27, 2020

(65) Prior Publication Data
US 2020/0309702 A1 Oct. 1, 2020

Related U.S. Application Data

(60) Provisional application No. 62/826,198, filed on Mar. 29, 2019.

(51) Int. Cl.
G01J 3/30 (2006.01)
G01N 21/64 (2006.01)
G01N 33/68 (2006.01)

(52) U.S. Cl.
CPC ..... *G01N 21/6486* (2013.01); *G01N 33/6839* (2013.01); *G01N 2021/6419* (2013.01); *G01N 2021/6421* (2013.01)

(58) Field of Classification Search
CPC .... G01N 21/6486; G01N 21/62; G01N 21/63; G01N 21/64; G01N 21/9036;
(Continued)

(56) References Cited

U.S. PATENT DOCUMENTS 1,493,820 A 5/1924 Miller et al.
2,622,409 A 12/1952 Stimkorb
(Continued)

FOREIGN PATENT DOCUMENTS

CN 201396611 Y 2/2010
CN 201423033 Y 3/2010
(Continued)

OTHER PUBLICATIONS

Schwartz A, Wang L, Early E, Gaigalas A, Zhang YZ, Marti GE, Vogt RF. Quantitating Fluorescence Intensity from Fluorophore: The Definition of MESF Assignment. J Res Natl Inst Stand Technol. Feb. 1, 2002;107(1):83-91. doi: 10.6028/jres.107.009. PMID: 27446720; PMCID: PMC4865278. (Year: 2002).*
(Continued)

*Primary Examiner* — Tarifur R Chowdhury
*Assistant Examiner* — Jonathon Cook
(74) *Attorney, Agent, or Firm* — Banner & Witcoff, Ltd.

(57) ABSTRACT

Systems and methods for bacterial load sensing devices are disclosed. An example contamination sensing device may comprise a body, a light emitter disposed on the body and configured to emit an excitation wavelength of light toward a surface, a sensor disposed on the body, configured to detect light, and directed toward the surface, and a filter adjuster configured to determine, based on the excitation wavelength of light, a filter configured to remove light outside of an emission wavelength range, wherein the emission wavelength range corresponds to wavelengths of light emitted by contamination upon exposure to the excitation wavelength of light, and adjustably move the filter in front of the sensor.

26 Claims, 22 Drawing Sheets

(58) Field of Classification Search
CPC ....... G01N 33/6839; G01N 2021/6419; G01N 2021/6421; G01J 3/0272; G01J 3/0294; G01J 3/2803; G01J 3/44; G01J 3/4406; G01J 3/443

See application file for complete search history.

(56) References Cited

U.S. PATENT DOCUMENTS

| | | | |
|---|---|---|---|
| 2,773,715 A | 12/1956 | Lindner | |
| 3,314,746 A | 4/1967 | Millar | |
| 3,670,193 A | 6/1972 | Thorington et al. | |
| 3,791,864 A | 2/1974 | Steingroever | |
| 3,926,556 A | 12/1975 | Boucher | |
| 3,992,646 A | 11/1976 | Corth | |
| 4,121,107 A | 10/1978 | Bachmann | |
| 4,461,977 A | 7/1984 | Pierpoint et al. | |
| 4,576,436 A | 3/1986 | Daniel | |
| 4,867,052 A | 9/1989 | Cipelletti | |
| 4,892,712 A | 1/1990 | Robertson et al. | |
| 4,910,942 A | 3/1990 | Dunn et al. | |
| 5,231,472 A | 7/1993 | Marcus et al. | |
| 5,489,827 A | 2/1996 | Xia | |
| 5,530,322 A | 6/1996 | Ference et al. | |
| 5,559,681 A | 9/1996 | Duarte | |
| 5,668,446 A | 9/1997 | Baker | |
| 5,721,471 A | 2/1998 | Begemann et al. | |
| 5,725,148 A | 3/1998 | Hartman | |
| 5,800,479 A | 9/1998 | Thiberg | |
| 5,901,564 A | 5/1999 | Comeau, II | |
| 5,915,279 A * | 6/1999 | Cantrall | G01N 33/365 73/800 |
| 5,962,989 A | 10/1999 | Baker | |
| 5,968,766 A * | 10/1999 | Powers | G01N 21/6486 435/283.1 |
| 6,031,958 A | 2/2000 | McGaffigan | |
| 6,166,496 A | 12/2000 | Lys et al. | |
| 6,183,500 B1 | 2/2001 | Kohler | |
| 6,242,752 B1 | 6/2001 | Soma et al. | |
| 6,246,169 B1 | 6/2001 | Pruvot | |
| 6,251,127 B1 | 6/2001 | Biel | |
| 6,379,022 B1 | 4/2002 | Amerson et al. | |
| 6,477,853 B1 | 11/2002 | Khorram | |
| 6,524,529 B1 | 2/2003 | Horton, III | |
| 6,551,346 B2 | 4/2003 | Crossley | |
| 6,554,439 B1 | 4/2003 | Teicher et al. | |
| 6,627,730 B1 | 9/2003 | Burnie | |
| 6,676,655 B2 | 1/2004 | McDaniel | |
| 6,791,259 B1 | 9/2004 | Stokes et al. | |
| 6,902,807 B1 | 6/2005 | Argoitia et al. | |
| 7,015,636 B2 | 3/2006 | Bolta | |
| 7,175,807 B1 | 2/2007 | Jones | |
| 7,190,126 B1 | 3/2007 | Paton | |
| 7,198,634 B2 | 4/2007 | Harth et al. | |
| 7,201,767 B2 | 4/2007 | Bhullar | |
| 7,213,941 B2 | 5/2007 | Sloan et al. | |
| 7,438,719 B2 | 10/2008 | Chung et al. | |
| 7,476,885 B2 | 1/2009 | Garcia et al. | |
| 7,503,675 B2 | 3/2009 | Demarest et al. | |
| 7,516,572 B2 | 4/2009 | Yang et al. | |
| 7,521,875 B2 | 4/2009 | Maxik | |
| 7,611,156 B2 | 11/2009 | Dunser | |
| 7,612,492 B2 | 11/2009 | Lestician | |
| 7,658,891 B1 | 2/2010 | Barnes | |
| 7,955,695 B2 | 6/2011 | Argoitia | |
| 8,035,320 B2 | 10/2011 | Sibert | |
| 8,214,084 B2 | 7/2012 | Ivey et al. | |
| 8,232,745 B2 | 7/2012 | Chemel et al. | |
| 8,357,914 B1 | 1/2013 | Caldwell | |
| 8,398,264 B2 | 3/2013 | Anderson et al. | |
| 8,467,052 B1 * | 6/2013 | Chao | G01N 21/65 356/301 |
| 8,476,844 B2 | 7/2013 | Hancock et al. | |
| 8,481,970 B2 | 7/2013 | Cooper et al. | |
| 8,506,612 B2 | 8/2013 | Ashdown | |
| 8,508,204 B2 | 8/2013 | Deurenberg et al. | |
| 8,761,565 B1 | 6/2014 | Coleman et al. | |
| 8,886,361 B1 | 11/2014 | Harmon et al. | |
| 8,895,940 B2 | 11/2014 | Moskowitz et al. | |
| 8,999,237 B2 | 4/2015 | Tumanov | |
| 9,024,276 B2 | 5/2015 | Pugh et al. | |
| 9,027,479 B2 | 5/2015 | Raksha et al. | |
| 9,028,084 B2 | 5/2015 | Maeng et al. | |
| 9,039,966 B2 | 5/2015 | Anderson et al. | |
| 9,046,227 B2 | 6/2015 | David et al. | |
| 9,078,306 B2 | 7/2015 | Mans et al. | |
| 9,119,240 B2 | 8/2015 | Nagazoe | |
| 9,173,276 B2 | 10/2015 | Van Der Veen et al. | |
| 9,257,059 B2 | 2/2016 | Raksha et al. | |
| 9,283,292 B2 | 3/2016 | Kretschmann | |
| 9,313,860 B2 | 4/2016 | Wingren | |
| 9,323,894 B2 | 4/2016 | Kiani | |
| 9,333,274 B2 | 5/2016 | Peterson et al. | |
| 9,368,695 B2 | 6/2016 | David et al. | |
| 9,410,664 B2 | 8/2016 | Krames et al. | |
| 9,420,671 B1 | 8/2016 | Sugimoto et al. | |
| 9,433,051 B2 | 8/2016 | Snijder et al. | |
| 9,439,271 B2 | 9/2016 | Ku et al. | |
| 9,439,989 B2 | 9/2016 | Lalicki et al. | |
| 9,492,576 B1 | 11/2016 | Cudak et al. | |
| 9,581,310 B2 | 2/2017 | Wu et al. | |
| 9,623,138 B2 | 4/2017 | Pagan et al. | |
| 9,625,137 B2 | 4/2017 | Li et al. | |
| 9,681,510 B2 | 6/2017 | van de Ven | |
| 10,732,037 B1 * | 8/2020 | Reid | G01J 3/0297 |
| 2002/0074559 A1 | 6/2002 | Dowling et al. | |
| 2002/0122743 A1 | 9/2002 | Huang | |
| 2003/0009158 A1 | 1/2003 | Perricone | |
| 2003/0019222 A1 | 1/2003 | Takahashi et al. | |
| 2003/0023284 A1 | 1/2003 | Gartstein et al. | |
| 2003/0044967 A1 * | 3/2003 | Heffelfinger | G01J 3/14 356/319 |
| 2003/0124023 A1 | 7/2003 | Burgess et al. | |
| 2003/0178632 A1 | 9/2003 | Hohn et al. | |
| 2003/0207644 A1 | 11/2003 | Green et al. | |
| 2003/0231485 A1 | 12/2003 | Chien | |
| 2004/0008523 A1 | 1/2004 | Butler | |
| 2004/0010299 A1 | 1/2004 | Tolkoff et al. | |
| 2004/0024431 A1 | 2/2004 | Carlet | |
| 2004/0039242 A1 | 2/2004 | Yolkoff et al. | |
| 2004/0047142 A1 | 3/2004 | Goslee | |
| 2004/0147984 A1 | 7/2004 | Altshuler et al. | |
| 2004/0147986 A1 | 7/2004 | Baumgardner et al. | |
| 2004/0158541 A1 | 8/2004 | Notarianni et al. | |
| 2004/0159039 A1 | 8/2004 | Yates et al. | |
| 2004/0162596 A1 | 8/2004 | Altshuler et al. | |
| 2004/0230259 A1 | 11/2004 | Di Matteo | |
| 2004/0262595 A1 | 12/2004 | Mears et al. | |
| 2004/0266546 A1 | 12/2004 | Huang | |
| 2005/0055070 A1 | 3/2005 | Jones et al. | |
| 2005/0104059 A1 | 5/2005 | Friedman et al. | |
| 2005/0107849 A1 | 5/2005 | Altshuler et al. | |
| 2005/0107853 A1 | 5/2005 | Krespi et al. | |
| 2005/0159795 A1 | 7/2005 | Savage et al. | |
| 2005/0207159 A1 | 9/2005 | Maxik | |
| 2005/0212397 A1 | 9/2005 | Murazaki et al. | |
| 2005/0253533 A1 | 11/2005 | Lys et al. | |
| 2005/0267233 A1 | 12/2005 | Joshi | |
| 2006/0006678 A1 | 1/2006 | Herron | |
| 2006/0009822 A1 | 1/2006 | Savage et al. | |
| 2006/0022582 A1 | 2/2006 | Radkov | |
| 2006/0071589 A1 | 4/2006 | Radkov | |
| 2006/0085052 A1 | 4/2006 | Feuerstein et al. | |
| 2006/0138435 A1 | 6/2006 | Tarsa et al. | |
| 2006/0186377 A1 | 8/2006 | Takahashi et al. | |
| 2006/0230576 A1 | 10/2006 | Meine | |
| 2006/0247741 A1 | 11/2006 | Hsu et al. | |
| 2006/0262545 A1 | 11/2006 | Piepgras et al. | |
| 2007/0023710 A1 | 2/2007 | Tom et al. | |
| 2007/0061050 A1 | 3/2007 | Hoffknecht | |
| 2007/0115665 A1 | 5/2007 | Mueller et al. | |
| 2007/0164232 A1 | 7/2007 | Rolleri et al. | |
| 2007/0258851 A1 | 11/2007 | Fogg et al. | |
| 2008/0008620 A1 | 1/2008 | Alexiadis | |
| 2008/0015560 A1 | 1/2008 | Gowda et al. | |

(56) References Cited

U.S. PATENT DOCUMENTS

| | | |
|---|---|---|
| 2008/0091250 A1 | 4/2008 | Powell |
| 2008/0278927 A1 | 11/2008 | Li et al. |
| 2008/0305004 A1 | 12/2008 | Anderson et al. |
| 2008/0307818 A1 | 12/2008 | Min et al. |
| 2009/0018621 A1 | 1/2009 | Vogler et al. |
| 2009/0034236 A1 | 2/2009 | Reuben |
| 2009/0076115 A1 | 3/2009 | Wharton et al. |
| 2009/0154167 A1 | 6/2009 | Lin |
| 2009/0231832 A1 | 9/2009 | Zukauskas et al. |
| 2009/0285727 A1 | 11/2009 | Levy |
| 2009/0314308 A1 | 12/2009 | Kim et al. |
| 2010/0001648 A1 | 1/2010 | De Clercq et al. |
| 2010/0027259 A1 | 2/2010 | Simon et al. |
| 2010/0071257 A1 | 3/2010 | Tsai |
| 2010/0090935 A1 | 4/2010 | Tseng et al. |
| 2010/0102252 A1 | 4/2010 | Harmon et al. |
| 2010/0107991 A1 | 5/2010 | Elrod et al. |
| 2010/0121420 A1 | 5/2010 | Fiset et al. |
| 2010/0148083 A1* | 6/2010 | Brown .................. G01J 3/10 250/372 |
| 2010/0179469 A1 | 7/2010 | Hammond et al. |
| 2010/0232135 A1 | 9/2010 | Munehiro et al. |
| 2010/0246169 A1 | 9/2010 | Anderson et al. |
| 2011/0063835 A1 | 3/2011 | Rivas et al. |
| 2011/0084614 A1 | 4/2011 | Eisele et al. |
| 2011/0256019 A1 | 10/2011 | Gruen et al. |
| 2011/0316025 A1 | 12/2011 | Kuzuhara et al. |
| 2012/0014538 A1 | 1/2012 | Bozkurt et al. |
| 2012/0025717 A1 | 2/2012 | Klusmann et al. |
| 2012/0043552 A1 | 2/2012 | David et al. |
| 2012/0161170 A1 | 6/2012 | Dubuc et al. |
| 2012/0199005 A1 | 8/2012 | Koji et al. |
| 2012/0273340 A1 | 11/2012 | Felix |
| 2012/0280147 A1 | 11/2012 | Douglas |
| 2012/0281408 A1 | 11/2012 | Owen et al. |
| 2012/0315626 A1 | 12/2012 | Nishikawa et al. |
| 2012/0320607 A1 | 12/2012 | Kinomoto et al. |
| 2013/0010460 A1 | 1/2013 | Peil et al. |
| 2013/0045132 A1 | 2/2013 | Tumanov |
| 2013/0077299 A1 | 3/2013 | Hussell et al. |
| 2013/0181246 A1 | 7/2013 | Wu |
| 2013/0200279 A1 | 8/2013 | Chuang |
| 2013/0298445 A1 | 11/2013 | Aoki et al. |
| 2013/0313516 A1 | 11/2013 | David et al. |
| 2013/0313546 A1 | 11/2013 | Yu |
| 2013/0323375 A1 | 12/2013 | Takahashi et al. |
| 2014/0043810 A1 | 2/2014 | Jo et al. |
| 2014/0061509 A1 | 3/2014 | Shur et al. |
| 2014/0209944 A1 | 7/2014 | Kim et al. |
| 2014/0225137 A1 | 8/2014 | Krames et al. |
| 2014/0254131 A1 | 9/2014 | Osinski et al. |
| 2014/0265868 A1 | 9/2014 | Morrisseau |
| 2014/0301062 A1 | 10/2014 | David et al. |
| 2014/0328046 A1 | 11/2014 | Aanegola et al. |
| 2014/0334137 A1 | 11/2014 | Hasenoehrl et al. |
| 2014/0362523 A1 | 12/2014 | Degner et al. |
| 2015/0062892 A1 | 3/2015 | Krames et al. |
| 2015/0068292 A1 | 3/2015 | Su et al. |
| 2015/0086420 A1 | 3/2015 | Trapani |
| 2015/0129781 A1 | 5/2015 | Kretschmann |
| 2015/0148734 A1 | 5/2015 | Fewkes et al. |
| 2015/0150233 A1 | 6/2015 | Dykstra |
| 2015/0182646 A1 | 7/2015 | Anderson et al. |
| 2015/0219308 A1 | 8/2015 | Dross et al. |
| 2015/0233536 A1 | 8/2015 | Krames et al. |
| 2015/0273093 A1 | 10/2015 | Holub et al. |
| 2016/0000950 A1 | 1/2016 | Won |
| 2016/0000953 A1 | 1/2016 | Bettles et al. |
| 2016/0015840 A1 | 1/2016 | Gordon |
| 2016/0030609 A1 | 2/2016 | Peterson et al. |
| 2016/0030610 A1 | 2/2016 | Peterson et al. |
| 2016/0091172 A1 | 3/2016 | Wu et al. |
| 2016/0103068 A1* | 4/2016 | Zhang .................. B01L 7/525 506/12 |
| 2016/0114067 A1 | 4/2016 | Dobrinsky et al. |
| 2016/0168384 A1 | 6/2016 | Guidolin et al. |
| 2016/0249436 A1 | 8/2016 | Inskeep |
| 2016/0271280 A1 | 9/2016 | Liao et al. |
| 2016/0271281 A1 | 9/2016 | Clynne et al. |
| 2016/0273717 A1 | 9/2016 | Krames et al. |
| 2016/0276550 A1 | 9/2016 | David et al. |
| 2016/0324996 A1 | 11/2016 | Bilenko et al. |
| 2016/0345569 A1 | 12/2016 | Freudenberg et al. |
| 2016/0346565 A1 | 12/2016 | Rhodes et al. |
| 2016/0349179 A1* | 12/2016 | Pochette .......... G01N 21/6428 |
| 2016/0354502 A1 | 12/2016 | Simmons et al. |
| 2016/0366745 A1 | 12/2016 | Hikmet et al. |
| 2016/0375161 A1 | 12/2016 | Hawkins et al. |
| 2016/0375162 A1 | 12/2016 | Marry et al. |
| 2016/0375163 A1 | 12/2016 | Hawkins et al. |
| 2017/0014538 A1 | 1/2017 | Rantala |
| 2017/0030555 A1 | 2/2017 | Lalicki et al. |
| 2017/0081874 A1 | 3/2017 | Daniels |
| 2017/0094960 A1 | 4/2017 | Sasaki et al. |
| 2017/0100494 A1 | 4/2017 | Dobrinsky et al. |
| 2017/0100607 A1 | 4/2017 | Pan et al. |
| 2017/0281812 A1 | 10/2017 | Dobrinsky et al. |
| 2017/0368210 A1 | 12/2017 | David et al. |
| 2018/0043044 A1 | 2/2018 | Hachiya et al. |
| 2018/0113066 A1 | 4/2018 | Freitag et al. |
| 2018/0117189 A1 | 5/2018 | Yadav et al. |
| 2018/0117190 A1 | 5/2018 | Bailey |
| 2018/0117193 A1 | 5/2018 | Yadav et al. |
| 2018/0117194 A1* | 5/2018 | Dobrinsky .............. A61L 2/00 |
| 2018/0124883 A1 | 5/2018 | Bailey |
| 2018/0180226 A1 | 6/2018 | Van Bommel et al. |
| 2018/0185533 A1 | 7/2018 | Lalicki et al. |
| 2018/0190625 A1 | 7/2018 | Steckel et al. |
| 2018/0196246 A1* | 7/2018 | Bares .................. G01J 3/0208 |
| 2018/0280723 A1 | 10/2018 | Enwemeka et al. |
| 2018/0299367 A1* | 10/2018 | Yan .................. G01J 3/18 |
| 2018/0311386 A1 | 11/2018 | Hawkins et al. |
| 2019/0070323 A1 | 3/2019 | Atreya et al. |
| 2019/0368936 A1* | 12/2019 | Xu .................. G01J 3/4406 |
| 2019/0371978 A1 | 12/2019 | Iwasa et al. |

FOREIGN PATENT DOCUMENTS

| | | | |
|---|---|---|---|
| CN | 102213382 A | 10/2011 | |
| CN | 105304801 A | 2/2016 | |
| CN | 105339094 A | 2/2016 | |
| CN | 205360038 U | 7/2016 | |
| CN | 106937461 A | 7/2017 | |
| CN | 107575849 A | 1/2018 | |
| CN | 108844929 A * | 11/2018 | ............ G01J 3/0216 |
| DE | 102011001097 A1 | 9/2012 | |
| DE | 102015207999 A1 | 11/2016 | |
| DE | 102016009175 A1 | 2/2017 | |
| EP | 0306301 A1 | 3/1989 | |
| EP | 1693016 A1 | 8/2006 | |
| EP | 1887298 A1 | 2/2008 | |
| EP | 1943880 B1 | 4/2013 | |
| FR | 2773715 A1 | 7/1999 | |
| JP | 2003-332620 A | 11/2003 | |
| JP | 2003339845 A | 12/2003 | |
| JP | 2004261595 A | 9/2004 | |
| JP | 2004275927 A | 10/2004 | |
| JP | 2007511279 A | 5/2007 | |
| JP | 2008-004948 A | 1/2008 | |
| JP | 2009-004351 A | 1/2009 | |
| JP | 2011-513996 A | 4/2011 | |
| JP | 2013-045896 A | 3/2013 | |
| JP | 2013-093311 A | 5/2013 | |
| JP | 2015-015106 A | 1/2015 | |
| JP | 2015-035373 A | 2/2015 | |
| JP | 2015174026 A | 10/2015 | |
| KR | 20130096965 A | 9/2013 | |
| KR | 101526261 B1 | 6/2015 | |
| KR | 20160021100 A | 2/2016 | |
| KR | 101648216 B1 | 8/2016 | |
| KR | 20160127469 A | 11/2016 | |
| KR | 101799538 B1 | 11/2017 | |
| TW | M268106 U | 6/2005 | |
| TW | 201412240 A | 4/2014 | |

(56) References Cited

FOREIGN PATENT DOCUMENTS

| TW | 201604490 A | 2/2016 |
|---|---|---|
| TW | 201611849 A | 4/2016 |
| TW | M530654 U | 10/2016 |
| TW | 201711707 A | 4/2017 |
| TW | 201831977 A | 9/2018 |
| WO | 0114012 A1 | 3/2001 |
| WO | 03037504 A1 | 5/2003 |
| WO | 2003035118 A2 | 5/2003 |
| WO | 03063902 A2 | 8/2003 |
| WO | 03084601 A2 | 10/2003 |
| WO | 03089063 A1 | 10/2003 |
| WO | 2004033028 A2 | 4/2004 |
| WO | 2005048811 A2 | 6/2005 |
| WO | 2005049138 A1 | 6/2005 |
| WO | 2006023100 A1 | 3/2006 |
| WO | 2006100303 A2 | 9/2006 |
| WO | 2006126482 A1 | 11/2006 |
| WO | 2007012875 A1 | 2/2007 |
| WO | 2007035907 A2 | 3/2007 |
| WO | 2008071206 A1 | 6/2008 |
| WO | 2009056838 A1 | 5/2009 |
| WO | 2010110652 A1 | 9/2010 |
| WO | 2015066099 A2 | 5/2015 |
| WO | 2015189112 A1 | 12/2015 |
| WO | 2016019029 A1 | 2/2016 |
| WO | 2016068285 A1 | 5/2016 |
| WO | 2016209632 A1 | 12/2016 |
| WO | 2017009534 A1 | 1/2017 |
| WO | 2017205578 A1 | 11/2017 |
| WO | 2019108432 A1 | 6/2019 |

OTHER PUBLICATIONS

Pelz, A. et al., "Structure and Biosythesis of Staphyloxanthin from *Staphylococcus aureus*," Journal of Biological Chemistry, Sep. 16, 2005, 9 pages.
Sakai, K., et al., "Search Method for inhibitors of staphyloxanthin production by methicillin-resistant *Staphylococcus aureus*," Biol. Pharm. Bull., 2012, vol. 35, No. 1, pp. 48-53, 6 pages.
Clauditz, A. et al., "Staphyloxanthin plays a role in the fitness of *Staphylococcus aureus* and its ability to cope with oxidative stress," Infection and Immunity, 2006, vol. 74, No. 8, 7 pages.
Feng-Chyi Duh et al., "Innovative Design of an Anti-bacterial Shopping Cart Attachment", Journal of Multidisciplinary Engineering Science and Technology (JMEST), Oct. 10, 2015, vol. 2 Issue 10, pp. 2806-2810, http://www.jmest.org/wp-content/uploads/JMESTN42351112.pdf, 5 pages.
Drew Prindle, "This UV-Emitting Door Handle Neutralizes Bacteria, Helps Fight the Spread of Disease", Digital Trends, Jun. 19, 2015, https://www.digitaltrends.com/cool-tech/uv-door-handle-kills-germs/, 11 pages.
Jun. 29, 2018—(DE) Office Action—App 112016003453.9.
Kundrapu et al. "Daily disinfection of high touch surfaces in isolation rooms to reduce contamination of healthcare workers' hands". Journal of Infection Control and Hospital Epidemiology; vol. 33, No. 10, pp. 1039-1042, published Oct. 2012, 6 pages.
Sofia Pitt and Andy Rothman, "Bright idea aims to minimize hospital-acquired infections", CNBC News website, published on Dec. 9, 2014 and retrieved from website: https://www.cnbc.com/2014/12/09/bright-idea-aims-to-minimize-hospital-acquired-infections.html. 5 pages.
Sarah Ward, "LED Retrofit Health ROI? See VitalVio", Poplar Network website, published on Aug. 13, 2014 and retrieved from website: https://www.poplarnetwork.com/news/led-retrofit-health-roi-see-vitalvio, 6 pages.
Mar. 6, 2018—(WO) ISR & WO—App PCT/US2017/068749.
Apr. 16, 2018—(WO) ISR & WO—App PCT/US2017/068755.
Wang, Shun-Chung, et al.; "High-Power-Factor Electronic Ballast With Intelligent Energy-Saving Control for Ultraviolet Drinking-Waler Treatment Systems"; IEEE Transactions on Industrial Electronics; vol. 55; Issue 1; Dale of Publication Jan. 4, 2008; Publisher IEEE, 4 pages.
Berezow Alex, How to Kill Insects With Visible Light, Real Clear Science, Jan. 11, 2015, pp. 1-4<https://www.realclearscience.com/journal_club/2015/01/12/how_to_kill_insects_with_visible_light_109021.html>, 4 pages.
Hori Masatoshi et al., Lethal Effects of Short-Wavelength Visible Light on Insects, Scientific Reports, Dec. 9, 2014, pp. 1-6, Graduate School of Agricultural Science, Tohoku University, Sendai, Japan<https://www.semanticscholar.org/paper/Lethal-effects-of-short-wavelength-visible-light-o-Hori-Shibuya/2c11cb3f70a059a051d8ed02fff0e8a9b7a4c4d4>, 6 pages.
Master Blaster, Tohoku University Team Discovers Blue Light is Effect at Killing Insects, Sora News 24, Dec. 12, 2014, pp. 1-5, Japan, <https://en.rocketnews24.com/2014/12/12/tohoku-university-team-discovers-blue-light-is-effective-at-killing-insects/>, 5 pages.
Dornob, "Healthy Handle: Self-Sanitizing UV Door Knob Kills Germs", Dornob.com, Dec. 5, 2018, pp. 1-6, https://dornob.com/healthy-handle-self-sanitizing-uv-door-knob-kills-germs/, 6 pages.
Kickstarter, "Orb, The World's First Germ-Killing Blue/UV Light Ball", Dec. 10, 2018, pp. 1-10,<https://www.kickstarter.com/projects/572050089078660/orbtm-the-worlds-first-germ-killing-uv-light-ball>, 10 pages.
NuTone, "QTNLEDB LunAura Collection 110 CFM Fan,Light,LED Nightlight, with Tinted Light Panel, Energy Star® Certified Ventilation Fans", Dec. 11, 2018, p. 1, http://www.nutone.com/products/product/a6da75af-8449-4d4d-8195-7011ce977809, 1 page.
NuTone, "NuTone Bath and Ventilation Fans", Dec. 11, 2018, pp. 1-2, http://www.nutone.com/products/filter/qt-series-fanlights-25a05450-d47b-4ab8-9992-f8c2cd3f7b90, 2 pages.
NuTone, "Ultra Pro™ Series Single-Speed Fans and Fan/Lights", Dec. 11, 2018, p. 1, http://www.nutone.com/products/filter/ultra-pro-series-fanlights-eb590f89-dca2-40e7-af39-06e4cccb96ca, 1 page.
Nov. 27, 2018—(JP) Office Action—JP 2018-525520.
Jan. 4, 2019—(TW) Office Action—App 104124977.
Feb. 11, 2019—(WO) ISR—App PCT/US2018/061859.
Feb. 28, 2019—(WO) ISR—App PCT/US2018/061843.
Feb. 28, 2019—(WO) ISR & WO—App PCT/US2018/061856.
Apr. 15, 2019—(CA) Examiner's Report—App 2,993,825.
Absorption and Fluorescence Spectroscopy of Tetraphenylporphyrin§ and Metallo-Tetraphenylporphyrin, article, 2005, 11 pp., Atomic, Molecular and Supramolecular Studies.
Dayer, et al., Band Assignment in Hemoglobin Porphyrin Ring Spectrum: Using Four-Orbital Model of Gouterman, article, Sep. 8, 2009, Protein & Peptide Letters, 2010, vol. 17, No. 4, Department of Biology, Faculty of Sciences, Shahid Chamran University of Ahvaz, Tehran, Iran, 7 pages.
Ayat M. Ali, Effect of MRSA Irradiation by 632, 532, and 405 nm (Red, Blue, and Green) Diode Lasers on Antibiotic Susceptibility Tests, Article, Jun. 2007, 7 pp, vol. 59, No. 2 , 2017, J Fac Med Baghdad.
Nussbaum, et al., Effects of 630-, 660-, 810-, and 905-nm Laser Irradiation, Delivering Radiant Exposure of 1-50 J/cm2 on Three Species of Bacteria in Vitro, journal, 2002, vol. 20, No. 6, 2002, Journal of Clinical LaserMedicine & Surgery, Canada, 9 pages.
Kim, et al., In Vitro Bactericidal Effects of 625, 525, and 425nm Wavelength (Red, Green, and Blue) Light-Emitting Diode Irradiation, article, 2013, 9 pp., vol. 31, No. 11, 2013, Department of Oral Pathology Medical Research Center for Biomineralization Disorders School of Dentistry Dental Science Research Institute, Korea, 9 pages.
Rita Giovannetti, The Use of Spectrophotometry UV-Vis for the Study of Porphyrins, article, 2012, 23 pp., InTech Europe, Croatia.
Josefsen, et al., Unique Diagnostic and Therapeutic Roles of Porphyrins and Phthalocyanines in Photodynamic Therapy, Imaging and Theranostics, article, Oct. 4, 2012, 51 pp., 2012; 2(9):916-966. doi: 10.7150/thno.4571, Ivyspring International Publisher, Department of Chemistry, The University of Hull, Kingston-Upon-Hull, HU6 7RX, U.K., 51 pages.
Jul. 8, 2019—(WO) ISR & WO—App PCT/US2019/024593.
Nov. 5, 2019—(JP) Final Office Action—JP 2018-525520.
Oct. 9, 2019—(CN) Office Action—CN 201680048598.9.

(56) References Cited

OTHER PUBLICATIONS

Oct. 1, 2019—(KR) Office Action—App 10-2018-7005077—Eng Tran.
Apr. 15, 2019—(CA) Office Action—App 2,993,825.
Nov. 20, 2019—(CA) Examiner's Report—App 2,993,825.
Dec. 26, 2019—(TW) Office Action and Search Report—App 107143161.
Dec. 27, 2019—(TW) Office Action and Search Report—App 108111242.
Sep. 6, 2019—(TW) Office Action—App 107143162.
Sep. 20, 2019—(TW) Office Action—App 107143577.
Mar. 18, 2020—(WO) ISR & WO—App PCT/US2019/068799.
Oct. 31, 2008—(WO) ISR & WO—App PCT/GB2008/003679 (Univ Strathclyde).
May 4, 2010—(WO) IPRP—App PCT/GB2008/003679 (Univ Strathclyde).
Apr. 3, 2020—(WO) ISR & WO—App PCT/US2019/67444.
Jun. 1, 2020—(GB) Examiner's Report—App GB1802648.4.
Apr. 14, 2020—(TW) 2nd Office Action—App 107143577 (w/translation).
May 12, 2020—(JP) Final Office Action—JP 2018-525520.
Jun. 18, 2020—(WO) IPRP & WO—App PCT/US2018/061859.
Jul. 6, 2020—(WO) ISR & WO—App PCT/US2019/068799.
Jul. 23, 2020—(TW) Office Action w/TR—TW 108148627.
Jul. 28, 2020—(TW) Office Action 3 w/TR—TW 107143577.
Nov. 23, 2020—(WO) ISR & WO—App PCT/US2020/051254.
Nov. 6, 2020—(TW) Office Action w/Tr.—TW 108146777.
Dec. 2, 2020—(TW) Rejection Decision—App 108111242 (Eng Trans).
Sep. 29, 2020—(WO) ISR & WO—App PCT/US2020/046504.
Gillespie et al., "Development of an antimicrobial blended white LED system containing pulsed 405nm LEDs for decontamination applications," Progress in Biomedical Optics and Imaging, SPIE—International Society for Optical Engineering, Bellingham, WA, vol. 10056, Mar. 14, 2017, pp. 100560Y-100560Y, XP060084045, whole document.
Maclean et al., "Inactivation of Bacterial Pathogens following Exposure to Light from a 405-Nanometer Light-Emitting Diode Array," Applied and Environmental Microbiology, vol. 75, No. 7, Apr. 2009, pp. 1932-1937, 6 pages.
Dai et al., "Blue light for infectious diseases: Propionibacterium acnes, Helicobacter pylori, and beyond?," Drug Resist Update, 15(4): 223-236 {Aug. 2012), 18 pages.
Halstead et al., "The antibacterial activity of blue light against nosocomial wound pathogens growing planktonically and as mature biofilms," Appl. Environ, Microbial., vol. 82, No. 13, Jul. 2016, pp. 4006-4016, 11 pages, retrieved from: https://aem.asm.org/content/aem/82/13/4006.full.pdf.
R.S. McDonald et al., "405 nm Light Exposure of Osteoblasts and Inactivation of Bacterial Isolates From Arthroplasty Patients: Potential for New Disinfection Applications?," European Cells and Materials vol. 25, (2013), pp. 204-214., 12 pages.
Tomb et al., "Inactivation of Streptomyces phage C31 by 405 nm light," Bacteriophage, 4:3, Jul. 2014, retrieved from: http://dx.doi.org/10.4161/bact.32129, 7 pages.
Tsukada et al., "Bactericidal Action of Photo-Irradiated Aqueous Extracts from the Residue of Crushed Grapes from Winemaking," Biocontrol Science, vol. 21, No. 2, (2016), pp. 113-121, retrieved from: https://www.researchgate.net/publication/304628914., 10 pages.
Dec. 8, 2016—(WO) ISR & WO—App PCT/US2016/036704 (Kenall Manufacturing Company).
LEDs Magazine, "Lumination Vio LED combines 405 nm chip with new phosphors," retrieved from the Internet on Apr. 20, 2017 at: http://www.leds.magazine.com/articles/2007/06/lumination-vio-led-combines-405-nm-chip-with-new-phosphors.html. Published Jun. 14, 2007, 2 pages.
LEDs Magazine, "ANSI evaluates revisions to SSL chromaticity standard," retrieved from the Internet on Apr. 20, 2017 at: http://www.ledsmagazine.com/articles/2011/07/ansi-evaluates-revisions-to-ssl-chromaticity-standard-magazine.html, Published Jul. 18, 2011, 4 pages.
LEDs Magazine, "ANSI works to update the solid-state lighting standard for chromaticity," retrieved from the Internet on Apr. 20, 2017 at: http://www.ledsmagazine.com/articles/print/volume-12/issue-2/features/standards/ansi-works-to-update-the-ssl-chromaticity-standard.html, Published Feb. 23, 2015, 5 pages.
LEDs Magazine, "ANSI continues advancements on SSL chromaticity standard," retrieved from the Internet on Apr. 20, 2017 at: http:/lwww.ledsmagazine.com/articles/print/volume-12/issue-11/features/standards/ansi-continues-advancements-on-ssl-chromaticity-standard.html, Published Dec. 8, 2015, 6 pages.
Soraa, "PAR30L," retrieved from the Internet on Apr. 20, 2017 at: http://www_soraa.com/products/22-PAR30L, 6 pages.
Soraa, "PAR30L 18.5W," retrieved from the Internet on Apr. 20, 2017 at: http://wwvv.soraa.com/products, 5 pages.
Bache et al., "Clinical studies of the High-Intensity Narrow-Spectrum light Environmental Decontamination System (HINS-light EDS), for continuous disinfection in the burn unit inpatient and outpatient settings," Burns 38 (2012), pp. 69-76, 8 pages.
Oct. 20, 2016—(WO) ISR & WO—App PCT/US2016/44634.
Color Phenomena, "CIE-1931 Chromaticity Diagram," last updated Aug. 22, 2013, retrieved from www.color-theory-phenomena.nl/10.02.htm on Jan. 20, 2016, 3 pages.
Nov. 2, 2015—(WO) WO & ISR—App PCT/US2015/042678.
Yu, J. et al., "Efficient Visible-Light-Induced Photocatalytic Disinfection on Sulfur-Doped Nanocrystalline Titania," Environ. Sic. Technol., 39, 2005, pp. 1175-1179, 5 pages.
Demidova, T. et al., "Photodynamic Therapy Targeted to Pathogens," International Journal of Im munipathology and Pharmacology, 17(3), pp. 245-254, 10 pages.
Ashkenazi, H. et al., "Eradication of Propionibacterium acnes by its endogenic porphyrins after illumination with high intensity blue light," FEMS Immunology and Medical Microbiology, 35, pp. 17-24, 8 pages.
Elman, M. et al., "The Effective Treatment of Acne Vulgaris by a High-intensity, Narrow Band 405-420 nm Light Source," Cosmetic & Laser Ther, 5, pp. 111-116, 6 pages.
Sikora, A. et al., "Lethality of visable light for *Escherichia coli*hemH 1 mutants influence of defects in DNA repair," DNA Repair 2, pp. 61-71, 11 pages.
Huffman, D. et al., "Inactivation of Bacteria, Virus and Cryptospordium by a Point-of-use Device Using Pulsed Broad Spectrum White Light," Wat. Res. 34(9), pp. 2491-2498, 8 pages.
Papageorgiou, P. et al., "Phototherapy with Blue (415 nm) and Red (660 nm) Light in the Treatment of Acne Vulgaris," British Journal of Dermatology, 2000, pp. 973-978, 6 pages.
Burchard, R. et al., "Action Spectrum for Carotenogenesis in Myxococcus xanthus," Journal of Bateriology, 97(3), 1969, pp. 1165-1168, 4 pages.
Wainwright, "Photobacterial activity of phenothiazinium dyes against methicillin-resistant strains of *Staphylococcus aureus*," Oxford University Press Journals, retrieved from: http://dx.doi.org/10.1111/j.1574-6968.1998.tb12908.x on Jul. 23, 2015, 8 pages.
Yoshimura et al., "Antimicrobial effects of phototherapy and photochemotherapy in vivo and in vitro," British Journal of Dermatology, 1996, 135: 528-532, 6 pages.
Wilson et al., "Killing of methicillin-resistant *Staphylococcus aureus* by low-power laser light," J. Med, Microbial., vol. 42 (1995), pp. 62-66, 5 pages.
Kawada et al., "Acne Phototherapy with a high-intensity, enhanced, narrow-band, blue light source: an open study and in vitro investigation," Journal of Dermatological Science 30 (2002) pp. 129-135, 7 pages.
Maclean et al., "High-intensity narrow-spectrum light inactivation and wavelength sensitivity of *Staphylococcus auresu*," FEMS Microbial. Lett., vol. 285 (2008) pp. 227-232, 6 pages.
Reed, "The History of Ultraviolet Germicidal Irradiation for Air Disinfection," Public Health Reports, Jan.-Feb. 2010, vol. 125, 13 pages.
Ward, "Experiments on the Action of Light on Bacillus anthracis," Received Dec. 15, 1892, 10 pages.

(56) References Cited

OTHER PUBLICATIONS

Hamblin et al., "Helicobacter pylori Accumulates Photoactive Porphyrins and Is Killed by Visable Light," Antimicrobial Agents and Chemotherapy, Jul. 2005, pp. 2822-2827, 6 pages.
Dai et al., "Blue Light Rescues Mice from Potentially Fatal Pseudomonas aeruginosa Burn Infection: Efficacy, Safety, and Mechanism of Action," Antimicrobial Agents and Chemotherapy, Mar. 2013, vol. 57{3), pp. 1238-1245, 8 pages.
Holzman, "405-nm Light Proves Potent at Decontaminating Bacterial Pathogens," retrieved from: http://forms.asm.org/microbe/index.asp?bid=64254 on Aug. 6, 2015, 34 pages.
Guffey et al., "In Vitro Bactericidal Effects of 405-nm and 470-nm Blue Light," Photomedicine and Laser Surgery, vol. 24, No. 6, retrieved from: https:/lwww.liebertpub.com/doi/abs/10.1089/pho.2006.24.684 on Mar. 23, 2018, abstract only provided, 2 pages.
Kristoff et al., "Loss of photoreversibility for UV mutation in *E. coli* using 405 nm or near-US challenge," Mutat Res., May 1983, 109{2): 143-153, 2 pages, abstract only provided.
Turner et al., "Comparative Mutagenesis and Interaction Between Near-Ultraviolet {313- to 405-nm) and Far-Ultraviolet 254-nm) Radiation in *Escherichia coli* Strains with Differeing Repair Capabilities," Journal of Bacteriology, vol. 147, No. 2, Aug. 1981, pp. 410-417, 8 pages.
Knowles et al., "Near-Ultraviolet Mutagenesis in Superoxide Dismutase-deficient Strains of *Escherichia coli*," Environmental Health Perspectives, vol. 102{1), Jan. 1994, pp. 88-94, 7 pages.
Jagger, "Photoreactivation and Photoprotection," Photochemistry and Photobiology, vol. 3, Issue 4, Dec. 1964, retrieved from: https://onlinelibrary.wiley.com/doi/abs/10.1111/j.1751-1097.1964.tb08166.x on Mar. 23, 2018, 4 pages, abstract only provided.
Chukuka et al., Visible 405 nm SLD light photo-destroys metchicillin-resistant *Staphylococcus aureus* {MRSA) in vitro, Lasers in Surgery and Medicine, vol. 40, Issue 10, Dec. 8, 2008, retrieved from: https://onlinelibrary.wiley.com/doi/abs/10.1002/lsm.20724 on Mar. 23, 2018, 4 pages, abstract only provided.
Bek-Thomsen, M., "Acne is Not Associated with Yet-Uncultured Bacteria," J. Clinical Microbial., 2008, 46{10), 9 pages.
Harrison, A.P., "Survival of Bacteria," Annu. Rev. Microbial, 1967, p. 143, vol. 21, 1 page.
Feuerstein et al., "Phototoxic Effect of Visible Light on Porphyromonas gingivalis and Fusobacterium nucleatum: An In Vitro Study," Photochemistry and Photobiology, vol. 80, Issue 3, Apr. 30, 2007, retrieved from: https://onlinelibrary.wiley.com/doi/abs/10.1111/j.1751-1097.2004.tb00106.x on Mar. 23, 2018, abstract only, 4 pages.
Pochi, P.E., "Acne: Androgens and microbiology," Drug Dev, Res., 1988, val. 13, 4 pages, abstract only provided.
Burkhart, C. G. et al., "Acne: a review of immunologic and microbiologic factors," Postgraduate Medical Journal, 1999, vol. 75, pp. 328-331, 5 pages.
Jappe, U., "Pathological mechanisms of acne with special emphasis on Propionibacterium acnes and related therapy," Acta Dermato-Venereologica, 2003, vol. 83, pp. 241-248, 8 pages.
Burkhart, C. N. et al., "Assessment of etiologic agents in acne pathogenesis," Skinmed, 2003, vol. 2, No. 4, pp. 222-228, 7 pages.
Tong, Y., et al. "Population study of atmospheric bacteria at the Fengtai district of Beijing on two representative days," Aerobiologica, 1993, vol. 9, 1 page, Abstract only provided.
Tong, Y. et al., "Solar radiation is shown to select for pigmented bacteria in the ambient outdoor atmosphere," Photochemistry and Photobiology, 1997, val. 65, No. 1, pp. 103-106, 4 pages.
Marshall, J. H., et al., "Pigments of *Staphylococcus au reus*, a series of triterpenoid carotenoids," J. Bacteriology, 1981, vol. 147, No. 3, pp. 900-913, 14 pages.

\* cited by examiner

CONTAMINATION LOAD SENSING DEVICE

CROSS-REFERENCE TO RELATED APPLICATION

This application claims the benefit of U.S. Provisional Application No. 62/826,198, titled "Bacterial Load Sensing Device" and filed on Mar. 29, 2019. The above-referenced application is hereby incorporated by reference in its entirety.

TECHNICAL FIELD

Aspects of the present disclosure generally relate to processes, systems, and apparatus for bacterial load sensing.

BACKGROUND

Many industries may desire a method and/or device capable of providing real time surface contamination (e.g., bacterial load) detection. There are limited existing solutions on the market that are able to measure bacterial load, also known as bioburden. Many existing methods for measuring bacterial load are not real time and/or require human input. Industries, such as the healthcare industry, are held responsible for contamination management, e.g., due to a high bacterial load. Pathogenic contamination can lead to hospital acquired infections (HAIs) which cost hospitals across the United States billions of dollars each year. Other industries, such as the pharmaceutical industry and food processing industry, are held to strict regulations in regards to contamination of pharmaceuticals and food products and may benefit from additional bacterial load detection. Many current cleaning, disinfection, and sanitation methods are blind in the sense that the location of high risk contamination areas are typically unknown beyond obvious tells (e.g., visible contamination and/or perceivable odor). This may lead to ineffective cleaning protocols which may be greatly problematic when attempting to mitigate hospital acquired infections in healthcare settings or preventing contamination leading to illness outbreaks in preparing pharmaceuticals or food products.

SUMMARY

The following presents a simplified summary in order to provide a basic understanding of some aspects of the disclosure. The summary is not an extensive overview of the disclosure. It is neither intended to identify key or critical elements of the disclosure nor to delineate the scope of the disclosure. The following summary merely presents some concepts of the disclosure in a simplified form as a prelude to the description below.

An example contamination sensing device may comprise a body, a light emitter disposed on the body and configured to emit an excitation wavelength of light toward a surface, a sensor disposed on the body, configured to detect light, and directed toward the surface, and a filter adjuster configured to determine, based on the excitation wavelength of light, a filter configured to remove light outside of an emission wavelength range, wherein the emission wavelength range corresponds to wavelengths of light emitted by contamination upon exposure to the excitation wavelength of light, and adjustably move the filter in front of the sensor.

An example contamination sensing system may comprise a light emitting device configured to emit an excitation wavelength of light toward a surface, a light detecting device, in communication with the light emitting device, comprising a sensor configured to detect light and directed toward the surface, and a filter adjuster configured to determine, based on the excitation wavelength of light, a filter configured to remove light outside of an emission wavelength range, wherein the emission wavelength range corresponds to wavelengths of light emitted by contamination upon exposure to the excitation wavelength of light, and adjustably move the filter in front of the sensor.

An example contamination sensing device may comprise a body, at least one light emitter disposed on the body and configured to emit a light comprising an excitation wavelength toward a surface, and a plurality of sensors disposed on the body and directed toward the surface, wherein each sensor of the plurality of sensors is configured to detect a different emission wavelength corresponding to respective wavelengths of light emitted by contamination upon exposure to the emitted light.

The foregoing and other features of this disclosure will be apparent from the following description.

BRIEF DESCRIPTION OF THE DRAWINGS

Examples herein will be described in detail, with reference to the following figures, wherein like designations denote like elements.

DETAILED DESCRIPTION

In the following description of the various examples, reference is made to the accompanying drawings, which form a part hereof, and in which is shown by way of illustration, various examples that may be practiced. It is to be understood that other examples may be utilized.

Disinfecting lighting systems (e.g., antimicrobial lighting systems) utilizing safe visible light have been deployed in many markets including healthcare, pharmaceuticals, food service, horticulture, hospitality, residential, and more. Disinfecting lighting systems may be able to provide an intensity of disinfecting energy sufficient for inactivating microorganisms (e.g., bacteria). Although these disinfecting lighting fixtures and the lighting layouts of the rooms disinfecting lighting fixtures may be installed in are often designed to produce the required intensity on surfaces to inactivate microorganisms on those surfaces, there are limited feedback methods to prove that the disinfecting lights are working.

In healthcare environments there may be a desire for a real time disinfection validation tool to indicate if disinfection methods reduce pathogens on surfaces. Hospital acquired infections (HAI) are a significant issue. Hospital acquired infections may occur from the transmission of microorganisms from direct contact with other humans or intake of microorganisms from the environment. During an HAI outbreak, a hospital may use traditional methods to test a surface for pathogenic bacteria, such as, for example, surface swabbing and a bacteria culture test. Although cleaning, disinfection, and/or sterilization practices may be put into place, it may be difficult to appropriately direct those resources within allotted times. Manual cleaning may be extremely costly in terms of materials and labor, and may be prone to human error. Healthcare settings may benefit greatly from identification of high risk areas for harmful microorganisms. Identification of high risk areas may allow for directing disinfection efforts through, for example, manual cleaning or disinfecting lighting. A real time or near real time method for testing environmental surfaces for contamination, such as, for example, bacteria, pathogens, microorganisms, grease, organic matter, non-organic matter, etc., may be helpful to prevent outbreaks, indicate when cleaning is needed, or otherwise indicate when a surface is contaminated. For example, processes for bacterial load detection may be partially or fully automated and may determine bacterial loads within minutes.

Industries such as pharmaceutical and food processing industries may face strict regulations to prevent the outbreak of illness caused by contaminated goods and/or surfaces. Characterization of bacterial load for non-human goods and/or surfaces, such as, for example, pre or post processed food products, medicine, and/or live agriculture may help manage contamination that may lead to disease (e.g., food borne illnesses).

Figure 1:
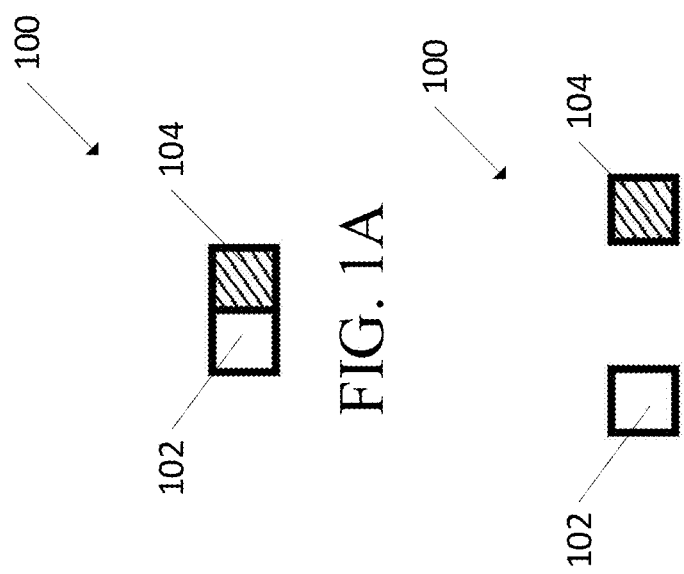
FIGS. 1A-1B illustrate an example contamination sensing device.

As illustrated in FIGS. 1A-1B, a contamination sensing device 100 may comprise an excitation light source(s) 102 and a sensor(s) 104. The contamination sensing device 100 may integrate with additional processors (e.g., processors of FIGS. 11, 12, 22), control systems (e.g., control system of FIG. 12), and/or computer vision algorithms to complete all of its functions. The contamination sensing device 100 may also comprise an additional camera configured to capture light in the visible light spectrum. The contamination sensing device 100 may be housed in a variety of different manners wherein the components of the contamination sensing device 100 are coupled together, as shown in FIG. 1A or physically separate as shown in FIG. 1B.

The excitation light source 102 may comprise, for example, an LED, an array of LEDs, a laser, an array of lasers, a vertical cavity surface emitting laser (VCSEL), or an array of VCSELs. Other light emitters that may be used as excitation light source(s) 102 may include, for example, any emitter capable of emitting ultraviolet light including LEDs, fluorescent lamps without phosphor coatings, xenon arc lamps, mercury vapor, short-wave UV lamps made with fused quartz, black lights (fluorescent lamp coated with UVA emitting phosphor), amalgam lamps, natural or filtered sunlight, incandescent lamps with coatings that absorb visible light, gas-discharge (argon, deuterium, xenon, mercury-xenon, metal-halide, arc lamps), halogen lamps with fused quartz, excimer lamps, etc. In some examples, an LED emitter may comprise at least one semiconductor die and/or at least one semiconductor die packaged in combination with light converting materials. In some examples, the excitation light source(s) 102 may be fitted with optical components that may alter the path of the excitation light. (e.g., focus the light into a beam).

FIG. 1A provides an example contamination sensing device 100 where the sensor(s) 104 and the excitation light source(s) 102 are coupled together and FIG. 1B provides an example where the excitation light source(s) 102 and the sensor(s) 104 are physically separated. In some examples, the sensor(s) 104 may be mounted on the ceiling and configured for a top-down, bird's eye view of the space, which may allow for easier image capture and mapping to real space locations/coordinates. The sensor(s) 104 may be located directly above the surface of interest. The excitation light source(s) 102 may be mounted separately, for example, in the corner of a room, at any angle (e.g., 90 degrees) from the sensor(s) 104 which may reduce the amount of incident light hitting the sensor(s) 104. Reduction of stray light from the excitation light source(s) 102 or any other light producing source may allow the sensor(s) 104 to take a more accurate reading. A reduction in noise caused by ambient light may result in a clearer fluorescence signal from the microorganisms and/or bacterial load. In some examples, such as where the excitation light source(s) 102 and sensor(s) 104 are physically coupled, as shown in FIG. 1A, a dichroic filter may be used and/or mounted at an angle to reflect the excitation light towards a target surface, while optimally only transmitting the fluorescence wavelengths to be measured.

In some examples, bacterial load (e.g., contamination on surfaces within an indoor and/or outdoor space) may be detected, measured, and/or characterized by the contamination sensing device 100. Detection may comprise determining whether a surface is contaminated (e.g., high levels of bacteria, chemical residue, presence of microorganisms, etc.). In some examples, contamination may be determined by the contamination sensing device 100 determining that a bacterial load exceeds a threshold limit, at which point the surface may be considered contaminated. Measurement may comprise identifying high risk areas (e.g., identifying where bacteria are located) and determining levels of bacteria on the surface (e.g., where bacteria are most concentrated/dense). Characterization may comprise determining types of microorganisms (e.g., bacteria) present on the surface. Data may be provided for use by a control system integrated with disinfecting light fixture(s) or a disinfecting lighting system and/or provided to a user through a user interface. A user may be able to make recommendations, based on the bacteria concentration, for directing manual cleaning to high risk areas. Verification may be provided for disinfection through storing data over time to show trends in bacteria locations and measured surface bacterial load. A real time method may be provided for determining if disinfecting techniques (e.g., disinfecting lighting system or traditional chemical cleaners) are working.

An example method for measuring bacterial load may utilize an oxygen depletion sensor. Oxygen depletion sensors may detect very small changes in oxygen and create oxygen profiles that may reflect microbial growth in order to determine microbial contamination. The Oxygen depletion method may be most applicable to measuring contamination in the air. Oxygen depletion may be used for surface monitoring but, in some examples, may require a user to swab a surface and place the swab into a vial containing fluorescent 02 sensitive polymers that will react to the depletion of oxygen due to the bacteria growth. The depleted oxygen (e.g., oxygen consumed by the bacteria) may correlate to a microbial load. The time it takes from swabbing to determining results, measured in colony forming units (CFUs), may, in some examples, take several hours and therefore may not be real time or instantaneous. Some examples may operate in real time or near real time (e.g., within minutes), allowing users and/or system to utilize the data collected nearly instantaneously. Some examples of oxygen depletion sensors may require a person to take a sample of a surface, and may not provide real time or near real time operation. In some examples, the contamination sensing device 100 may not require any human intervention to take the measurements. The contamination sensing device 100 may work in the background with minimal to no extra effort from a user.

Another example method for measuring bacterial load utilizes an ATP meter or luminometer. ATP meters or luminometers measure Adenosine Triphosphate (ATP) molecules which may correlate to the cleanliness of a surface/water. ATP meters take measurements in relative light units (RLU) based on the bioluminescence of ATP created from the addition of luciferase enzyme to convert ATP into adenosine monophosphate. The addition of luciferase enzyme to convert ATP into adenosine monophosphate may result in the emission of light. An ATP meter quantifies the emission of light in RLUs which may be proportional to the amount of ATP in a sample. ATP meters require human intervention to take the measurements. For example, a user is required to swab a desired surface and place a sample from the swab within the ATP meter analysis. Some studies have shown there may not be a direct correlation between RLU and actual microbial counts which may decrease the reliability of surface contamination detection. Some studies have shown that chemical surface cleaners with active ingredients such as isopropyl alcohol, citric acid, sodium hypochlorite, etc., may interfere with the analysis of a sample by an ATP meter. In high risk areas, such as healthcare spaces, disinfectants may be used often, making ATP meters unreliable as a source of measuring surface contamination. Another study analyzed several different ATP meters and found poor detection and linearity with swabbing surfaces. Surface swabs may be unreliable at picking up the total surface ATP. ATP meters also require a minimum concentration of bacteria to make a measurement, and therefore may not be used for surfaces with low concentrations of bacteria. Due to these limitations, ATP meters are an unreliable method for measuring surface contamination.

An example method for measuring bacterial load comprises bacterial culture tests. Bacterial culture tests are manually intensive. Bacterial culture tests provide a measure of bacteria count measured in CFUs. Bacterial culture tests rely on a person taking a sample of a surface and allowing the cultures within the sample to cultivate. The results of bacterial culture tests are only as reliable as the sample taken. Bacterial culture tests may not provide accurate information if the most representative surface is not sampled. Studies have shown that once bacteria have adhered to a surface they may become more difficult to remove, thus decreasing test accuracy. Once a surface sample is taken, bacterial culture tests requires time for bacteria to grow after being deposited in a special medium. Bacterial growth may take several days before the bacterial culture test provides viable information. Bacterial culture test are a labor intensive and time consuming option for surface contamination testing. Bacterial culture tests require extensive lab equipment and therefore may often not be completed within the space being tested. Instead, bacterial culture samples may be sent to a lab and require several days to perform.

The contamination sensing device 100 may be configured to detect, measure, map the locations of, and/or characterize microorganisms within a space. The contamination sensing device 100 may detect and/or measure levels of bacteria, microorganisms, microbes, yeast, mold, fungi, and/or contamination in a space. The contamination sensing device 100 may not require human intervention or performance of any special tasks, such as growing the bacteria from a sample, to take measurements. The contamination sensing device 100 may operate without chemical reactions and therefore may minimize procedural complications. Another advantage of the contamination sensing devices 100 comprises algorithmically determining whether chemical cleaners have been used on surfaces, which may cause interference with measurements, and eliminating such interference. In some examples, the contamination sensing device may determine areas that have been cleaned by chemical cleaners. The contamination sensing device 100 may determine areas that have been cleaned, for example, by measuring fluorescence emitted by residue from chemical cleaners. In some examples, the contamination sensing device 100 may flag areas that have not been cleaned. In some examples, the contamination sensing device 100 may indicate, to a user, areas that have not been cleaned. In some examples, the contamination sensing devices disclosed herein may work in real time or near real time (e.g., within minutes) to provide instant or near instant feedback to users. In some examples, all or a majority of the physical components of the contamination sensing device may be contained in the space being measured. In some examples, the contamination sensing device may work on an interior room scale.

In some examples, the excitation light source(s) 102 may emit an excitation light that may cause microorganisms (e.g., bacteria, contamination, etc.) to fluoresce. Fluorescence may be caused by absorption of a first wavelength which may cause a second longer wavelength to be emitted. This fluorescence may be referred to as autofluorescence, as the microorganisms themselves may be fluorescing without additional exogenous photosensitizers. Autofluorescence may be measured by the sensor(s) 104 designed to detect the wavelengths emitted by microorganisms. In some examples, cleaners with photosensitizers may be used to increase the fluorescence of bacterial contamination. The contamination sensing device 100 may be in communication with a database of excitation and/or emission spectra of various bacteria/microorganisms such that measured/observed fluorescence may be compared against the database to identify bacteria/microorganism types. The contamination sensing device 100 may be in communication with a database of excitation and/or emission spectra of chemicals and/or other nonorganic materials.

Different types of microorganisms (e.g., bacteria) may fluoresce at different wavelengths. The contamination sensing device 100 may use fluorescing color (e.g., using color filtering and threshold matching to that color) to classify bacteria into categories. In some examples, a contamination sensing device 100 may determine that a measurement does not contain a certain bacteria type because a surface does not emit the corresponding wavelength(s). In some examples, a contamination sensing device 100 may determine a measurement does contain a certain bacteria type because the surface does emit the corresponding wavelength(s).

In some examples, an excitation light may be emitted by the excitation light source(s) 102 and may be a specific wavelength. In some examples, the excitation wavelength may be a range of wavelengths. In some examples, the excitation light may be UV (e.g., UV-A around approximately 365 nanometers (nm)) or visible/near UV (e.g., 405 nm). In some examples, the excitation wavelength used may be between 300 nm and 500 nm. In some examples, the excitation wavelength or wavelength range may be between 300 nm and 400 nm. In some examples, the excitation wavelength used may be between 350 nm and 380 nm. In some examples, the excitation wavelength used may be between 380 nm and 420 nm. In some examples, the excitation wavelength or wavelength range may be between 200 nm and 350 nm. In some examples, the excitation wavelength may be approximately 230 nm and/or approximately 280 nm, for example, to initiate the autofluorescence of tryptophan, which may be found in many bacteria. In some examples, multiple excitation peak wavelengths may be used.

In some examples, a minimum proportion of spectral energy (e.g., percentage of spectral energy) may be required for a desired excitation wavelength or within a desired excitation wavelength range. For example, if the excitation light source(s) 102 is a broad spectrum UV light emitter, and the broad spectrum UV light emitter emits a total spectral energy within a range of 300 nm to 400 nm, but the desired excitation wavelength range is 350 nm to 380 nm, a minimum proportion of spectral energy in the range of 350 nm to 380 nm out of the total spectral energy may be configured to be a minimum percentage (e.g., 50%). In some examples, the total spectral energy may be configured to be a minimum percentage greater than 50%. In some examples, the total spectral energy may be configured to be a minimum percentage less than 50%. This minimum proportion of spectral energy may reduce energy usage towards unnecessary wavelengths.

Irradiance, measured in milliWatts per centimeter squared (mW/cm$^2$), may be used to quantify how much excitation light from the excitation light source(s) may be required to initiate autofluorescence from microorganisms on a target surface. Irradiance may be adjusted by altering the intensity (e.g., increasing the power) of the light coming out of the light source (e.g., brightness) and/or adjusting the distance between the excitation light source(s) and the target surface(s). More power may be required as the distance between the excitation light source(s) and the target surface(s) increases. In some examples, the contamination sensing device 100 may provide a required minimum irradiance on the target surface(s). The required minimum irradiance may be the minimum irradiance necessary to initiate autofluorescence. The required minimum irradiance may affect how this contamination sensing device 100 is designed into a room layout. As the distance between the excitation light source(s) 102 and the target surface(s) increases, more power may be used by the excitation light source(s) 102 to provide the required minimum irradiance on the target surface(s).

In some examples, a minimum irradiance (e.g., 0.01 mW/cm$^2$) at a surface may be required to initiate autofluorescence. Irradiance is the power per unit area at a distance away from the light source. In some examples, an irradiance of 0.05 mW/cm$^2$ may initiate autofluorescence on a surface, but higher values such as, for example, 0.1 mW/cm$^2$, 0.5 mW/cm$^2$, 1 mW/cm$^2$, or 2 mW/cm$^2$ may be used. In some examples, higher irradiances may be required (e.g., 3 to 10 mW/cm$^2$). In some examples, 10 to 50 mW/cm$^2$ may be required. In some examples, greater than 50 mW/cm$^2$ may be required (e.g., 100 mW/cm$^2$). In some examples, approximately 1,500 mW/cm$^2$ may be required and/or utilized.

In some examples, lux (lumens/m$^2$) may be used to quantify the excitation light source(s) 102. In some examples, 500 lux may be required on the surface. In some examples, a lux between 20,000,000 and 4,000,000,000 may be used and/or required. In some examples, a radiant flux may be required by the excitation light source of 50 to 250 Watts. Radiant flux, measured in Watts, is the total power from the light source.

In some examples, the irradiance on the target surface from the excitation light source(s) 102 may be approximately 10 mW/cm$^2$, and the excitation light source(s) 102 may be located 5 feet (152.4 cm) from the target surface. The excitation light source(s) 102 located 5 feet from the target surface with an irradiance of 10 mW/cm$^2$ may require a radiant flux out of the excitation light source(s) 102 of approximately 232.26 Watts. In some examples, the excitation light source(s) 102 may be located 1 foot (30.48 cm) from the target surface and may be substantially directly above the target surface. The same irradiance of 10 mW/cm$^2$ may be used on the target surface. The excitation light source(s) 102 located 1 foot from the target surface with an irradiance of 10 mW/cm$^2$ may require a radiant flux out of the excitation light source(s) 102 of approximately 9.29 Watts. These calculations are approximations based on the inverse square law, as shown in Equation 1 below and assuming the excitation light source is a point source, wherein E is the irradiance, I is the radiant flux, and r is the distance from the excitation light source to a target surface.

$$E \cong \frac{I}{r^2} \quad \text{Equation 1}$$

The contamination sensing device 100 may be configured to detect irradiance. An irradiance sensor may be useful for determining the amount of light and/or disinfecting energy that is being delivered to a surface. The irradiance may be measured directly, for example, if the contamination sensing device is mounted to a surface to be measured. In some examples, the irradiance may be measured indirectly from a reflection off of the surface to be measured by the sensor(s) 104. In some examples, the sensor(s) 104 may be radiometrically calibrated using a reference light source with a known emission spectrum and irradiance. New measurements may be compared to the stored calibration value to determine irradiance or lux of a light being measured.

As described above, autofluorescence of contamination such as bacteria is the natural fluorescence emitted from bacteria after illuminating such bacteria with a specific wavelength of light. Different bacteria may be excited by different wavelengths of light and may emit different wavelengths during autofluorescence. After being exposed to the excitation light, light emitted from the bacteria may range, for example, from 400 nm to 800 nm. Tryptophan is a compound that may be found in several different types of bacteria. Tryptophan emission may peak at around 340 nm with dual excitation wavelengths of about 230 nm and 280 nm. Pyoverdine, for example, may be found in *Pseudomonas* strains, and may have an emission peak, between 430 nm and 530 nm (e.g., in the visible range), of about 455 nm, and a maximum excitation wavelength of about 395 nm. In some examples, a minimum quantity of bacteria may be necessary to detect a measurable signal.

Many types of microorganisms/bacteria may fluoresce after exposure to an excitation wavelength. For example, bacterial fluorescence may be due to bacteria containing intracellular and/or extracellular fluorophores. Bacteria of interest, for example, may include potentially pathogenic bacteria of concern to the healthcare industry as well as bacteria associated with contamination in the food processing industry.

Examples of detectable bacteria may include, for example, *Pseudomonas aeruginosa, Escherichia coli, Salmonella, Campylobacter, Staphylococcus aureus, Staphylococcus carnosus, Clostridium difficile, Klebsiella pneumoniae, Serratia marcescens, Proteus mirabilis*, as well as many other gram positive and gram negative bacteria. Other bacteria that may autofluoresce include, for example: *Staphylococcus aureus* (incl. MRSA), *Clostridium perfringens, Clostridium difficile, Enterococcus faecalis, Staphylococcus epidermidis, Staphylococcus hyicus, Streptococcus pyogenes, Listeria monocytogenes, Bacillus cereus, Mycobacterium terrae, Lactococcus lactis, Lactobacillus plantarum, Bacillus circulans* and *Streptococcus thermophiles, Acinetobacter baumannii, Pseudomonas aeruginosa, Klebsiella pneumoniae, Proteus vulgaris, Escherichia coli, Salmonella enteritidis, Shigella sonnei, Serratia* spp., and *Salmonella typhimurium*. Some bacterial endospores may include *Bacillus cereus* and *Clostridium difficile*. Other bacteria may also autofluorescence and be detectable.

Non-living and/or non-organic surfaces may autofluoresce. In some examples, the contamination sensing device 100 may be able to account for the emission of fluorescing light from a non-living and/or non-organic surface (e.g., light that is not coming from microorganisms). Some common materials in healthcare settings may include, for example, stainless steel, polypropylene, nylon polyester paint, microfiber cloth, bedding materials, plastics for nurse call systems/buttons, etc. Other common surface materials include wood, paint, protective coatings, stone, metals, plastics, glass, concrete, paper composites, laminate, etc. In some examples, it may be determined whether cleaning residue remains on a surface to ensure such cleaning residue does not interfere with surface bacterial load detection. For example, several common hospital materials including, for example, microfiber cloth, colored plastics (e.g., white, black, yellow, orange), stainless steel, polypropylene and several others, may fluoresce after being exposed to excitation light. For example, microfiber cloth may emit a peak wavelength in the range of 300-350 nm with excitation wavelengths of 280-340 nm. The microfiber cloth fluorescence may overlap with some known bacterial emissions. In some examples, data, including fluorescent profiles of common materials and cleaners, may be stored for use in algorithms for determining surface bacterial load with these materials taken into consideration. Another common material in healthcare and food processing settings is stainless steel, which may fluoresce, for example, around 400-500 nm with excitation wavelengths between 350-450 nm.

In addition to surfaces such as counters, fluorescence measurements of surfaces of various objects (e.g., computer keyboard, cell phone, bedding, food products, plants, medicines, etc.) may be taken. In some examples where excitation light exposure is not harmful to humans, the fluorescence of a human may be measured. In some examples, fluorescence measurements may be obtained on a product level scale or an entire room scale. Fluorescence may be measured for small surface areas (e.g., 1 cm$^2$) and/or large surface areas (e.g., 10 m$^2$). Fluorescence may be measured for even smaller and larger surface areas. The location of the contamination sensing device and the components of the contamination sensing device may be adjusted appropriately for different applications.

In some examples, the contamination sensing device 100 may be handheld. A handheld contamination sensing device 100 may, for example, comprise a safety mechanism configured to determine a maximum irradiance exposure limit. The contamination sensing device 100 may, based on the maximum irradiance exposure limit, determine a maximum irradiance emitted by the excitation light source(s) 102. In some example, contamination sensing device 100 may determine if the sensor(s) 104 are directed normal to the surface to be measured. The contamination sensing device 100 may, based on readings from the sensor(s) 104, determine if the sensor(s) 104 are directed normal to the surface to be measured. In some examples, the contamination sensing device 100 may use computer vision algorithms to determine if the sensor(s) 104 are directed normal to the surface to be measured.

Figure 2:
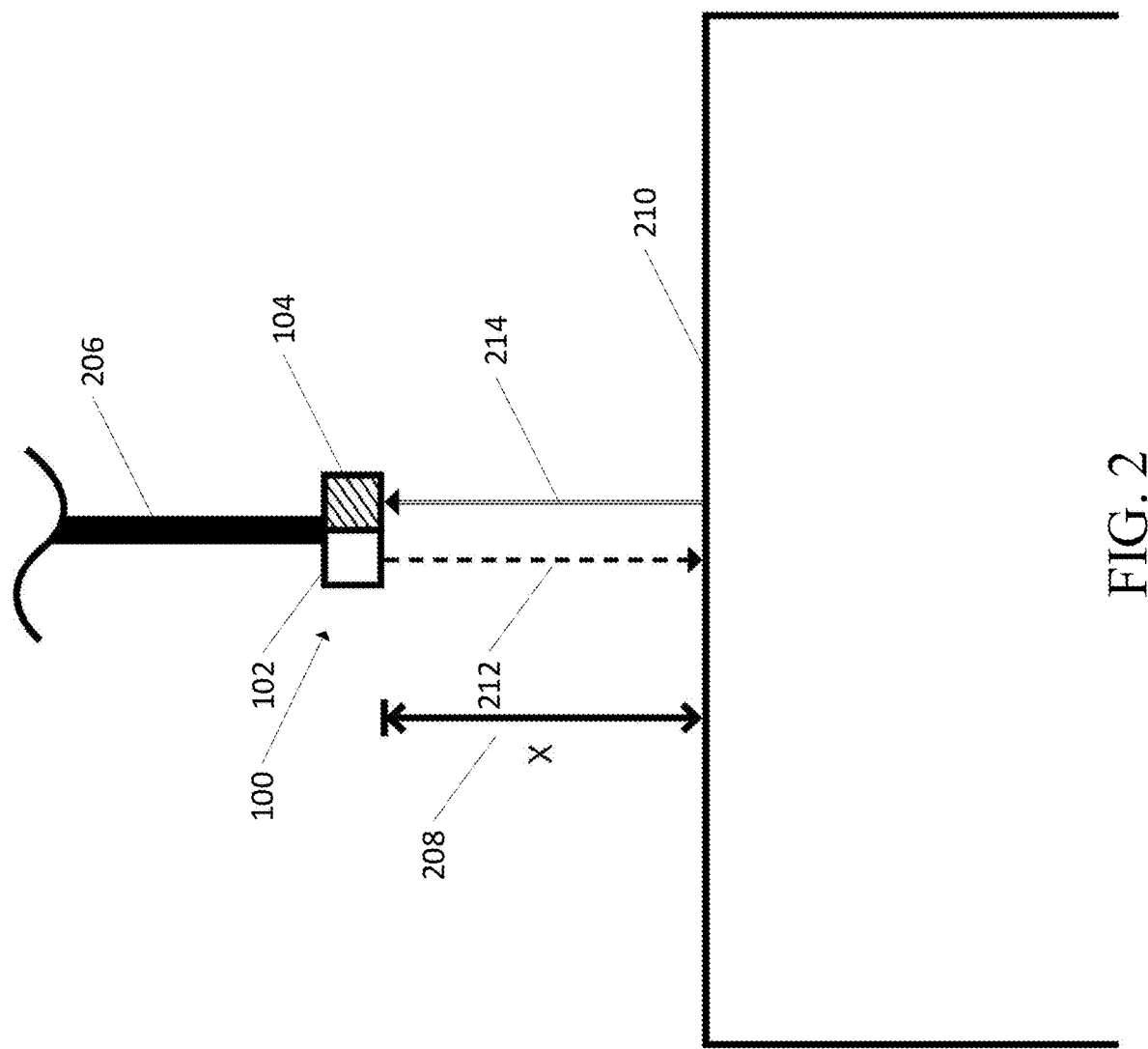
FIG. 2 illustrates an example contamination sensing device and target surface.

In some examples, the contamination sensing device 100 or the individual components of the contamination sensing device 100 (e.g., sensor(s) 104, excitation light source(s) 102, etc.) may be adjustable in height and/or location in order to accurately measure bacterial load on a desired surface. FIG. 2 shows an example contamination sensing device 100 attached to an adjustable arm 206 at a distance 'X' 208 from a target surface 210. The adjustable arm 206 may enable movement of the contamination sensing device 100. The adjustable arm 206 may be movable, for example, to increase or decrease the distance 208 from a target surface 210. The excitation light 212 from the excitation light source(s) 102 may be emitted towards the target surface 210. Microorganisms on the target surface 210 and/or the target surface 210 may autofluoresce in response to the excitation light 212. Emitted light 214 (e.g., light caused by autofluorescence) from the target surface 210 (e.g., emitted by the surface and/or microorganisms on the surface) may be detected by the sensor(s) 104. In some examples, the emitted light 214 may comprise autofluorescence from microorganisms on the target surface.

Figure 3:
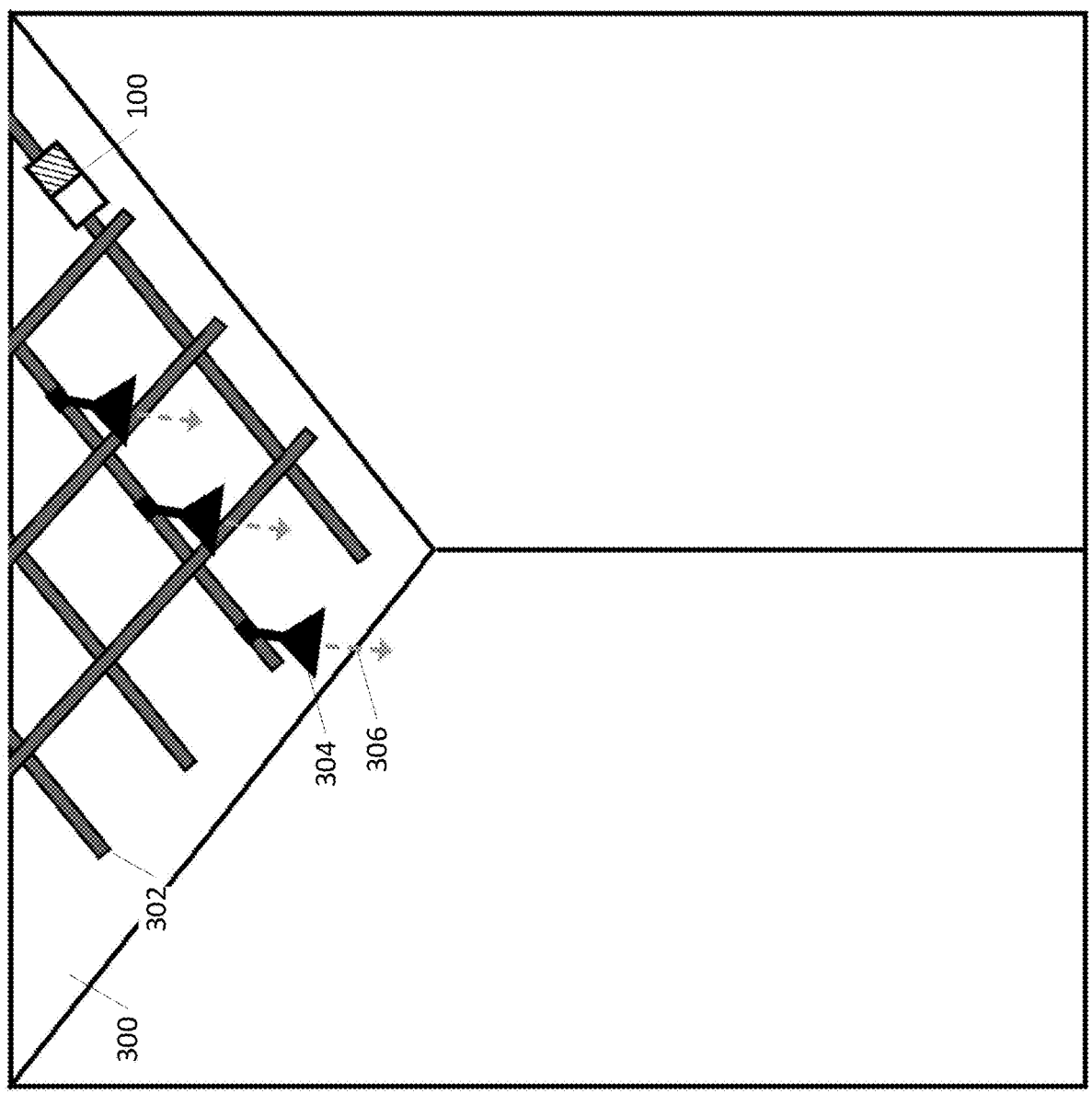
FIG. 3 illustrates an example mounted contamination sensing device.

An example ceiling mounted contamination sensing device 100 is shown in FIG. 3. The contamination sensing device 100, or a component of the contamination sensing device 100 (e.g., sensor(s) 104), may be mounted to allow for movement along the X, Y, and Z axes in the space, as well as any degree of rotation. In some examples, the contamination sensing device 100 may be wireless, transportable, and/or easy to set up over any desired surfaces. In some examples, the contamination sensing device 100 may be installed permanently in place in a room at an effective location for measuring surface bacterial load. In some examples, the contamination sensing device 100 may be part of a track system 302. The track system 302 may be mounted, for example, on/near a ceiling 300 and may allow for the contamination sensing device 100 to be easily moved. In some examples, an optional light fixture(s) 304 may be used to output light 306. The light 306 from the optional light fixture(s) 304 may comprise illuminating light, excitation light to initiate autofluorescence, and/or disinfecting light. FIG. 3 illustrates the track system 302 configured in a grid pattern for the movement of items attached to the grid (e.g., contamination sensing device 100), but other track/rail patterns are possible. Additional sensor(s) 104 (e.g., occupancy sensors) may be attached to the track system 302. In some examples, the contamination sensing device 100 may be attached to a moveable arm capable of adjusting the location of the contamination sensing device 100. In some examples, the movable arm 206 shown in FIG. 2 may be attached/mounted to the track system 302 of FIG. 3.

The contamination sensing device 100 (e.g., the excitation light source(s) 102 and/or sensor(s) 104) may be located at various heights relative to the target surface 210. In some examples, the target surface 210 may be 1 to 4 feet from the floor, and the contamination sensing device 100 may be located on the ceiling 300, which may be 7 to 10 feet from the floor. In some examples, the contamination sensing device 100 may be located anywhere from 1 inch to 10 feet from the target surface 210. In some examples, the contamination sensing device 100 may be located closer than 1 inch or further than 10 feet from the target surface 210. As the distance between the target surface 210 and the contamination sensing device 100 increases, the intensity of the excitation light 212 may be increased to provide an optimal irradiance on the target surface 210 to initiate the autofluorescence of bacteria. In some examples, the contamination sensing device 100 may be attached to a mechanism (e.g., adjustable arm 206) making the distance between the contamination sensing device 100 and the target surface 210 adjustable in order to optimize the measurements. A motor, for example, may be incorporated into the track system 302 or the contamination sensing device 100 so that the contamination sensing device 100 may move on the track system 302 and/or to otherwise adjust its distance 208 to the target surface 210. In some examples, the contamination sensing device 100 may be moved, for example, by a control system, which may increase or decrease the distance 208 between the target surface 210 and the autofluorescence bacterial load sending device 100. As the distance 208 between the target surface 210 and the contamination sensing device 100 decreases, the surface area of the target surface 210 that may be obtained in the measurement also decreases.

In some examples, the contamination sensing device 100 may comprise a distance sensor. The distance sensor, for example, may be able to detect the distance 208 from the contamination sensing device 100 to the target surface 210. The distance sensor, in some examples, may be a Time-of-Flight (ToF) based sensor, such as a laser distance finder or ultrasonic ranger. In some examples, the autofluorescence load sensing device 100 may move (e.g., move to adjust the distance to the surface 210) based on the distance 208. The distance sensor, in some examples, may be moveable to determine distance from different surfaces in a space. In some examples where the contamination sensing device 100 is mounted permanently in place, the location of the contamination sensing device 100 may be calibrated prior to operation. The calibration may comprise, for example, the distance between the contamination sensing device 100 and the target surface(s) 210.

In some examples, the surface area that may be measured by the contamination sensing device 100 may depend on the emission angle of the excitation light 212 and the distance 208 between the contamination sensing device 100 and the target surface 210. In some examples, where an excitation light source 102 comprises LED(s), the emission angle of the excitation light 212 may be 180 degrees or less (e.g., 130 degrees). In some examples, the surface area of the target surface 210 measured by the contamination sensing device 100 may depend on a 3D distribution of the excitation light 212 and the distance 208 between the contamination sensing device 100 and the target surface 210. In some examples, the distribution of the excitation light 212 may be cosine or Gaussian. In some examples, the surface area of the target surface 210 that may be measured by the contamination sensing device 100 may depend on a field of view of the camera/sensor(s) 104 of the contamination sensing device 100 and the distance 208 between the contamination sensing device 100 and the target surface 210. In some examples, the field of view of a camera may be 360 degrees. Spherical cameras, for example, may be able to capture a 360 degree image. In some examples, the field of view of a camera may be less than 360 degrees. The sensor(s) 104 may be capable of moving to cover a greater surface area (e.g., panoramic imaging). For example, the sensor(s) 104 may be capable of moving via the adjustable arm 206 and/or the track system 302. In some examples where the sensor(s) 104 is a photodiode or an array of photodiodes, the surface area of the target surface 210 that may be measured by the contamination sensing device 100 may depend on the field of view of the photodiode(s) and/or the distance 208 between the contamination sensing device 100 and the target surface 210. Photodiodes may be less sensitive to detecting wavelengths as the angle of the emitted light 214 changes from a line directly into the photodiode. The field of view may be measured by an angle of half sensitivity (e.g., the angle at which the photodiode detects half of the emitted light 214). In some examples, a photodiode may have a narrow field of view (e.g., an angle of half sensitivity of 15-20 degrees). In some examples, a photodiode may have a wide field of view (e.g., an angle of half sensitivity of 50-65 degrees).

Figure 12:
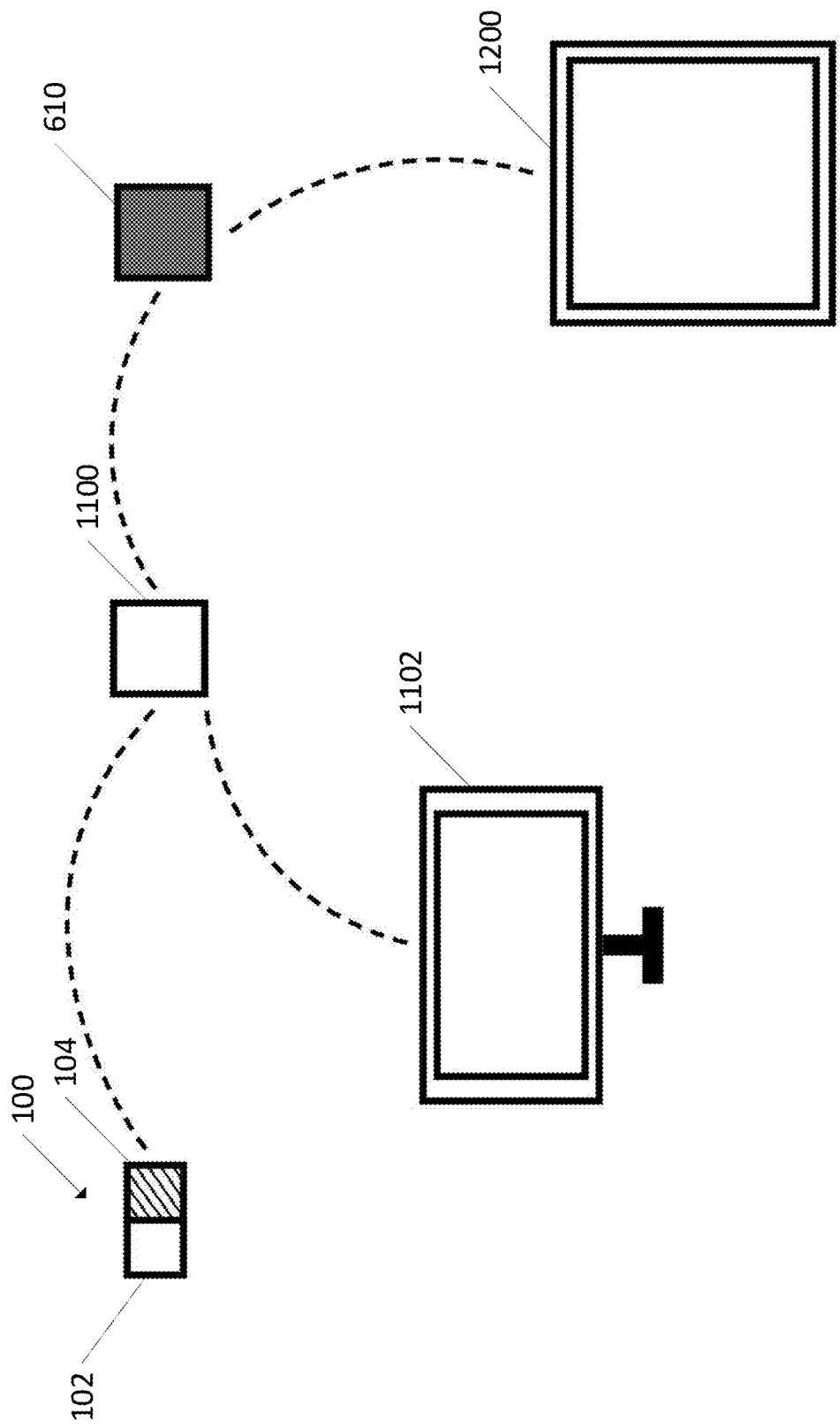
FIG. 12 illustrates an example system comprising a contamination sensing device and control system.

In some examples, the contamination sensing device 100 may determine coordinates of a bacterial load on the target surface 210 (e.g., (x,y) coordinates). The contamination sensing device 100 may set a (0,0) coordinate point (e.g., virtual coordinate point) on the target surface 210 and use the coordinate point to determine relative location(s) of surface bacterial load. The contamination sensing device 100 may determine a multitude of (x,y) coordinate points to map the location of bacterial load. In some examples, the contamination sensing device 100 may determine various representative functions (e.g., lines or circles) to map the location of bacterial load. In some examples, the bacterial load coordinates or representative function information may be used in a process of creating a contamination map. In some examples, the contamination map (and associated bacterial load coordinates or representative function information) may be used with a disinfecting lighting system, as shown in FIG. 12 (e.g., disinfecting lighting system 1200), to direct, via a control system/controller or processor, disinfecting light to increase/decrease/locate areas of contamination. In some examples, the contamination sensing device 100 may incorporate a laser. In some examples, an algorithm may calculate a centroid of the bacterial load by locating high areas of bacterial load that measure above a threshold value. In some examples, the threshold value may comprise a predetermined threshold value. In some examples, the threshold value may be calculated by the contamination sensing device 100. In some examples, the threshold value may be determined based on historical bacterial load data. Based on the location of the calculated centroid of the bacterial load, the contamination sensing device 100 may direct the laser to point at the location of the centroid. The contamination sensing device 100 may direct the laser to step/move through the target surface 210 area from highest level of bacterial load to lowest level of bacterial load above the threshold value. The laser may be used as an inspection and/or training tool. The laser may be used to indicate high risk surface areas for targeted cleaning (e.g., used by staff to target cleaning to high risk surface areas).

In some examples, the contamination sensing device 100 may use a series of excitation light source(s) 102 with different output wavelengths for excitation. The contamination sensing device 100 may use a series of sensor(s) 104 with different wavelength filters to detect fluorescence emissions. The use of different series of excitation light source(s) 102 and sensor(s) 104 may allow different types of microorganisms/bacteria to be characterized by determining which excitation spectra the bacteria respond to.

FIGS. 4A-6B illustrate various example configurations of excitation light source(s) 102, sensor(s) 104, control systems, and objects. In some examples, a physical enclosure may house the contamination sensing device 100 and/or components (e.g., light source(s) 102, sensor(s) 104) of the contamination sensing device 100. In some examples, the volume of the physical enclosure may be 4000 cm$^3$. In some examples, the volume of the physical enclosure may be less than or greater than 4000 cm$^3$. Objects may be put within a small enclosure (e.g. a cell phone) and measurements may be taken on the object within the enclosure.

Figure 4A:
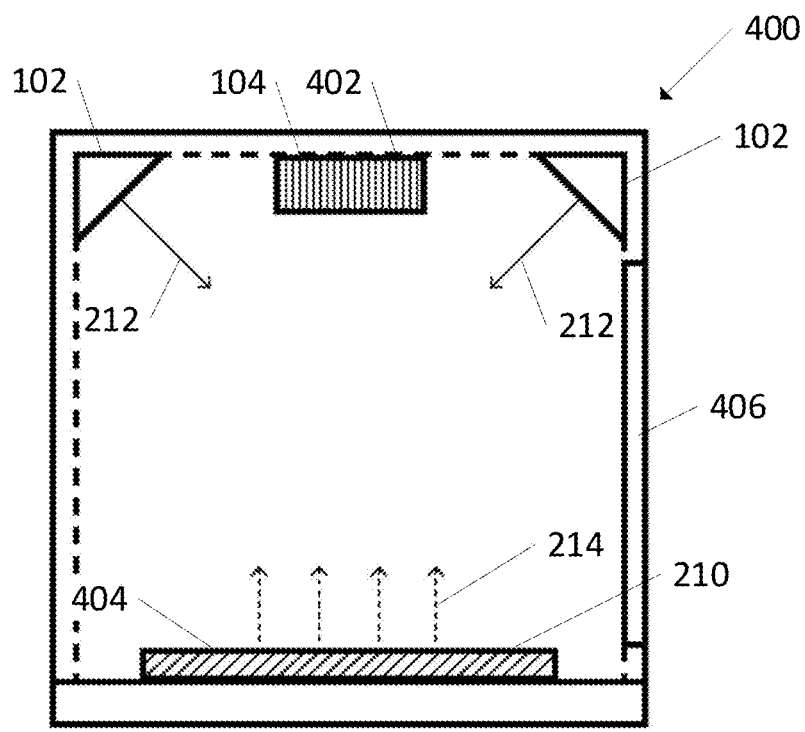
FIGS. 4A-4B illustrate an example enclosure with an contamination sensing device.
Figure 4B:
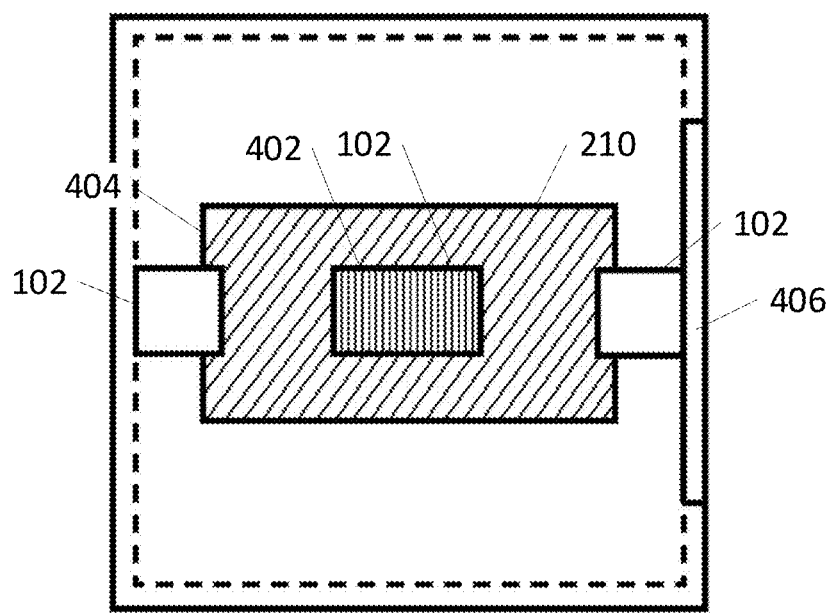

FIG. 4A shows a side/cross-sectional view of an example enclosure 400 integrated with a contamination sensing device 100 comprising the excitation light source(s) 102 and sensor(s) 104. The sensor(s) 104 of the autofluorescence bacterial load sending device 100, as shown in FIG. 4A, may, for example, comprise a camera sensor 402. The autofluorescence bacterial load sensing device 100 may comprise excitation light source(s) 102 mounted remote from the camera sensor 402. The excitation light source(s) 102 may be mounted, for example in the corners of the enclosure 400, at the edges of the enclosure, on the ceiling of the enclosure 400, and/or on the walls of the enclosure 400. The autofluorescence bacterial load sending device 100, as shown in FIG. 4A, may comprise two excitation light source(s) 102. In some examples, more than two excitation light source(s) 102 may be used. An object 404 comprising the target surface 210 may be located inside the enclosure 400. In some examples, the enclosure 400 may comprise a room with a door 406. The excitation light source(s) 102 may emit excitation light 212 towards an object 404 comprising the target surface 210. Emitted light 214 (e.g., emitted fluorescence) from the target surface 210 may be captured by the camera sensor 402. FIG. 4B shows a top view of the example enclosure 400 integrated with the contamination sensing device 100 of FIG. 4A.

Figure 5A:
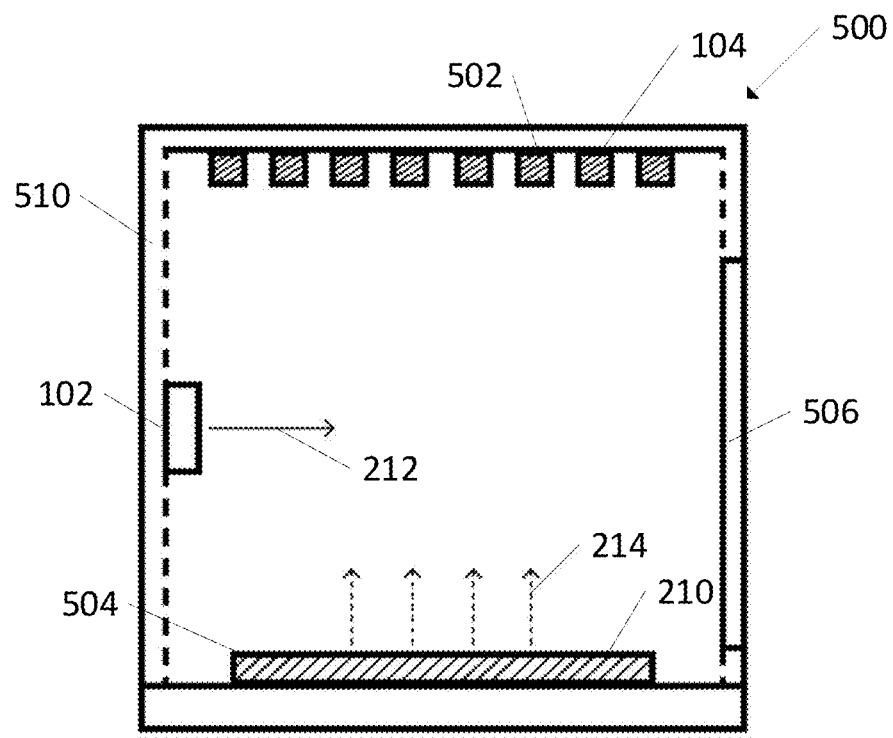
FIGS. 5A-5B illustrate an example enclosure with an contamination sensing device with a photodiode array.
Figure 5B:
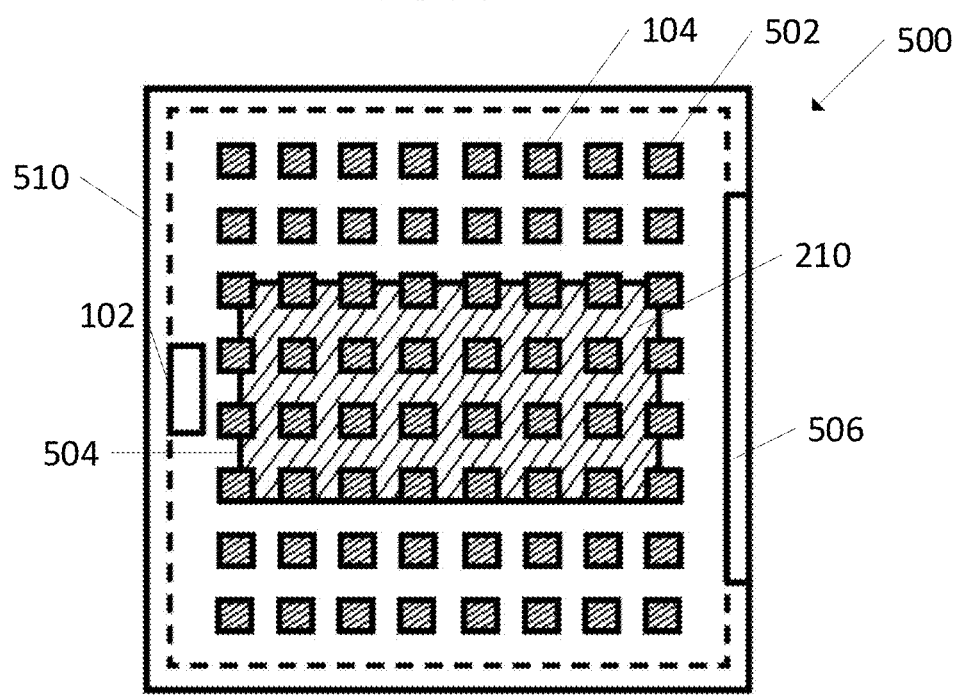

FIG. 5A shows a side/cross-sectional view of an example enclosure 500 integrated with a contamination sensing device 100. The sensor(s) 104 of the autofluorescence bacterial load sending device 100, as shown in FIG. 5A, may be a photodiode based sensor comprising, for example, an 8×8 photodiode array 502. An object 504 comprising the target surface 210 may be located inside the example enclosure 500. In some examples, the enclosure 500 may comprise a room with a door 506. The excitation light source(s) 102 may emit excitation light 212 towards the target surface 210. In some examples, as shown in FIG. 5A, the excitation light source(s) 102 may be mounted to and/or located on a wall 510. Emitted light 214 (e.g., emitted fluorescence) may be captured by the photodiode array 502 and from the target surface 210. FIG. 5B shows a top view of the example enclosure 500 integrated with the contamination sensing device 100 of FIG. 5A.

Figure 6A:
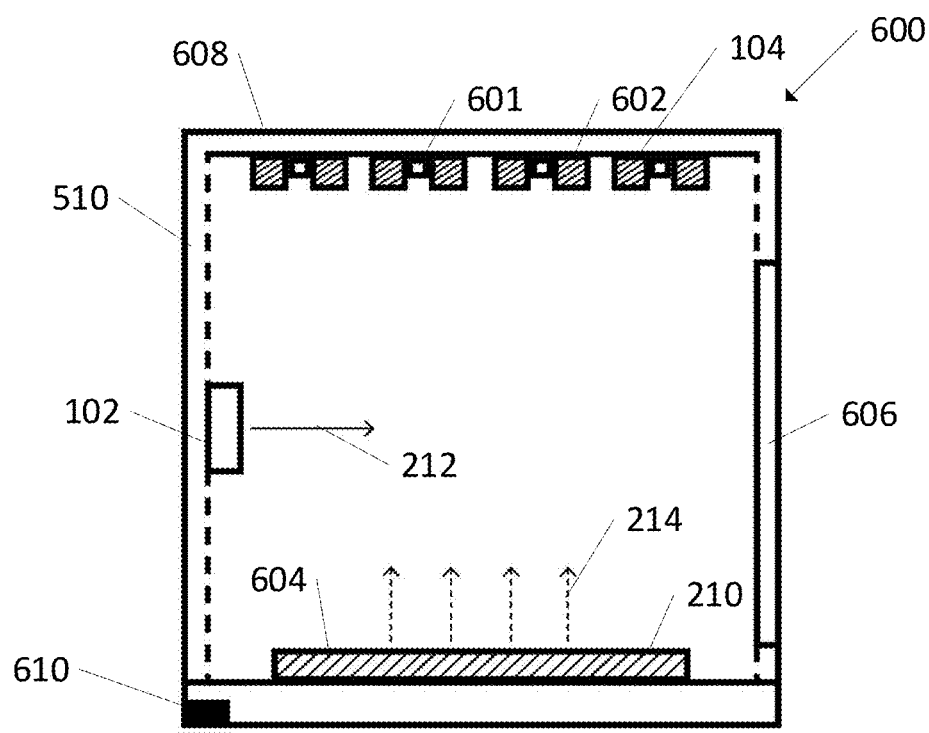
FIGS. 6A-6B illustrate an example enclosure with an contamination sensing device with a photodiode array and a lighting element array.

FIG. 6A shows a side view of an example enclosure 600 integrated with a contamination sensing device 100. The light source(s) 102 of the autofluorescence bacterial sensing device 100 may, for example, be mounted to and/or located on/near a wall 510. The enclosure 600 may comprise an array of lighting element(s) 601 (e.g., LEDs) able to emit disinfecting light (e.g., light within a range of 380-420 nm). Disinfecting light may, for example, comprise a wavelength in a range of 380 to 420 nm, e.g., 405 nm, and may reduce the presence of contamination such as bacteria. The 380 to 420 nm wavelengths of light may inactivate microorganisms such as but not limited to: *Escherichia coli* (*E. coli*), *Salmonella*, Methicillin-resistant *Staphylococcus aureus* (MRSA), *Clostridium difficile*, and a wide variety of yeasts and/or fungi. In some examples, disinfecting light includes light with a disinfecting dosage sufficient to stop, decrease, impede, or eliminate bacteria and/or bacteria population growth. In some examples, the disinfecting dosage may be characterized in terms of irradiance or with units such as, for example, milliwatts per centimeter squared (mW/cm$^2$). In some examples, the disinfecting dosage may have a minimum irradiance threshold at or around 0.01 mW/cm$^2$. In some examples, the disinfecting dosage may be characterized in terms of radiant exposure with units such as, for example, Joules per centimeter squared (J/cm$^2$).

In some examples, disinfecting light may have an irradiance of at least 0.01 or 0.02 mW/cm$^2$, e.g., from lighting element(s) 601. Disinfecting light may have any color desired, so long as sufficient light to disinfect in the 380 to 420 nm range is present therein. Disinfecting light may be solely between 380 to 420 nm wavelength light. In some examples, disinfecting light may include or be converted to include at least one additional portion of light above 420 nm to create disinfecting light of another color, such as white light.

The lighting element(s) 601 able to emit disinfecting light may, for example, be mounted/attached to the ceiling 608 of the enclosure 600. The enclosure 600 may comprise a photodiode array 602 as part of the contamination sensing device 100. The photodiode array may, for example, be mounted/attached to the ceiling 608 of the enclosure 600. An object 604 comprising the target surface 210 may be located inside the enclosure 600. In some examples, the enclosure 600 may comprise a door 606. The light source(s) 102 may emit excitation light 212 towards the target surface 210. Emitted light 214 (e.g., emitted fluorescence) from the target surface 210 may be captured by the photodiode array 602. The contamination sensing device may use the excitation light 212 to determine bacterial load. The lighting element(s) 601 may, based on the bacterial load, emit disinfecting light to inactivate bacteria/microorganisms. In some examples, the lighting element(s) 601 may emit disinfecting light based on the bacterial load exceeding a threshold bacterial load.

Figure 6B:
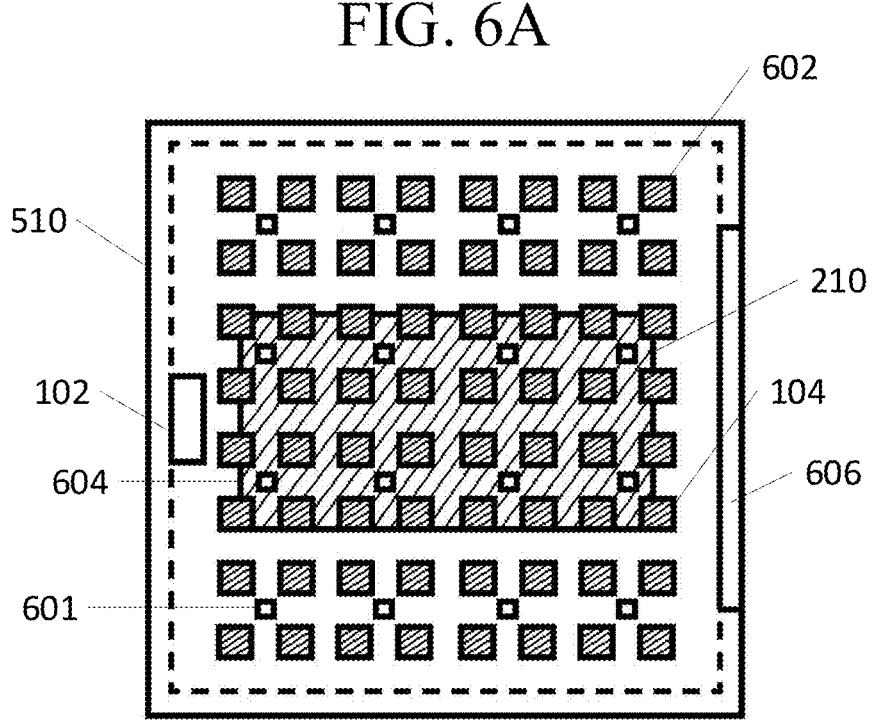

FIG. 6B shows a top view of the example enclosure 600 integrated with the contamination sensing device 100 of FIG. 6A.

The enclosures 400, 500, 600 may be openable or closeable via, e.g., hinged or sliding doors 406, 506, 606. In some examples, the enclosures 400, 500, 600 may be approximately opaque to keep the excitation light 212 within the enclosure 400, 500, 600. The enclosures 400, 500, 600 may comprise a control system (e.g., controller) 610 for controlling the contamination sensing device 100 and/or the lighting elements 601 able to emit disinfecting light. The enclosures 400, 500, 600 may be of any dimension. In some examples, the enclosures 400, 500, 600 may be relatively small (e.g., 12 inches by 12 inches or smaller) and be able to contain individual items. In some examples, the enclosures 400, 500, 600, may be large (e.g., an entire room). In some examples, the excitation light source(s) 102 may be mounted at a 90 degree angle from the sensor(s) 104 as shown in FIGS. 5A-6B. In some examples, the sensor(s) 104 may be mounted at the top of the enclosure and substantially or directly above the target surface 210 as shown in FIGS. 4A-6B.

The contamination sensing device 100 may be integrated directly into another device or appliance (e.g., an add-on in a disinfecting lighting fixture or inside a refrigerator). The contamination sensing device 100, for example, may be powered through line power, through another device/appliance's low voltage power, power outlets, electrical power supplies, batteries or rechargeable batteries mounted in proximity to the appliance, and/or though wireless or inductive charging. Where rechargeable batteries are employed, they may be recharged, for example, using alternating current power and/or solar panels (not shown).

Figure 7:
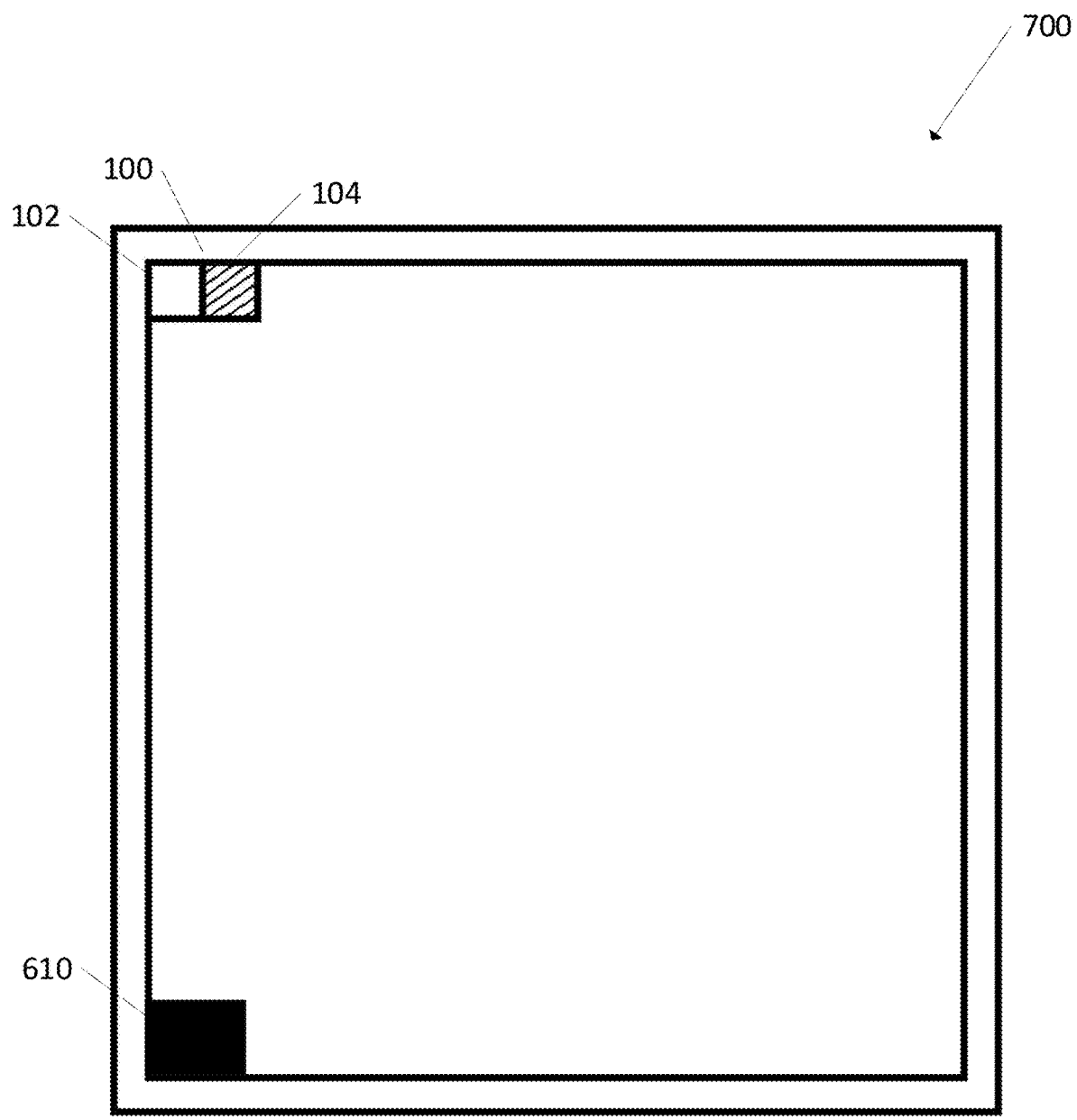
FIG. 7 illustrates an example contamination sensing device and a disinfecting light fixture.

In some examples, as shown in FIG. 7, the contamination sensing device 100 may be integrated into a disinfecting light fixture 700. The disinfecting light fixture 700, for example, may be an overhead lighting fixture or task light. The disinfecting light fixture may emit disinfecting light which may, for example, comprise a wavelength in a range of 380 to 420 nm, e.g., 405 nm, and may reduce the presence of contamination such as bacteria. The disinfecting light fixture 700 and bacterial load sensing device 100 may be in communication with each other through a control system 610 (e.g., controller) to allow for the data from the sensor(s) 104 to be used in the decision making process for controlling the output of the disinfecting light fixture 700. In some examples, the control system 610 may adjust the output of the disinfecting light based on data from the sensor(s) 104. In some examples, the control system 610 may adjust the irradiance of the disinfecting light emitted by the disinfecting light fixture, for example, based on the data from the sensor(s) 104. In some examples, the control system 610, based on the data from the sensor(s) 104 of the contamination sensing device 100, may adjust the amount of time the disinfecting light fixture 700 emits the disinfecting light. FIG. 7 provides an example where the contamination sensing device 100 is physically coupled to a disinfecting lighting fixture 700 (e.g., a troffer fixture). In some examples, the contamination sensing device 100 may not need to be physically coupled to a disinfecting light fixture 700 and/or system to be in communication with the disinfecting light fixture 700 and/or system. In some examples, the contamination sensing device 100 may be separate from the disinfecting light fixture 700 and/or system. In some examples, the contamination sensing device 100 may be in wireless communication with the disinfecting light fixture, for example, through the control system 610.

Figure 8:
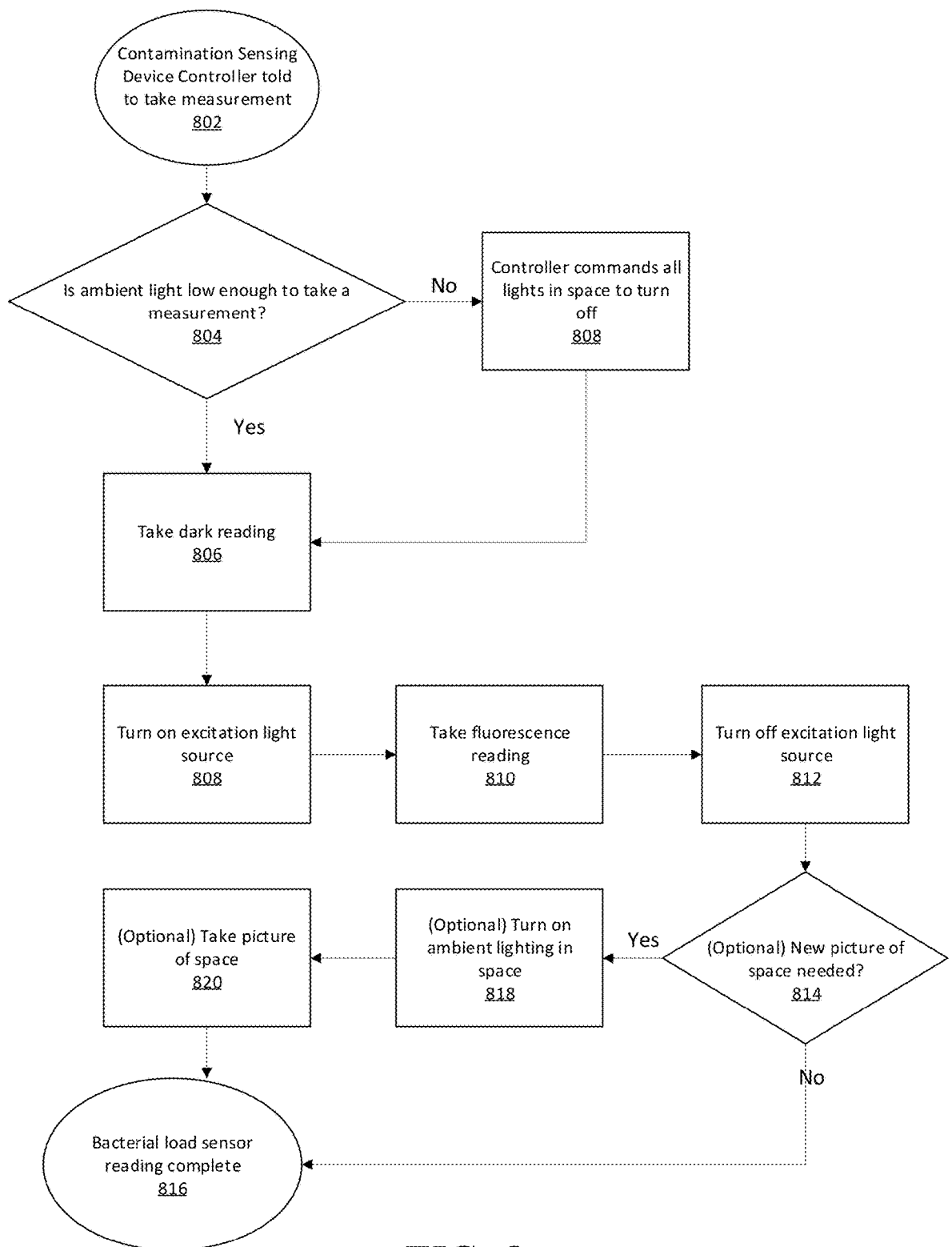
FIG. 8 illustrates an example process for using an contamination sensing device.

A flowchart showing an example process 800 for taking a measurement using a contamination sensing device 100 is illustrated in FIG. 8. The control system 610 of the contamination sensing device 100 may receive an instruction to take a measurement of the environment at step 802. In some examples, the environment may be preferred to be dark or otherwise not fully illuminated for the contamination sensing device 100 to work most effectively. In some examples, the sensor(s) 104 may capture an optional dark image. A dark image may be obtained, for example, by taking an image with the excitation light source(s) 102 turned off. The contamination sensing device 100 may determine, using the sensor(s) 104, if the ambient light in the environment is low enough to take a measurement at step 804 (e.g., determine if the amount of ambient light is below a light threshold). If the ambient light in the environment is low enough to take a measurement (step 804: YES), the contamination sensing device 100 may take a measurement at step 806. If the ambient light in the environment is not low enough to take a measurement (step 804: NO), the control system 610 may turn off all lights in the environment (e.g., excitation light source(s) 102, ambient lighting, etc.) at step 808. The contamination sensing device 100 may then take a measurement, with the lights off, at step 806.

The control system 610 may turn on the excitation light source(s) 102 at step 808. The excitation light source(s) 102 may flash the excitation light 212 at high power for a short amount of time (e.g., 1 microsecond to 3 seconds) to initiate autofluorescence. During emission of the excitation wavelength, the sensor(s) 104 may capture the fluorescence image data at step 810. The excitation light source(s) 102 may turn off after the sensor(s) 104 captures the fluorescence image data at step 812. In some examples, the excitation light source(s) 102 may turn off before the sensor(s) 104 captures the fluorescence image data. The control system 610 may determine if a new picture of the environment is needed at step 814. A new picture of the environment may be needed, for example, if the surface/environment has changed. If a new picture of the environment is not needed (step 814: NO), the bacterial load sensor reading is complete at step 816. If a new picture of the environment is needed (step 814: YES), the control system 610 may turn on ambient lighting in the environment at step 818. The control system 610 may take a picture of the environment at step 820. In some examples, the control system 610 may take a picture to determine if the surface/environment has changed. If the surface/environment has changed, the control system 610 may save the new picture of the environment, for example, to create a composite image. The sensor(s) 104 and/or a secondary/additional sensor (e.g., a camera) may capture the image of the space using white light illumination of the space or by optionally using a flash of visible or infrared (IR) light to illuminate the space. After taking the picture of the environment, the bacterial load sensor reading may be complete at step 816.

Figure 9:
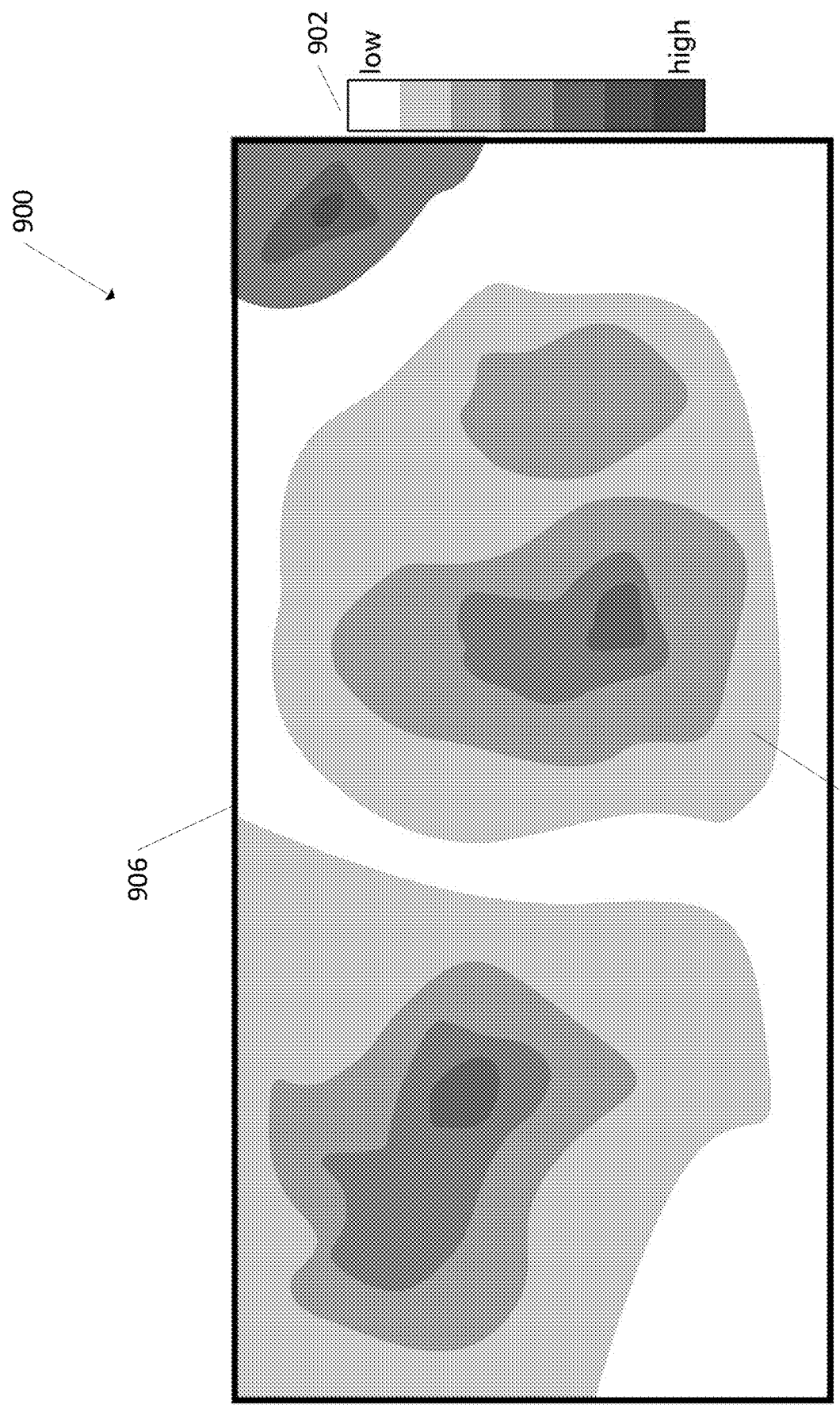
FIG. 9 illustrates an example contamination map showing levels of contamination load.

Using the data collected by the sensor(s) 104, the contamination sensing device 100 may create an image(s) showing contamination (e.g., bacteria) hotspots, referred to in this disclosure as a contamination map. In some examples, the contamination map may comprise a picture of the space taken by a regular camera as an overlay. In some examples, an additional regular color (visible light), grayscale, or infrared (IR) camera may be used in conjunction with the sensor(s) 104 to generate a room/enclosure image. The room/enclosure image may be overlaid with the contamination map to create a composite image, similar in appearance to images produced by high-end thermal cameras, similar to, for example, a heat map or a contour map. FIG. 9 shows an example contamination map 900 image with a key 902 to read the levels of bacterial load 904 or concentration of bacterial load 904 on a surface 906. Bacterial load 904 may be indicated by certain colors within the contamination map 900 and defined by the key 902.

Changes in surface bacterial load detected by the contamination sensing device 100 may be determined through a variety of methods. The contamination map 900 indicating the location and quantity of bacteria may be provided by the contamination sensing device 100. The contamination map 900 of microorganism/bacteria may show the locations of microorganisms/bacteria on a surface and use colors with a key 902, for example, to denote the density/concentration of bacteria in those locations. The key 902 may include a correlated number scale, a 'low' to 'high' scale, or more specific measurements of bacteria concentrations.

Figure 10:
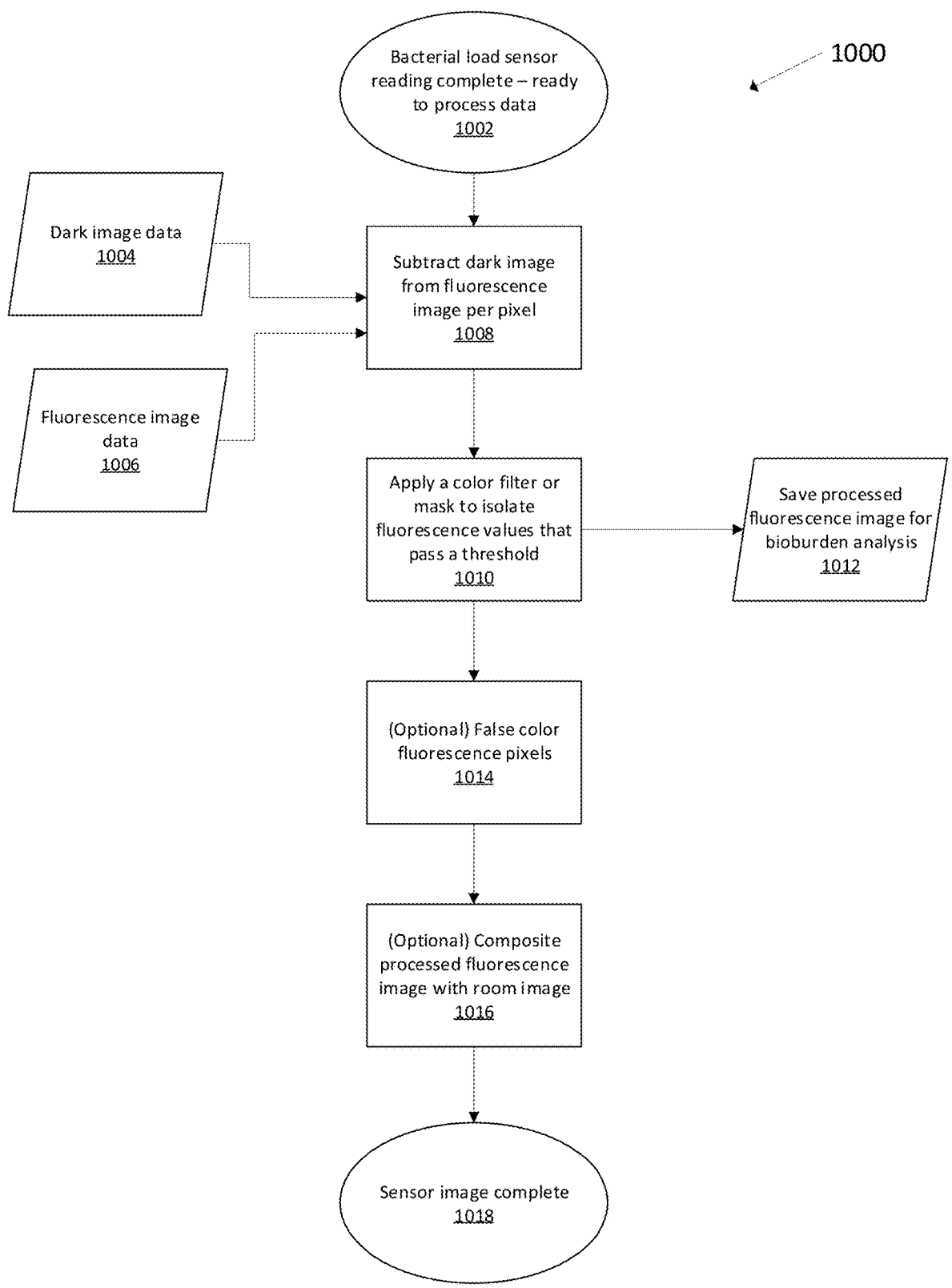
FIG. 10 illustrates a flow chart for an example contamination sensing device creating a bacterial load image.

FIG. 10 shows an example flowchart of an example process 1000 for making a sensor image and/or contamination map 900 from the sensor data. The contamination sensing device 100 may perform computer vision processing, for example, to filter out noise, highlight microorganisms in the image, or count and locate microorganisms. Once a dark image, fluorescence image, and/or room image are taken, computer vision algorithms may be used to create a final image (e.g., contamination map 900). The following is an example procedure to arrive at the final image. The contamination sensing device 100 may obtain a microorganism/bacterial load sensor reading (e.g., fluorescence image data) from the sensor(s) 104 and the data may be ready for processing at step 1002. In some examples, dark image data 1004 from the dark image may be subtracted from fluorescence image data 1006 from the fluorescence image at step 1008, for example, to reduce noise from ambient light or the sensor(s) 104. In some examples, a color filter and/or mask may be used to isolate colors above a certain threshold at step 1010. In some examples, an edge detection algorithm may be used to further isolate concentrations of colors at step 1010. The computer may save this processed image for use in determining bacterial load (e.g., performing bioburden analysis) at step 1012. In some examples, the remaining steps may make the image easier to interpret. In some examples, false coloring may be added for image clarity by mapping different intensities of a single color or a greyscale range to a range of colors at step 1014. The addition of false coloring may, for example, be useful for photodiode sensor(s) which may only output intensity values per sensor, instead of a colored pixel. In some examples, an algorithm may create a composite image by processing fluorescence image data 1006 and the room image together at step 1016 Creation of the composite image may be performed, for example, by addition or weighted blending with transparencies. The sensor image may be complete at step 1018.

The contamination sensing device 100 may be standalone, or part of a mesh network of devices (e.g., connected to other sensor(s) 104, lights, and controls). The contamination sensing device 100 may connect, over a local intranet or over the internet, to a server and send instructions/data (e.g., raw or processed data) to the server and/or receive instructions/data from the server. The server may comprise one or more servers, may be connected to several devices, and/or may relay commands between these servers and/or devices. When both the contamination sensing device 100 and a lighting system are connected to the same network (e.g., mesh network or server network), the contamination sensing device 100 may send instructions, such as, for example, to turn the lighting system off (e.g., to reduce the amount of ambient light in the space) while taking a bacterial load reading.

Figure 11:
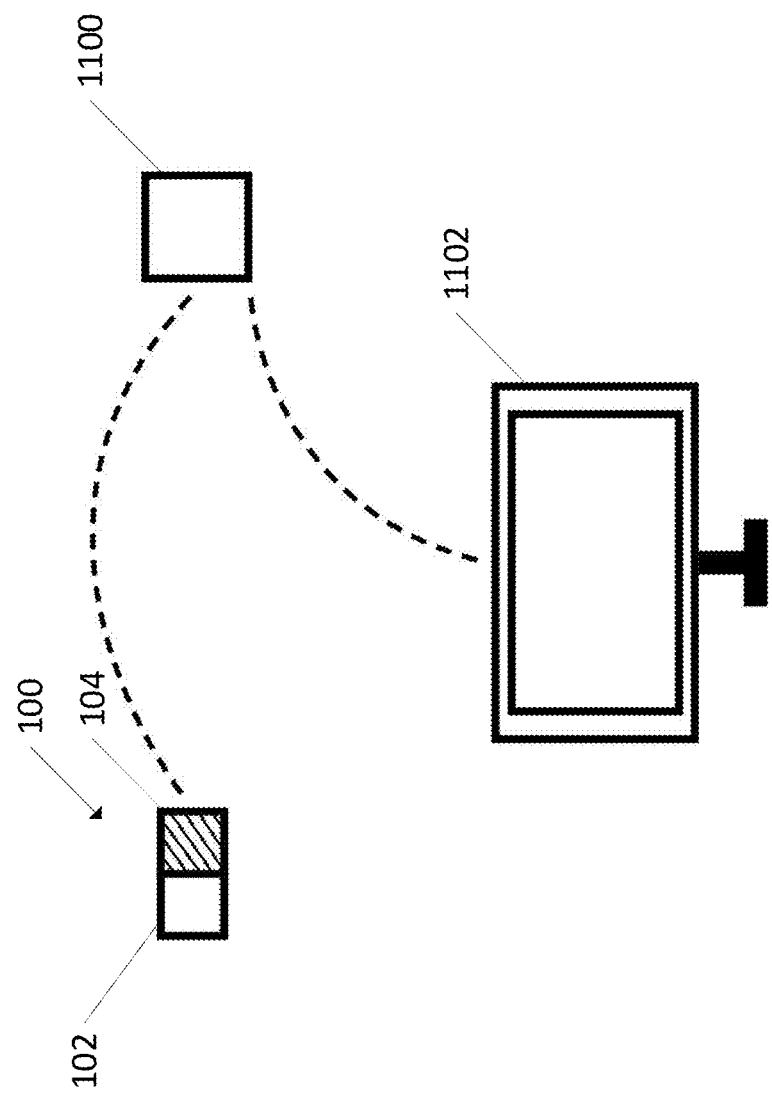
FIG. 11 illustrates an example system comprising a contamination sensing device, processor, and user interface.

FIG. 11 illustrates an example contamination sensing device 100 in communication with a processor 1100 (e.g., processor capable of computer vision algorithms) and a user interface 1102 (e.g., interface to display data). The contamination sensing device 100 may make use of processors 1100 such as, for example, central processing units (CPU), application specific processors (APU), graphics processing units (GPU), or digital signal processor (DSP) to process data. The contamination sensing device 100 may have wireless antennas and/or chips for Bluetooth (BLE), Wi-Fi, long or short-range radio, and/or cellular connections. Components of the contamination sensing device 100 (e.g., excitation light source(s) 102, sensor(s) 104, control system 602, etc.) may be electrically connected and/or may be wirelessly connected via the wireless antennas and/or chips. The contamination sensing device 100 may have memory and/or storage for holding instructions/data. The contamination sensing device 100 may contain a System on a Chip (SoC) that may incorporate some or all of the aforementioned functionality.

FIG. 12 shows a contamination sensing device 100 in communication with a control system 610 and a disinfecting lighting system 1200. The contamination sensing device 1200 may be in communication with the processor 1100. The processor 1100 may provide communication with the user interface 1102, control system 610, and/or disinfecting lighting system 1200. As further described herein, the functions of processor 1100 of FIG. 11 or 12 or the control system 610 of FIG. 12 may be implemented by the processor 2201 of example computing device 2200 of FIG. 22.

A contamination map/composite image, such as, for example, a composite image created using the process shown in FIG. 10, may show high risk areas in a real space and may allow for deployment of cleaning personnel to those specific areas. The composite image may be processed by computer vision algorithms, allowing a computer to decide where the high risk areas may be in a space. The processed data may, for example, be used by a disinfecting lighting system 1200. The disinfecting lighting system 1200 may emit disinfecting light. Disinfecting light may, for example, comprise a wavelength in a range of 380 to 420 nm, e.g., 405 nm, and may reduce the presence of contamination such as bacteria. Using the processed data, the disinfecting lighting system 1200 may increase the dosage in the effected room, space, or zone, with the intention of reducing the bacterial load in the high risk area(s). In some examples, the control system 610 may determine, based on the processed data, that a surface is contaminated (e.g., the bacterial load exceeds a bacterial load threshold). In some examples, the control system 610 may, based on the contamination of the surface, send instructions to the disinfecting lighting system 1200 to emit the disinfecting light. In some examples, the control system 610 may determine, based on the level of contamination sensed by the contamination sensing device 100, the dosage of disinfecting light. The disinfecting lighting system 1200 may, for example, adjust wavelengths of disinfecting light emitted, irradiance of the disinfecting light, the amount of time the disinfecting lighting system 1200 emits the disinfecting light, etc., based on the instructions from the control system 610. The processed data from the contamination sensing device, may indicate the location of contamination on a surface. The disinfecting lighting system 1200, may adjust the disinfecting light based on the location of the contamination. For example, the disinfecting lighting system 1200, may increase the dosage of disinfecting light for an area indicated as containing contamination by the contamination sensing device 100. Use of the processed data, for example, by the disinfecting lighting system 1200, may allow for automated reduction of bacterial load with minimal to no human intervention.

Figure 13:
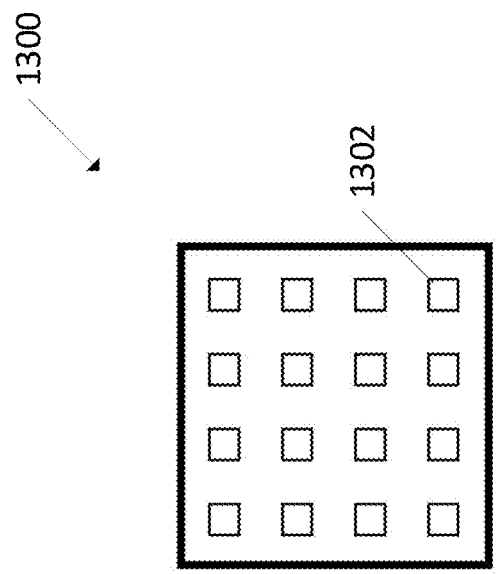
FIG. 13 illustrates an example two dimensional array of photodiodes.

In some examples, the sensor(s) 104 may be a single photodiode, an array of photodiodes, an array of Single Photon Avalanche Diodes (SPAD), and/or an optical phased array, with or without bandpass filters. FIG. 13 shows a front view of an array 1300 of photodiodes 1302. The array 1300 of photodiodes 1302 may be arranged in a grid pattern (e.g., 8×8, 32×32, 128×64, etc.). Each diode 1302 may be treated as a pixel and the grid may represent the total number of pixels in the generated image. Each pixel may contain an intensity value representing the amount of fluorescence detected. While most configurations may have far fewer pixels (e.g., 256 pixels compared to hundreds of thousands or more for a typical camera), each diode 1302 may be more sensitive than a typical camera pixel. Increased sensitivity may allow for better detection of different levels of intensity emitted from the bacteria.

Figure 14:
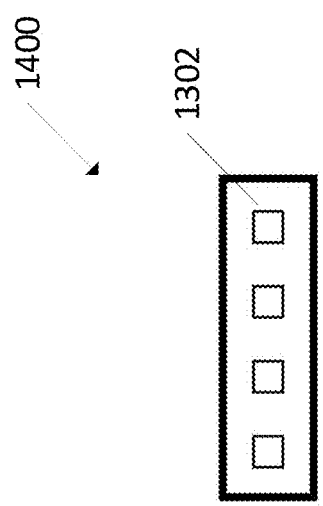
FIG. 14 illustrates an example one dimension array of photodiodes.

A 1D array 1400 (e.g., a line of sensor(s) 104, linear array of sensor(s) 104) may be used alternatively or in addition to a 2D array or grid of sensor(s) 104. FIG. 14 shows a front view of a 1D array 1400 of photodiodes 1302. A 1D array 1400 may allow the contamination sensing device 100 to scan along one axis. To measure along a second axis, the 1D array 1400 of sensor(s) 104 (e.g., photodiodes 1302 and/or multispectral sensors) may be coupled to a motor and/or servo, which may then be able to move/rotate the 1D array 1400 of sensor(s) 104 to take measurements along the second axis. In some examples, the 1D array 1400 of sensor(s) 104 may be coupled to an adjustable arm 206 and/or track system 302 to enable movement of the 1D array 1400 of sensor(s) 104. Each of the sensor(s) 104 in an array 1400 may, for example, be configured to detect a different wavelength. In some examples, the sensor(s) 104 in an array 1400 may comprise filters. In, some examples, the filters may be mounted to the sensor(s) 104 or otherwise disposed in the path of light entering the sensor(s) 104. In some example, each filter associated with each different sensor(s) 1400 in an array 1400 may block/reduce different wavelengths of light. In some examples, an array 1400 may be a group of sensor(s) 104. In some examples, the group of sensor(s) 104 may detect light having substantially the same wavelengths. In some examples, the group of sensor(s) 104 may detect light having substantially different wavelengths. In some examples, groups of sensor(s) 104 may any assortment of sensor(s) configured to detect substantially the same or different wavelengths.

In some examples, the sensor(s) 104 may comprise an array of multispectral sensors or spectrometers. In some examples, a multispectral sensor may comprise a plurality of photodiodes. Each photodiode may comprise a filter configured to reduce/block wavelengths of light. In some examples, each photodiode may comprise a different filter. Each different filter, for example, may reduce/block different wavelengths of light. In some examples, the multispectral sensor comprising a plurality of photodiodes and associated filters may measure wavelengths of light. In some examples, each photodiode may be configured to respond to a different wavelength or range of wavelengths.

Figure 15:
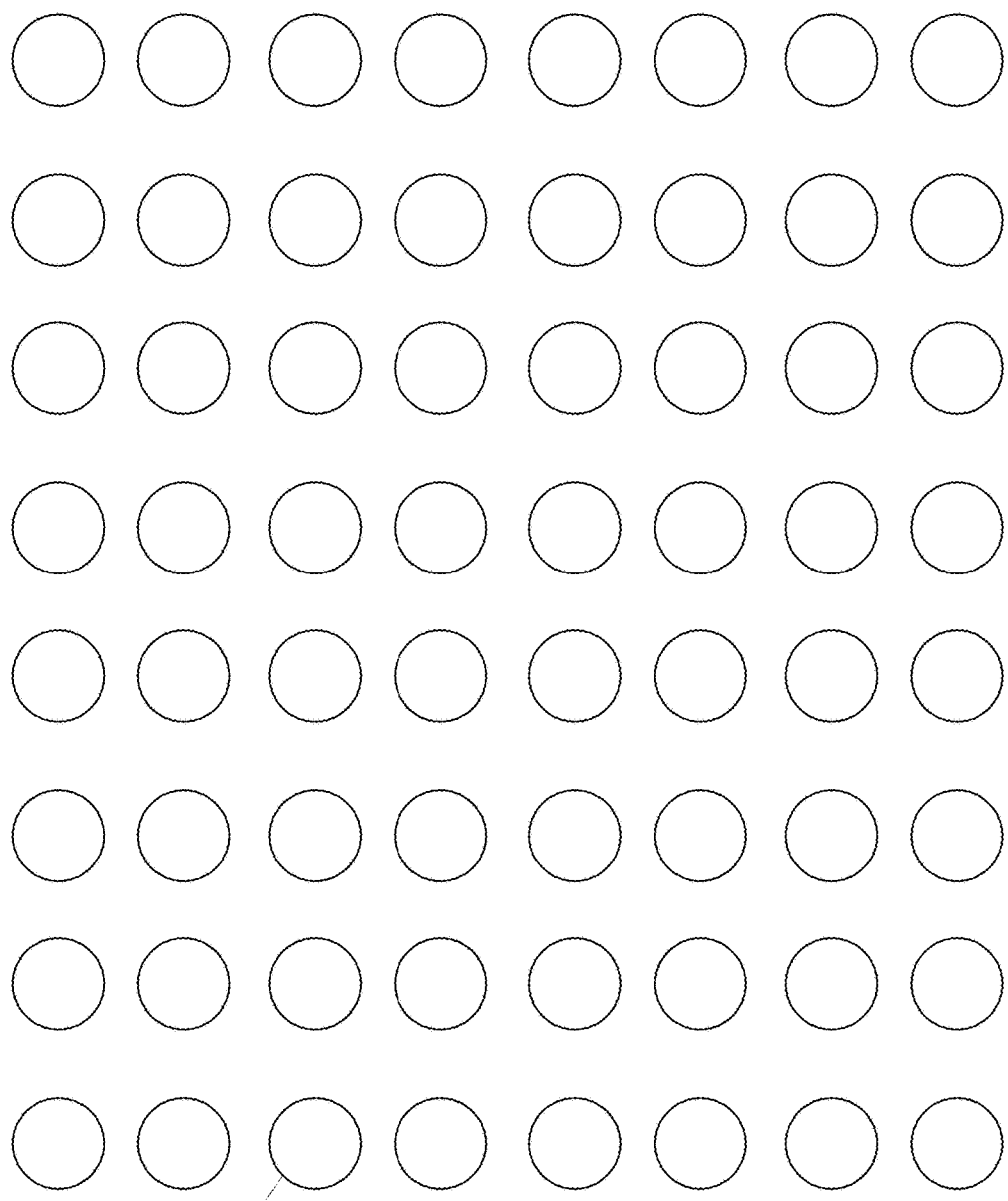
FIG. 15 illustrates an example array of pixels for a fluorescence image from a contamination sensing device.

FIG. 15 illustrates an image produced by example sensor arrays. These sensor arrays may be used to detect and measure fluorescence emission spectra across a range of wavelengths, with measurements in intensity per wavelength. Compared to a photodiode array, which measures overall intensity in a wavelength range, multispectral sensors or spectrometers may give a substantially higher resolution measurement of autofluorescence response. Each pixel in the contamination map generated by the multispectral sensors or spectrometers may consist of a spectral power distribution (SPD), which contains intensity per wavelength of each wavelength measured.

FIG. 15 shows an example composition of fluorescence image 1500 from the sensor(s) 104. The sensor(s) 104 may be, for example, a camera sensor, photodiode sensor(s), and/or multispectral/spectrometer sensor(s). The fluorescence image 1500 may comprise an array of pixels 1502. The number of pixels 1502 in the array of pixels 1502 may vary, for example, based on the resolution and/or number of sensor(s) 104. In some examples, each pixel 1502 may correspond to one sensor 104. In some examples, each pixel 1502 may correspond to multiple sensor(s) 104. In some examples, each pixel may represent data from a single sensor performing multiple measurements with different filters. In some examples, the resolution may be based on the resolution of a camera sensor. In some examples, the resolution may be based on the number of photodiode sensors and/or multispectral/spectrometer sensors. The fluorescence image 1500 shown in FIG. 15 comprises an 8×8 array of pixels 1502. In some examples, the number of pixels could be much higher (e.g., 1024×1024 or higher). Each pixel 1502 in the array of pixels 1502 may comprise a value indicating a color intensity. Each pixel 1502 may have an intensity value. In some examples, each pixel 1502 may have an intensity value for each color, such as, for example, when a camera is used. For example, each pixel 1502 may comprise a separate color intensity value for each of red, green, and blue. In some examples, each pixel 1502 of the array of pixels 1502 may comprise an SPD measured by the multispectral/spectrometer sensor(s). In some examples, each pixel may correspond to a plurality of wavelengths.

Ambient light may contribute to background noise that may be observed by the sensor(s) 104. Background noise may be caused, for example, by lighting fixtures, natural sunlight (e.g., sunlight through a window), or other devices that generate light. In some examples, the excitation light source(s) 102 may provide background noise if the excitation light 212 is taken in by the sensor(s) 104. In some examples, the fluorescence signal from microorganisms on the target surface 210 may have a low irradiance. Background noise may be reduced to a lower irradiance than the fluorescence signal to detect the fluorescence signal. In some examples, the fluorescence signal may become indistinguishable from background noise. In some examples, there may be a maximum threshold of background lux or irradiance that the ambient light may optimally be below before a measurement is initiated. Bandpass and/or high-pass filters may be used on the sensor(s) 104 to filter out undesired wavelengths such that only wavelengths of interest are observed by the sensor(s) 104. In some examples, excitation light 212 may enter the sensor(s). A dichroic filter or cosine corrector, may only allow light to enter at certain angles, and may be used to keep stray excitation light 212 from entering the sensor(s) 104.

Figure 16:
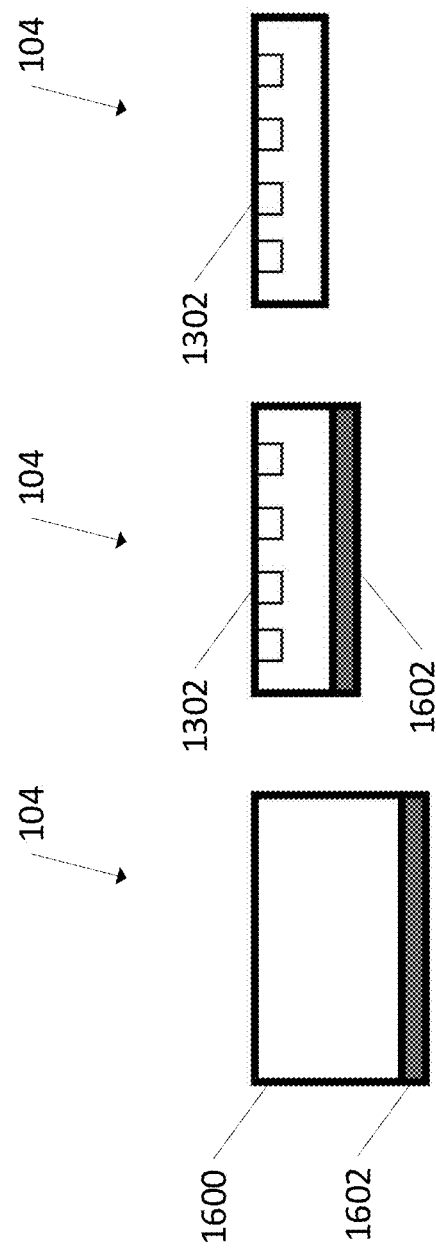
FIGS. 16A-16C illustrate sensors and/or filters for a contamination sensing device.

In some examples, the sensor(s) 104 may be a camera with a bandpass filter. FIG. 16A shows a sensor 104 comprising a camera 1600 with a bandpass filter 1602. In some examples, the bandpass filter 1602 may block/reduce wavelengths except those known to be emitted by the fluorescence of the target microorganisms. The camera 1600 may then only see the fluorescence of the microorganisms in a 2D field. The intensity of the observed colors and/or wavelengths may be used to determine relative quantity of bacteria and/or calibrated against a reference that corresponds to a known bacteria count (e.g., measured in CFU, to determine actual approximate quantity). FIG. 16B shows a sensor comprising an array of photodiodes 1302. The bandpass filter 1602 may block/reduce wavelengths except those known to be emitted by the fluorescence of the target microorganisms from reaching the photodiodes 1302. FIG. 16C shows an array of photodiodes 1302 without the bandpass filter 1602. In some examples, photodiodes 1302 may not have a bandpass filter 1602. In some examples, a filter adjuster may move the bandpass filter 1602 over the photodiodes as shown in FIG. 16B and adjustably remove the bandpass filter 1602 from covering the photodiode sensors 1302 as shown in FIG. 16C. The sensor(s) 104 (e.g., camera 1600, photodiodes 1302) may provide a detailed 2D contamination map of bacterial load, where each pixel represents the color, wavelength, and/or intensity of fluorescence. The map may be false-colored with bacteria density levels, for example, similar in appearance to an image one might get from a thermal camera.

In some examples, sensor(s) 104 may be produced or calibrated to respond to certain wavelengths of light, which may eliminate the need for a filter. In some examples, sensor(s) 104 may be calibrated to respond to a known wavelength that may autofluoresce from a target bacteria/microorganism. Calibration may be performed, for example, during an initial setup of the contamination sensing device 100. In some examples, calibration may be performed by the control system 602 before taking a measurement with the sensor(s) 104. In some examples, the control system 602 may adjust and/or change the calibration of the sensor(s), for example, based on an excitation wavelength, autofluorescence wavelength, In some examples, the sensor(s) 104 may be configured to receive light in the visible spectrum. In some examples, the sensor(s) 104 may be configured to receive near-ultraviolet, ultraviolet (UV), near-infrared, or infrared (IR) wavelengths. The sensor(s) 104 may have a filter and/or coating that blocks/reduces wavelengths not of interest and allows only the fluorescence of the microorganisms. In some examples, a plurality of filters may be used alone or in conjunction with each other.

In some examples, a filter and/or coating may be automatically or manually adjustable and/or removable. In some examples, excitation light may be detectable by the sensor(s) 104. The filter or coating may be adjusted to block/reduce excitation that may enter the sensor(s) 104. In some examples, the filter or coating may block/reduce all wavelengths except for wavelengths that may be emitted through autofluorescence of a target bacteria/microorganism. The contamination sensing device 100 (e.g., the control system 610) may adjust the filter or coating to determine the presence of a target bacteria. For example, the contamination sensing device 100 may emit an excitation light having a wavelength known to cause autofluorescence in a target bacteria towards the target surface 210. The sensor(s) 104 may comprise a filter or coating that may be adjusted to filter/reduce the excitation light from entering the sensor(s) 104. The filter or coating may, for example, be adjusted to block/reduce wavelengths that do not autofluoresce from the target bacteria, allowing wavelengths that fluoresce from the target bacteria to be detected by the sensor(s) 104.

The contamination sensing device 100 may detect contamination by detecting wavelengths of light that are known to be emitted by contamination in response to excitation wavelengths of light. The control system 610 may adjust the wavelengths of light emitted by the excitation light source to detect various types of contamination. The control system 610 may, for example, access a database to determine excitation and/or emission spectra of different types of contamination. The control system 610, based on the excitation spectra, may automatically adjust the wavelengths of light emitted by the excitation light source(s) 102. The control system 610 may, based on the excitation spectra and/or the emission spectra, automatically adjust the filter and/or coating to block reduce wavelengths of light. The control system 610 may cycle through various excitation and emission spectra to detect contamination.

In an example, the contamination sensing device 100 may emit an excitation light having wavelengths of about 230 nm and 280 nm, which are known to cause autofluorescence in tryptophan. The contamination sensing device 100 may adjust a filter and/or coating to block/reduce wavelengths of about 230 nm and 280 nm from the sensor(s) 104. The contamination sensing device 100 may adjust the filter or coating to block/reduce wavelengths outside of approximately 340 nm, which may be emitted through autofluorescence of tryptophan. The filter or coating, for example, may allow the autofluorescence of tryptophan at 340 nm to be detected by the sensor(s) 104. The contamination sensing device 100, based on the sensor(s) 104 detecting light of approximately 340 nm, may determine that a microorganism containing tryptophan is the target surface. The contamination sensing device 100 may adjust the filter and/or coating to block/reduce other wavelengths to detect contamination that does not contain tryptophan.

The contamination sensing device 100 may adjust the filter or coating, for example, with the control system 610. In some examples, the filter may be a physical filter. In some examples, the filter may be mounted to the sensor(s) 104. In some examples, the filter may be mounted in front of the sensor(s) 104. In some examples, the sensor(s) 104 may comprise the filter. In some examples, the filter may be a digital filter and may be applied by the control system 610.

In some examples, the contamination sensing device 100 may comprise multiple filters. The filters may, for example, comprise bandpass filters, dual bandpass filters, multi bandpass filters, high-pass filters, and/or low-pass filters. In some examples with a plurality of sensor(s) 104, each sensor(s) may comprise a filter. In some examples with a plurality of sensor(s) 104, each sensor(s) 104 may comprise a different filter configured to block/remove different wavelengths of light. In some examples, the contamination sensing device 100 may comprise a filter adjuster to dispose one or more filters in front of the sensor(s) 104. The filter adjuster may move a filter in front of the sensor(s) 104 to reduce/remove a wavelength (e.g., wavelength range) of light. In some examples, the contamination sensing device 100 may use the control system 610 to indicate, to the filter adjuster, which filter to use. The contamination sensing device 100 may change the filter used by the contamination sensing device 100 to determine the presence of a target bacteria. For example, the contamination sensing device 100 may emit an excitation light having a wavelength known to cause autofluorescence in a target bacteria towards the target surface 210. A filter may be used to filter/reduce the excitation light from entering the sensor(s) 104. The filter, in some examples, may be selected to block/reduce wavelengths that do not autofluoresce from the target bacteria, allowing wavelengths that autofluoresce from the target bacteria to be detected by the sensor(s) 104.

In some examples, the filter adjuster may comprise a plurality of filters on a wheel/disk. The filter adjuster may rotate the wheel/disk to move one of the plurality of filters in front of the sensor(s) 104. The filter adjuster may rotate, for example, using a motor or servomechanism. The control system 610 may rotate the wheel/disk to move the desired filter in front of the sensor(s) 104. The wheel/disk may comprise any number of filters. In some examples, the filter adjuster may comprise one or more filters on a hinge. The filter adjuster may, for example, move one or more of the hinged filters in front of the sensor(s) 104. In some examples, the filter mechanism may linearly move one or more filters into and/or out of the path of light directed toward the sensor(s) 104. In some examples, a first filter may be mounted over the sensor(s) 104 and the filter adjuster may be configured to move a second filter in front the sensor such that light directed toward the sensor passes through both the first filter and the second filter. In some examples, the first filter may be a high pass filter that filters excitation wavelength below, for example, 405 nm, and the second filter may be a lowpass filter that, in combined use with the first filter, results in a bandpass filter.

To detect contamination, the contamination sensing device 100 may emit wavelengths of light known to excite bacteria. For example, the contamination sensing device 100 may emit an excitation light having wavelengths of about 230 nm and 280 nm, which are known to cause autofluorescence in tryptophan. The contamination sensing device 100 may adjust a filter to block/reduce wavelengths of about 230 nm and 280 nm from the sensor(s) 104. The filters may be adjusted by a filter adjusting moving one or more filters in front of the sensor(s) 104. The contamination sensing device 100 may select a filter to block/reduce wavelengths outside of approximately 340 nm, which may be emitted through autofluorescence of tryptophan. The filter, for example, may be a bandpass filter with a 50 nm band, and may, for example, block/reduce wavelengths outside of 315-365 nm. The filter, for example, may allow the autofluorescence of tryptophan at 340 nm to be detected by the sensor(s) 104. The contamination sensing device 100, based on the sensor(s) 104 detecting light of approximately 340 nm, may determine that a microorganism containing tryptophan is the target surface. In some examples, the contamination sensing device 100 may use filters to block/reduce other wavelengths to detect contamination that autofluoresces at different wavelengths than tryptophan.

Example bandpass filters 1602 that may be utilized by the sensor(s) 104 may include dual-bandpass filters such as, for example: Edmund Optics #87-242 or Chroma 59009m, dual band FL filter (e.g., $\lambda_{emiss}$=500-550 nm and 590-690 nm). In some examples, a high-pass filter may be utilized instead of a bandpass filter 1602. FA high-pass filter may be used, for example, where it is known that the target space to be imaged has relatively low levels of autofluorescent light and IR in the wavelengths to be measured. The use of a high-pass filter may reduce system cost, for example, by reducing computational complexity and/or reducing the cost of sensor(s) 104 necessary for operation of the contamination sensing device 100.

In some examples, the sensor(s) 104 may comprise a camera. In some examples, the sensor(s) 104 may comprise an array of cameras. In some examples, a bandpass or dual-bandpass filter may be coupled to a camera to allow only wavelengths inside the bandpass ranges to pass into the camera. In some examples, each camera in an array of cameras may be correspond to a different filter to block/reduce different wavelengths. In some examples where each camera is coupled to a different filter, photos taken by each camera may show the wavelengths of light remaining after passing through the associated filter.

In some examples, a digital filter may be used instead of or in addition to physical filters. For example, the control system 610 may apply a digital filter to data provided by the sensor(s) 104. In some examples, the control system 610 may select from a number of programmed filters that may be, for example, high-pass filters, band-pass filters, and/or low-pass filters. In some examples, the control system 610 may generate and or adjust filters to be applied to the data from the sensor(s) 104. In some examples, the control system 610 may use digital filters to determine a contamination source. For example, a digital filter may be applied to data collected by the contamination sensing device 100 to determine if a target contamination source is present. In some examples, a digital filter may block/reduce wavelengths that are not known to be emitted from a target contamination source in response to excitation wavelengths. The digital filter, for example, may be used to determine that the measured emission wavelength may correspond to a specific contamination source. For example, contamination sources that contains pyoverdine may emit wavelengths of approximately 430 nm and 530 nm. To determine if a contamination source comprises pyoverdine, the control system 610 may, for example, use a digital filter to block/reduce wavelengths outside of approximately 430 nm and 530 nm.

In some examples, the contamination sensing device 100 may access a database comprising excitation spectra and autofluorescence spectra (e.g., emission spectra). The database may comprise excitation spectra and autofluorescence spectra, for example, for microorganisms, bacteria, and/or other organic material. In some examples, the database may comprise excitation spectra and autofluorescence spectra for surface materials which may comprise non-organic materials. In some examples, the database may comprise excitation spectra and autofluorescence spectra for cleaning products (e.g., cleaning product residue which may be left on a surface). The contamination sensing device 100 may use the excitation spectra and autofluorescence spectra from the database to determine a source of a wavelength emitted following an emission of excitation light.

Figure 17:
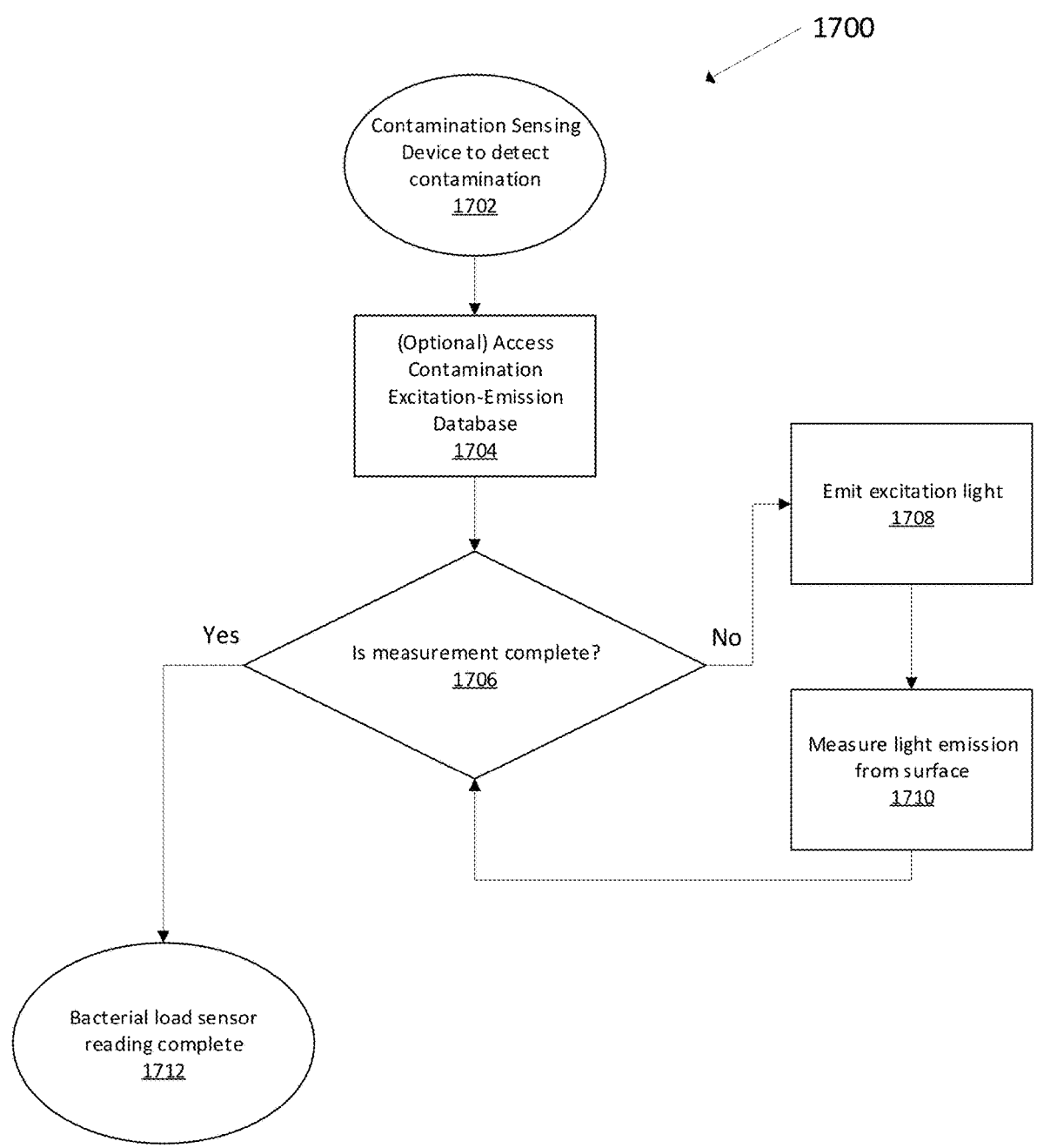
FIG. 17 illustrates a flow chart for using the example contamination sensing device to detect contamination.

FIG. 17 is a flowchart showing an example workflow 1700 for measuring bacterial load. The contamination sensing device 100 may determine to detect contamination beginning at step 1702. The contamination sensing device 100 may optionally access a contamination excitation-emission database at step 1704. The database may comprise excitation spectra and autofluorescence spectra for various contamination sources (e.g., bacteria). The database may comprise excitation and emission spectra that indicate, for a particular contamination source, the excitation wavelength that causes the contamination source to autofluoresce. In some examples, each type of contamination may have an associated emission spectra and excitation spectra. The contamination sensing device 100 may determine, at step 1706, if the measurement is complete. In some examples, the measurement may be complete if the contamination sensing device 100 took measurements for each contamination source in the database (e.g., emitted light corresponding to the excitation wavelength of each contamination source and measured light in the emission/autofluorescence wavelengths the associated contamination source). In some examples, the contamination sensing device 100 may only search for a portion of the contamination sources. For example, the contamination sensing device 100 may only look for common contamination sources, such as those corresponding to tryptophan and/or pyoverdine. In some examples, the measurement may be complete if the contamination sensing device 100 measures each emission wavelength at each excitation wavelength.

If the measurement is not complete (step 1706: NO), the contamination sensing device 100 may emit an excitation light corresponding to a specific contamination source at step 1708. If the contamination source is on the target surface, the contamination may autofluoresce in response to the excitation light. The contamination sensing device 100 may measure light from the surface at step 1710. For example, the contamination sensing device 100 may look for the emission wavelength corresponding to the contamination source at step 1708. In some examples, the wavelength emitted at step 1708 may comprise a wavelength or wavelength range of a number of predetermined wavelengths or wavelength ranges. The predetermined wavelengths or wavelength ranges may be wavelengths known to initiate autofluorescence in a target (e.g., contamination, bacteria, surface material, etc.). In some examples, the sensor(s) 104 may measure multiple light emission wavelengths at step 1710. In some examples with multiple sensors (104), the contamination sensing device 100 may measure multiple emission wavelengths in parallel (e.g., simultaneously). In some examples, the sensor(s) 104 may measure two or more wavelength ranges at once, such as, for example, by using a dual bandpass or multi bandpass filter. In some examples, where each sensor(s) 104 is associated with multiple filters, the contamination sensing device 100 may repeat step 1710 for each filter. After measuring the light emission from the surface, the contamination sensing device 100 may return to step 1706 to determine if the measurement is complete.

If the measurement is not complete (step 1706: NO), steps 1706-1710 may be repeated until all the contamination sources from the database have been tested (e.g., emitted the excitation wavelength and measured the emission wavelengths for each contamination source. In some examples, step 1708 and/or 1710 may be performed simultaneously by emitting multiple excitation wavelengths and measuring multiple emission wavelengths at approximately the same time. If the measurement is complete (e.g., all of the contamination sources have been tested or a requisite portion of the contamination sources have been tested) (step 1706: YES), the bacterial load sensor reading may be complete at step 1712. In some examples, the steps of workflow 1700 may be performed different orders than shown. In some examples, steps 1706-1710 may be performed using a programmed set of excitation and emission wavelengths, and step 1704 may be performed after steps 1706-1710 to process the results of steps 1706-1710. In some examples, the measured emission wavelengths and corresponding excitation wavelengths may be compared to the contamination database after and/or during steps 1706-1710.

In some examples, the contamination sensing device 100 may require calibration before use and/or periodically after an initial calibration. In some examples, calibration sensor readings may be used to filter out background noise (e.g., ambient light and/or object fluorescence). Reference swatches may be used to allow intensity calibration to known microorganism levels. For example, a plate of a known bacteria, bacteria type, and/or CFU count may be used as a reference swatch. A measurement swatch (e.g., an object with known size) may be used to calibrate the traditional visible light camera. Use of a measurement swatch may allow for pictures to be correlated to actual locations and distances in the space. In some examples, separating the background fluorescence from the microorganism fluorescence may comprise measuring the fluorescence of the surface after sterilization and removal of the sterilization product. The measurement after sterilization and removal of the sterilization product may be subtracted from the actual measurement (e.g., measurement of the surface and the bacterial load).

In some examples, for calibration, the contamination sensing device 100 may take measurements of the target surface 210 at several different excitation wavelengths to determine one or more excitation wavelengths that do not cause fluorescence of the background surface/target surface 210, but still cause fluorescence of at least some of the microorganisms.

In some examples, algorithms may be used to reduce noise in an image. Noise may be reduced, for example, by subtracting a calibration image from the captured image. In some examples, algorithms may be used to composite sensor data and camera data into a combined image. Data from several devices/sensor nodes in a space may be stitched together to form an image that represents an entire area, room, or floor, for example, of a building.

Computer vision algorithms may be used to check measurements for error caused by background noise. For example, if the majority of the surface being measured uniformly fluoresces at a certain intensity and/or wavelength, it may be recognized that the surface is causing this fluorescence, and the algorithm may flag the measurement for manual check. In some examples, an additional database of materials and/or objects known to fluoresce may be stored. A computer vision algorithm may identify the materials and/or objects observed in the image of the space and compare them to the materials and/or objects in the database. Materials and/or objects that match in the database may then be masked out of the fluorescence image so they do not interfere with bacterial load measurements.

The contamination sensing device 100 may take measurements periodically on a pre-programmed schedule, such as, for example, once per night once lights in a space are off. In some examples, measurements may be taken once each hour. In some examples, measurements may be taken once a day. In some examples, the user of the system may manually initiate a measurement at any time. Manual initiation may be a useful feature in many scenarios including, for example, if an outbreak has occurred in a hospital and certain surfaces need to be checked for surface contamination containing the pathogen. In some examples, new measurements may be used to update a previous contamination map 900. In some examples, the contamination sensing device 100 may be used before and after a surface is disinfected, either through traditional cleaning methods or disinfecting lighting, to determine the performance of the disinfection. In some examples, the contamination sensing device 100 may be integrated with an occupancy sensor(s) to detect the presence of people in the room and initiate measurements when the room is not occupied.

In some examples, a processor receiving data from the contamination sensing device 100 may be able to graph an excitation-emission matrix (EEM). The EEM may show emission spectra as a function of excitation wavelength and create a three dimensional matrix of excitation-emission-intensity points, where, in some examples, the z-axis shows intensity.

In some examples, a projector or other device capable of projecting an image onto a surface may be used in communication with the contamination sensing device 100. A projector may be integrated into the contamination sensing device 100 or mounted separate from the contamination sensing device 100. The projector may be configured to project a contamination map 900 of a measured surface onto the measured surface to visualize the contamination. The projected contamination map 900 may be used, for example, to direct disinfecting efforts onto the surface or to prevent users from touching certain parts of the surface. Projecting the contamination map 900 onto the measured surface may be a beneficial visual technique for showing contamination of surfaces and provoking action be taken (e.g., to disinfect the surface). In some examples, the contamination map 900 may be projected in color. The projection may include a key/legend 902 to allow the users to interpret the contamination map 900. In some examples, the projection may be 3D to show higher concentrations of bacteria of in certain areas. This may be obtained with a 3D or holographic projector and/or multiple projectors. The contamination map 900 shown in FIG. 9 may also show an example of the projection of a contamination map 900 as projected back onto the measured surface 906.

In some examples, computer vision algorithms may be used to increase the readability of the image. In some examples, computer vision algorithms may be used to inform a separate system (e.g., a disinfecting lighting solution) of high risk areas. In some examples, a color filtering or edge detection algorithm may isolate the location of bacteria on surfaces in a captured image. The computer vision algorithms may calculate the real room locations of contamination and send those contamination locations to a disinfecting lighting system 1200. The disinfecting lighting system 1200 may, in response to the contamination locations, increase disinfection power in the space or zone. For example, the disinfecting lighting system 1200 may, in response to the contamination locations, emit light comprising a wavelength in a range of 380 to 420 nm, e.g., 405 nm, that may reduce the presence of contamination such as bacteria. The disinfecting light may be directed to the contamination locations to reduce the contamination present. In some examples, the disinfecting light system 1200 may, in response to the contamination locations, increase the irradiance of the disinfecting light at the contamination locations. The computer vision algorithms may calculate the surface area of a target surface 210 and determine a percentage of the target surface that may be contaminated. This data (e.g., the percentage of the target surface 210 that may be contaminated) may be used to alert staff to the presence of abnormally high bacteria concentrations if the bacteria concentrations are above a threshold (e.g., predetermined threshold).

The data collected by the sensor(s) 104 may include, for example, pixel colors, intensities per wavelength range, and/or SPDs (e.g., intensity per wavelength over a range of wavelengths) for the area that was measured. Pixel color may correspond to a specific wavelength or range of wavelengths. The specific wavelength or range of wavelengths may be used to determine a type of bacteria causing the fluorescence. An intensity may be used to determine a level of bacterial load. The contamination map may show any output including types of bacteria and levels of bacterial load. The contamination may be color coded to show the aforementioned outputs.

Figure 18:
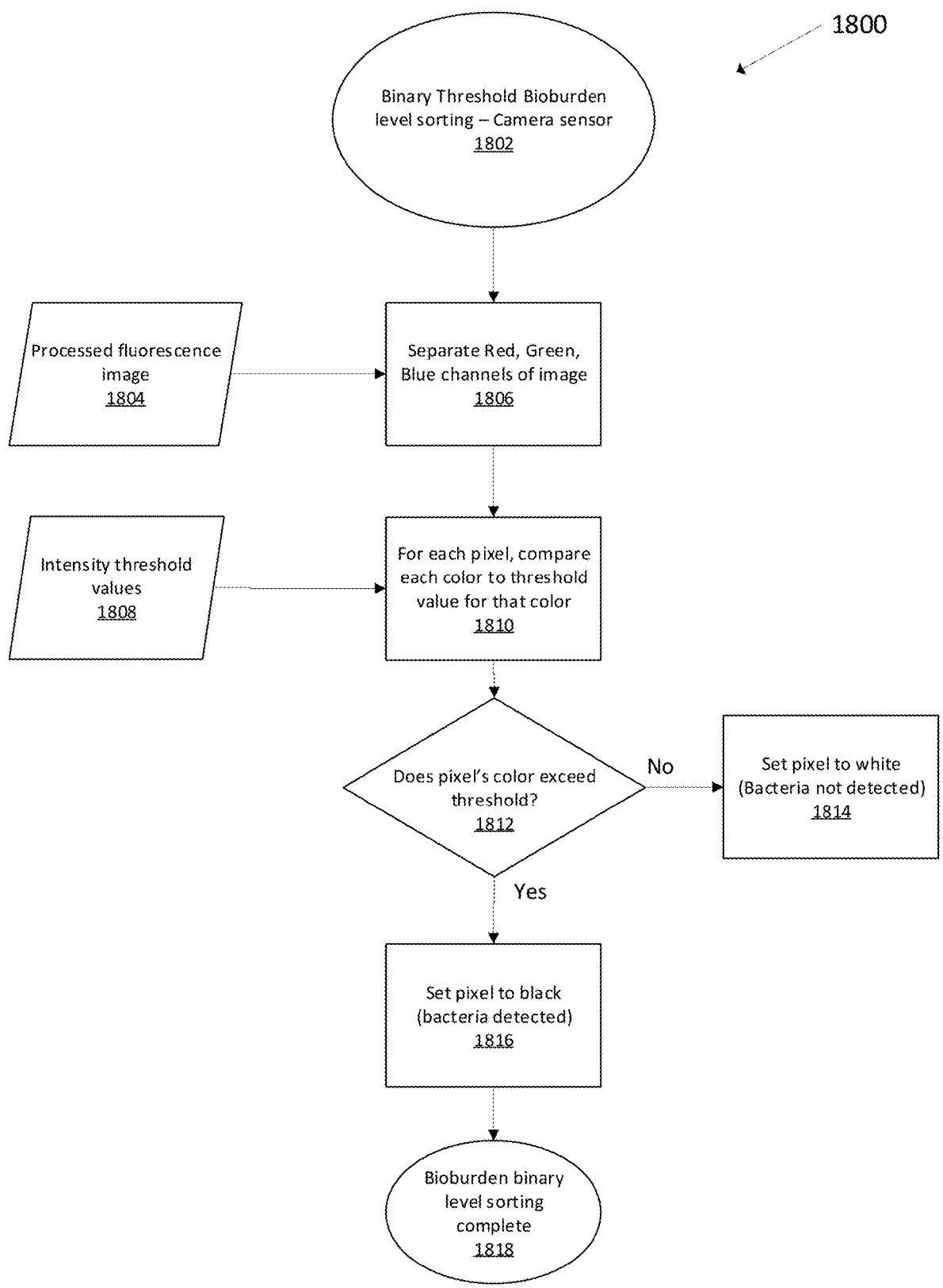
FIG. 18 illustrates a flow chart for binary threshold bioburden level sorting data from a camera.

FIG. 18 is a flowchart showing an example workflow 1800 for binary detection of bacterial load with a camera based sensor. Binary threshold bioburden level sorting may be performed using a camera sensor, beginning at step 1802. A processed fluorescence image 1804 may be separated, using an algorithm, into red, green, and/or blue channels of the image at step 1806. Intensity threshold values 1808 for each pixel of the image may be compared, for each color, to a threshold value for that color at step 1810. The comparing the intensity threshold value 1808 to the threshold value for that color may be repeated for each pixel. It may be determined if each pixel's intensity for the color exceeds the threshold intensity for that color at step 1812. If the pixel's color does not exceed the color threshold (step 1812: NO), the pixel may be set to white at step 1814. Setting a pixel to white may indicate that bacteria was not detected or that detected bacteria was below a threshold. In some examples, colors other than white may be used to indicate that bacteria was not detected. If the pixel's color does exceed the color threshold (step 1812: YES), the pixel may be set to black at step 1816. Setting a pixel to black may indicate that bacteria was detected. In some examples, colors other than black may be used to indicate that bacteria was detected. After completing steps 1810-1816 for each pixel, the bioburden binary level sorting may be complete at step 1818.

Figure 19:
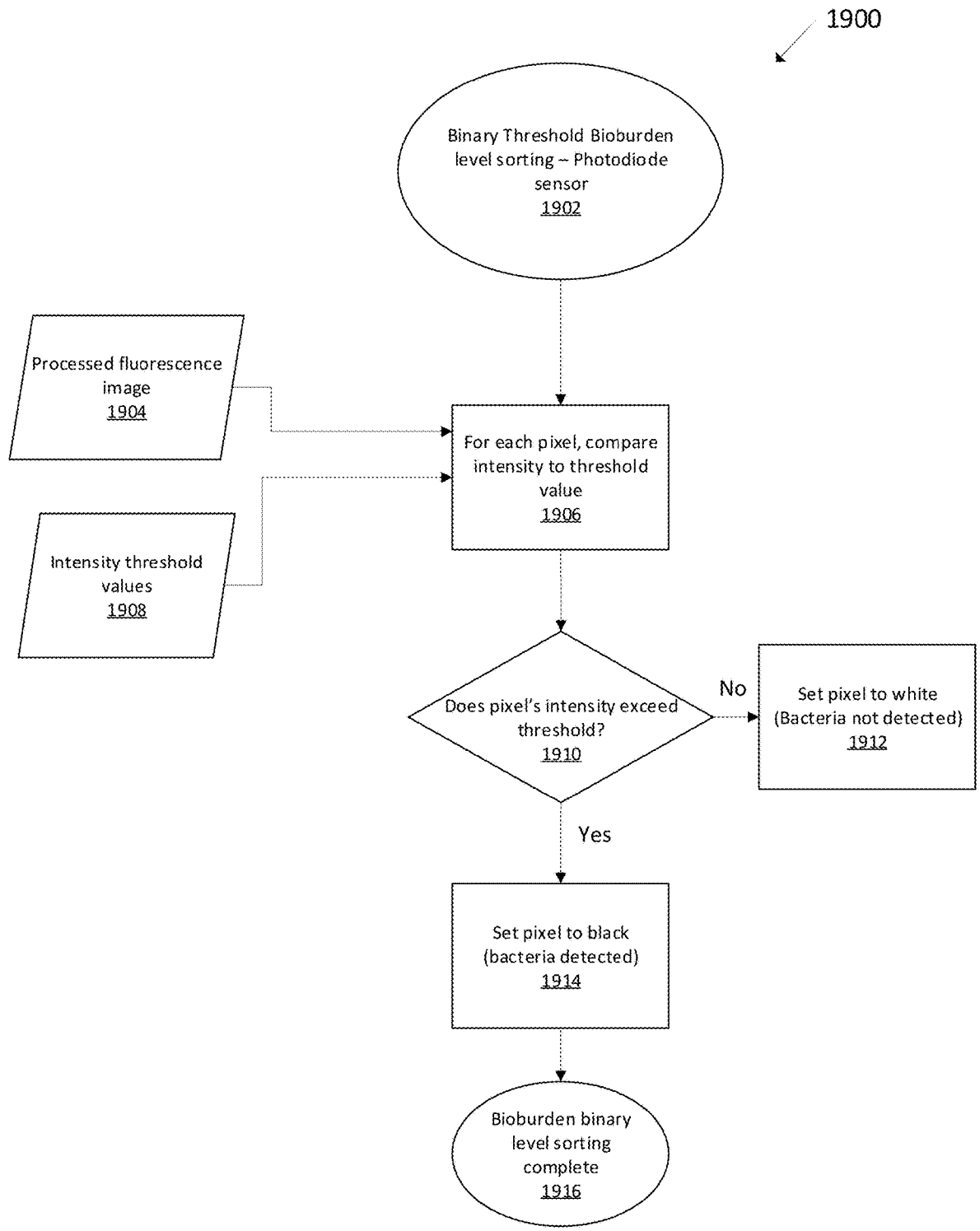
FIG. 19 illustrates a flow chart for binary threshold bioburden level sorting data from a photodiode.

FIG. 19 shows a flowchart showing an example workflow 1900 for binary threshold bioburden level sorting with a photodiode sensor for detecting contamination (e.g., bacteria). Binary threshold bioburden level sorting may be performed using a photodiode sensor beginning at step 1902. Intensity threshold values 1908 and a processed fluorescence image 1904 may be compared to a threshold value at step 1906. The intensity threshold values may indicate the autofluorescence necessary to indicate that a surface is contaminated. The intensity threshold values may be increased/decreased to adjusted adjust the sensitivity of the contamination sensing device 100. The comparing the intensity threshold value to the threshold intensity value 1906 may be repeated for each pixel. It may be determined if each pixel's intensity exceeds the threshold intensity at step 1910. If the pixel's intensity does not exceed the intensity threshold (step 1910: NO), the pixel may be set to white at step 1912. The pixel's intensity not exceeding the intensity threshold at step 1910 indicates that the location corresponding to that pixel is not contaminated. Setting a pixel to white may indicate to a user that bacteria was not detected at the location corresponding to that pixel or that the not enough bacteria was detected to exceed the intensity threshold value 1908. If the pixel's intensity does exceed the intensity threshold (step 1910: YES), the pixel may be set to black at step 1914. Setting a pixel to black may indicate that bacteria was detected (e.g., the level of bacteria represented by that pixel exceeds the amount determined by the intensity threshold value 1908). After completing steps 1906-1914 for each pixel, the bioburden binary level sorting may be complete at step 1916. The bioburden binary level sorting may create an image using the black and white pixels assigned at steps 1910-1914. The image may indicate to a user where contamination (e.g., bacteria) is located. In some examples, the image may indicate to a user to provide disinfection (e.g., manual cleaning, disinfecting light, etc.).

In some examples, there may be a bacterial load threshold. Binary detection may only indicate bacterial load in locations where the bacterial load surpasses the bacterial load threshold. In some examples, there may be a maximum allowed threshold of surface bacterial load. In some examples, a user may be notified if the sensor(s) 104 detects levels above the maximum allowed threshold of surface bacterial load. The user may be notified if the sensor(s) 104 detects levels above the maximum allowed threshold of surface bacterial load, for example, by generating a signal, sending a message to a user device, etc.

Measured bacterial load may be used by the control system 610 to drive decision making of a processor and/or controller. The processor/controller may be able to determine when a surface is considered contaminated based on the measured bacterial load meeting/exceeding a bacterial load threshold. The contamination/bacterial load level at which the surface is considered contaminated may be predetermined by the user or determined by the processor/controller based on measurement trends. The processor/controller may be able to determine what parts of the surface are contaminated. Some levels of bacterial load may be considered safe and/or acceptable and not contaminated. The contamination map key 902 may indicate the bacterial load at which the surface may be considered contaminated. In some examples, the contamination map may only show contaminated areas. In some examples, the contamination map may show both uncontaminated and contaminated levels of bacterial load.

In some examples, data obtained from the contamination sensing device 100 may be used to produce information to display to a user. A contamination map 900 showing the locations and concentration of bacteria may be provided to the user and stored to show changes over time. The contamination map 900 may be provided with a key 902 to help the user interpret it. The contamination map may be color coded to show concentrations/intensities and/or changes in concentrations/intensities of bacteria. The contamination map 900 may be color coded (or other forms of differentiating), to indicate different bins of bacteria detected on the target surface 210. The example device may be able to determine the types of bacteria in bins. This information may be provided to the user.

Figure 20:
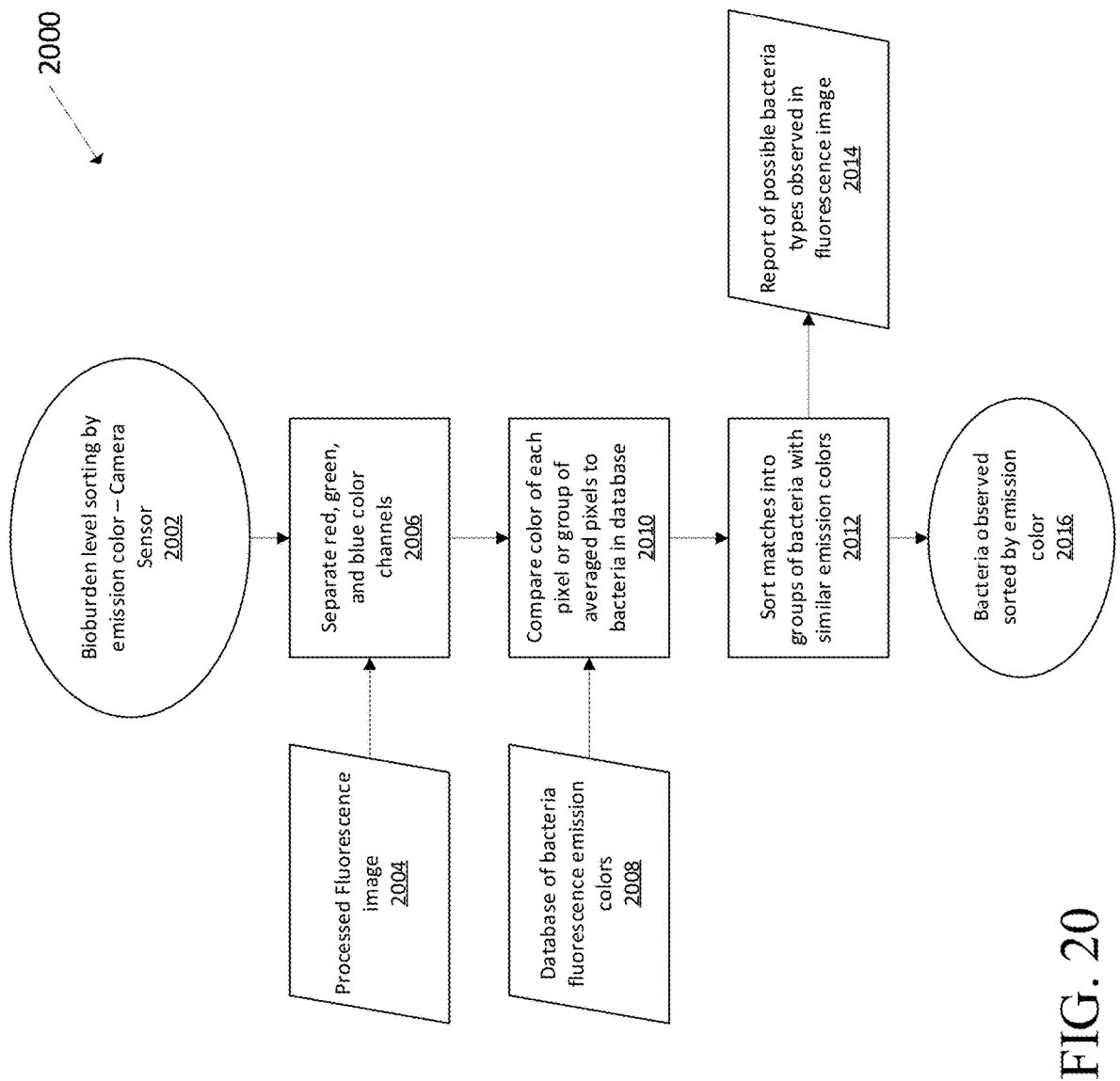
FIG. 20 illustrates a flow chart for bioburden level sorting data from a camera by emission color.

FIG. 20 shows an example bioburden level sorting workflow 2000 in the form of a flow chart for a camera sensor. For example, the sensor(s) 104 may be a camera. A camera may, in some examples, provide more detailed information about autofluorescent light detected than a photodiode sensor. The camera may produce an image containing separate red, green, and blue channels. Binning bacteria by emission color for a camera sensor may be performed, beginning at step 2002. A processed fluorescence image 2004 may be separated, using an algorithm, into red, green, and/or blue channels of the image at step 2006. In some examples, each pixel may be separated into subpixels at step 2006. In some examples, each subpixel may represent red, green, or blue. Each channel may comprise information indicating if contamination is present that autofluoresces at an emission wavelength that corresponds to red, green, or blue.

A database of bacteria fluorescence emission colors may be used to compare the color of each pixel (e.g., subpixel) or group (e.g., set, subset, etc.) of averaged pixels to the bacteria fluorescence emission colors from the database at step 2110. The database of bacteria fluorescence emission colors 2008 may indicate, for example, if a contamination source (e.g., bacteria) autofluoresces at wavelengths that correspond to red, green, and/or blue. The pixels (e.g., subpixels) or group of averaged pixels may be sorted into groups of bacteria with similar emission colors at step 2012. For example, the red, green, and blue colors from the processed fluorescence image 2004 may match a specific bacteria fluorescence emission color from the database 2008. In some examples, a digital filter corresponding to the bacteria fluorescence emission colors from the database 2008 may be used at step 2012 to sort the pixels. The digital filter may, for example, filter out pixels/subpixels that are not associated with the emission of a target bacteria (e.g., contamination) from the database 2008. The digital filter may, for example, allow the contamination sensing device 100 to remove colors/wavelengths that are not associated with autofluorescence from a target contamination source. The matches from comparing at step 2010 may be sorted at step 2012 into groups/sets of bacteria that emit similar emission colors. A report of possible bacteria types observed in the fluorescence image, based on the sorted matches from step 2012, may optionally be output at step 2014. The report output at step 2014 may indicate the bacteria shown by the processed fluorescence image 2004 to match the database of bacteria fluorescence emission colors 2008. The bacteria observed by the camera sensor may be sorted by emission color and completed at step 2016.

Figure 21:
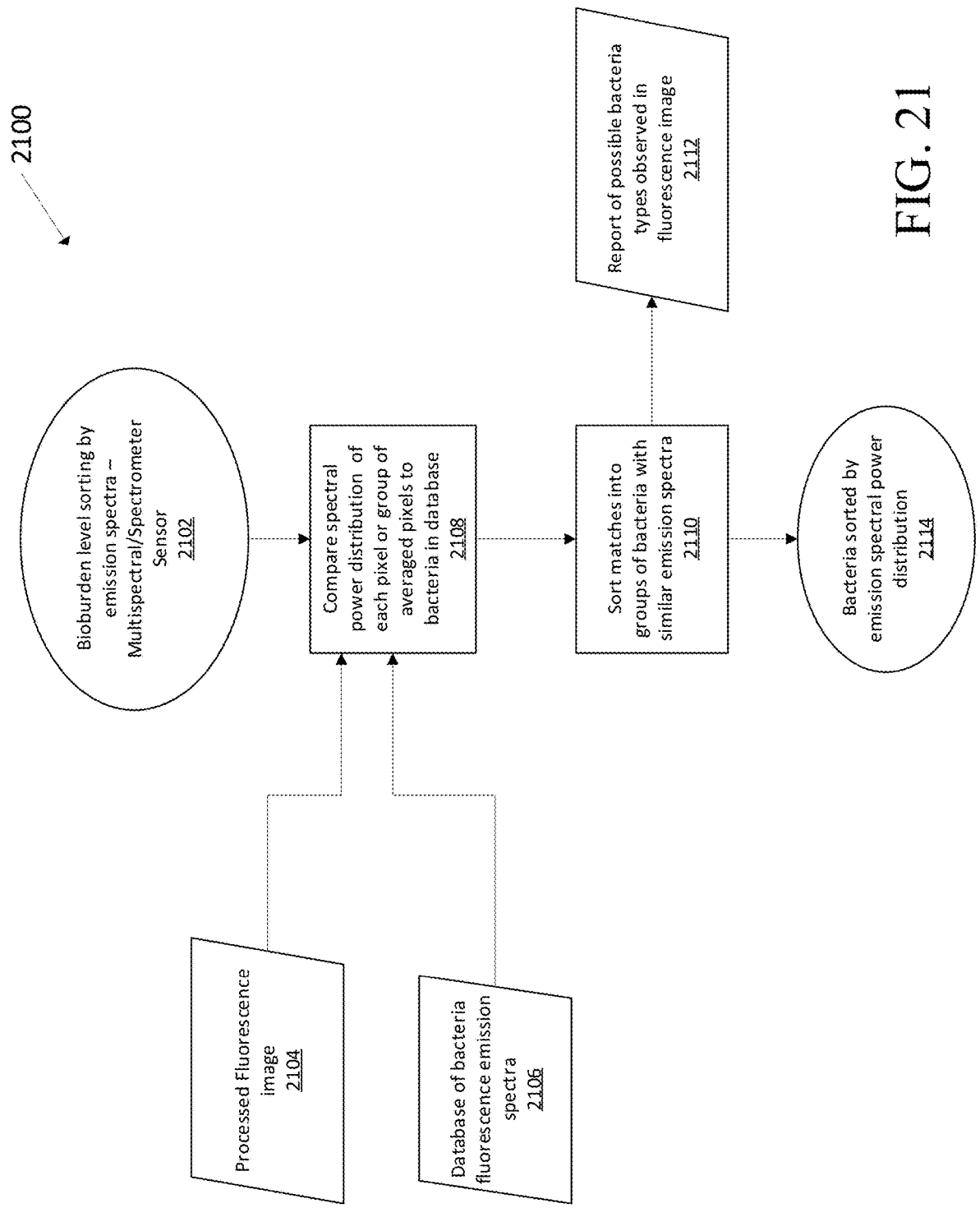
FIG. 21 illustrates a flow chart for bioburden level sorting data from a multispectral/spectrometer sensor by emission spectra.

FIG. 21 shows an example bioburden level sorting workflow 2100 in the form of a flow chart for a multi-spectral/spectrometer based sensor. Multi-spectral/spectrometer based sensor may, for example, provide the entire emission wavelength of a surface measured by the multi-spectra/spectrometer sensors. Multi-spectral/spectrometer sensor may provide the more detailed wavelength information than photodiode sensors or camera sensors. Sorting bacteria by emission color for a multi-spectral/spectrometer sensor may be performed, beginning at step 2102. Each pixel of the processed fluorescence image may comprise an SPD representing the spectrum measured by the multi-spectral/spectrometer sensors. The SPD of each pixel from a processed fluorescence image 2104 may be compared with a database of bacteria fluorescence (e.g., autofluorescence) emission spectra 2106 at step 2108. The database of bacterial fluorescence emission spectra may indicate the emission spectra (e.g., wavelengths) of various contamination sources. The pixels may be sorted into groups/sets of bacteria with similar emission SPDs at step 2110. A report of possible bacteria types observed in the fluorescence image, based on the sorted matches from step 2110, may optionally be output at step 2112. The report output at step 2112 may indicate the bacteria shown by the processed fluorescence image 2104 to match the database of bacteria fluorescence emission spectra 2106. The bacteria observed by the multi-spectra/spectrometer sensor may be sorted by emission spectrum and completed at step 2114.

In some examples, the stored measurements from the contamination sensing device 100 may be used to provide a graph of reduction of bacteria over time. In some examples, the system may be able to monitor the bacterial load of a space over time. This will allow the user to understand changes and trends in bacterial load.

Changes in surface bacterial load may be determined, for example, through a measured change in surface area that the bacteria is contaminating, and/or through the change in intensity of the autofluorescence measured by the sensor(s) 104 (e.g., density/concentration of bacteria) over time. Reduction measurements may be presented as a percent reduction (e.g., 50% reduction) from a predetermined or peak time measurement. In some examples, surface bacterial load may be rated on a number scale. For example, a normal/average measurement may be taken and rated a '5' on a '0-10' scale. Further bacterial load measurements may be compared to this average value. A '7' may indicate higher bacterial load than normal, a '3' may indicate a lower bacterial load than normal. In some examples, a measurement may be taken after the surface is disinfected to determine a realistic minimum for bacterial load (e.g., for comparison).

The example device may be integrated into an internally illuminated surface, such as those described in U.S. application Ser. No. 16/000,426 filed on Jun. 5, 2018, entitled "Devices Using Flexible Light Emitting Layer for Creating Disinfecting Illuminated Surface, and Related Method," which is hereby incorporated by reference herein in its entirety. Such surfaces may be equipped with disinfecting light source(s) interior to the surface such that an outer exterior of the surface is disinfected. The disinfecting light source(s) may emit disinfecting light may comprising a wavelength in a range of 380 to 420 nm, e.g., 405 nm. The disinfecting light may reduce the presence of contamination. The examples disclosed herein may be disposed within an internally illuminated surface and configured to be facing the exterior of the surface. Fluorescence may be measured through the surface so that bacteria located on the exterior of the surface may be detected, measured, and/or characterized. The contamination sensing device 100 may communicate with and/or directly control the internally illuminated surface. The contamination sensing device 100, processor, and/or control system 610 associated with the example device may perform functions comprising turning the disinfecting light source(s) off when a measurement is being taken by the example device and/or adjusting the intensity or color of the emitted light from the disinfecting light source(s).

In some examples, machine learning (e.g., deep learning, neural networks, convolutional neural networks (CNN), etc.) may be used in conjunction with or instead of traditional computer vision algorithms used to isolate fluorescence. A learning model may be used to train the computer to spot bacteria from fluorescence and differentiate from background noise. This may be done through training using labeled reference images or data with known amounts of fluorescence and/or bacteria. The trained model may then be applied to new images to determine bacterial load.

The contamination sensing device 100 may be used in conjunction with current/other methods of determining surface bacterial load, such as bacterial culture tests. The contamination sensing device 100 may direct the user performing the test to the optimal location for taking a surface sample.

In some examples, it may be understood that the physical contamination sensing device 100 and the system in which the contamination sensing device 100 operates may be separate. The physical contamination sensing device 100 may comprise components including the excitation light source(s) 102 and sensor(s) 104 able to detect fluorescence. Additional components of the physical device may include distance sensor(s), occupancy sensor(s), timer(s), projector(s), and/or additional camera(s). The contamination sensing device 100 may include one or multiple housings for these components. These components may be physically coupled or separate. The contamination sensing device 100 may include wired or wireless communication capabilities and a source of power. The system in which the contamination sensing device 100 may operate may include a computer processor able to process the data collected by the contamination sensing device 100. The processor may be able to perform computer vision algorithms for detecting, measuring, and characterizing bacterial load. The system may be able to monitor changes in bacterial load over time. The system may include a user interface (e.g., a computer application) where the processed data from the example device may be accessible by a user. The processed data may include a contamination map 900, levels of bacterial load, binary detection of bacterial load and/or bacterial load, graphs and/or tables of change in bacterial load over time, types of bacteria detected on the surface sorted into bins, etc. The system may include a disinfecting light fixture 700. The disinfecting light fixture 700 may emit disinfecting light may comprising a wavelength in a range of 380 to 420 nm, e.g., 405 nm, and may reduce the presence of contamination such as bacteria. The disinfecting light fixture 700 may emit the disinfecting light, for example, in response to the processed data indicating detected contamination on the surface. The system may include a control system 610 able to make decisions and alter the operations of devices/sensors in the space. The environment in which the example device and system operate may comprise an indoor and/or outdoor space with surfaces. The present disclosure may comprise any of the aforementioned examples.

Figure 22:
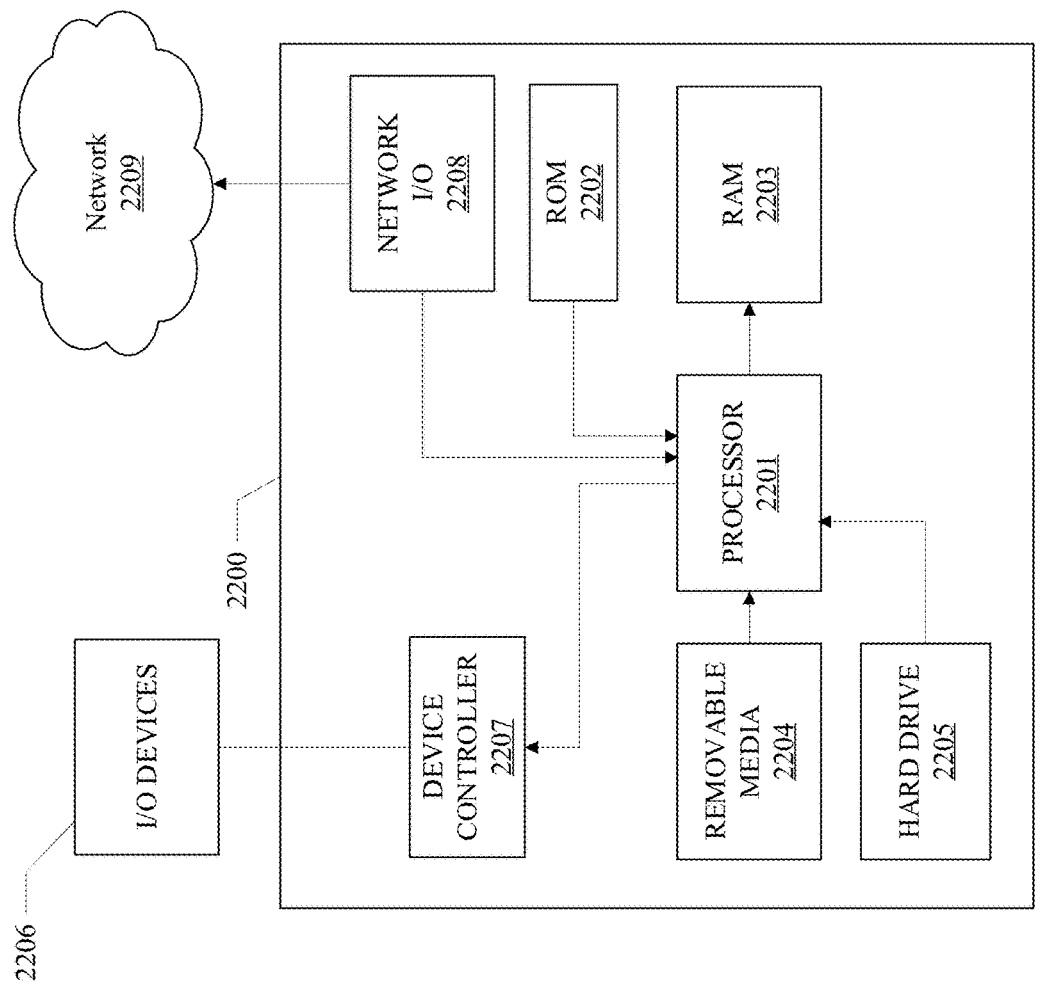
FIG. 22 illustrates an example computing device for implementing the flowcharts of FIGS. 8, 10, and 17-21.

The contamination sensing devices 100 and systems described herein may be implemented via a hardware platform such as, for example, the example computing device 2200 illustrated in FIG. 22. In some examples, the computing device 2200 may implement the flowcharts of FIGS. 8, 10, and 17-21. The contamination sensing devices 100 and systems described herein may be separate components, may comprise separate components, or may be incorporated into a single device. Some elements described with reference to the computing device 2200 may be alternately implemented in software. The computing device 2200 may include one or more processors 2201, which may execute instructions of a computer program to perform any of the features described herein. The instructions may be stored in any type of tangible computer-readable medium or memory, to configure the operation of the processor 2201. As used herein, the term tangible computer-readable storage medium is expressly defined to include storage devices or storage discs and to exclude transmission media and propagating signals. For example, instructions may be stored in a read-only memory (ROM) 2202, random access memory (RAM) 2203, removable media 2204, such as a Universal Serial Bus (USB) drive, compact disk (CD) or digital versatile disk (DVD), floppy disk drive, or any other desired electronic storage medium. Instructions may also be stored in an attached (or internal) hard drive 2205. The computing device 2200 may include one or more input/output devices 2206, such as a display, touch screen, keyboard, mouse, microphone, software user interface, etc. The computing device 2200 may include one or more device controllers 2207 such as a video processor, keyboard controller, etc. The computing device 2200 may also include one or more network interfaces 2208, such as input/output circuits (such as a network card) to communicate with a network such as example network 106. The network interface 2208 may be a wired interface, wireless interface, or a combination thereof. One or more of the elements described above may be removed, rearranged, or supplemented without departing from the scope of the present disclosure.

An example contamination sensing device may comprise a body, a light emitter disposed on the body and configured to emit an excitation wavelength of light toward a surface, a sensor disposed on the body, configured to detect light, and directed toward the surface, and a filter adjuster configured to determine, based on the excitation wavelength of light, a filter configured to remove light outside of an emission wavelength range, wherein the emission wavelength range corresponds to wavelengths of light emitted by contamination upon exposure to the excitation wavelength of light, and adjustably move the filter in front of the sensor.

In some examples, the excitation wavelength is within an excitation range of 230-280 nm, and the emission wavelength range is 330-350 nm.

In some examples, the excitation wavelength is within an excitation range of 385-405 nm, and the emission wavelength range is 430-530 nm.

In some examples, the sensor comprises a camera, photodiode, photodiode array, or multi-spectral sensor.

In some examples, the sensor is configured to detect a distance between the sensor and the surface, the light emitter is configured to adjust, based on the distance between the sensor and the surface, an intensity of the excitation wavelength of light, and the contamination sensing device further comprises a processor configured to determine contamination on the surface, wherein the contamination is determined based on a wavelength of light detected by the sensor, an emission intensity of the light detected by the sensor, and the intensity of the excitation wavelength.

In some examples, the contamination sensing device further comprises a processor configured to determine, based on a database associating excitation spectra and emission spectra of microorganisms or surface materials, the excitation wavelength, determine, based on an emission spectra associated with the determined excitation wavelength, the emission wavelength range, and configure the light emitter to emit the excitation wavelength.

In some examples, the sensor comprises a camera and is further configured to capture an image of the surface, and the contamination sensing device further comprises a processor configured to generate, based on the image and based on the sensor detecting light within the emission wavelength range, a contamination map.

In some examples, the light emitter comprises one of a light emitting diode (LED), an array of LEDs, a laser, an array of lasers, a vertical cavity surface emitting laser (VCSEL), or an array of VCSELs.

In some examples, the contamination sensing device further comprises a processor configured to receive, from the sensor at a first time, a first measurement of light from the surface, receive, from the sensor at a second time, a second measurement of light from the surface, and determine, based on the first measurement and the second measurement, a change in contamination of the surface.

In some examples, the contamination sensing device further comprises a processor configured to determine, based on a target contamination, a digital filter configured to remove light outside a filtered wavelength range, wherein the filtered wavelength range corresponds to wavelengths of light emitted by the target contamination upon exposure to the excitation wavelength, and apply the digital filter to light detected by the sensor.

An example contamination sensing system may comprise a light emitting device configured to emit an excitation wavelength of light toward a surface, a light detecting device, in communication with the light emitting device, comprising a sensor configured to detect light and directed toward the surface, and a filter adjuster configured to determine, based on the excitation wavelength of light, a filter configured to remove light outside of an emission wavelength range, wherein the emission wavelength range corresponds to wavelengths of light emitted by contamination upon exposure to the excitation wavelength of light, and adjustably move the filter in front of the sensor.

In some examples, the excitation wavelength is within an excitation range of 230-280 nm, and the emission wavelength range is 330-350 nm.

In some examples, the excitation wavelength is within an excitation range of 385-405 nm, and the emission wavelength range is 430-530 nm.

In some examples, the contamination sensing system further comprises a processor configured to determine, based on a database associating excitation spectra and emission spectra of microorganisms or surface materials, the excitation wavelength, determine, based on an emission spectra associated with the determined excitation wavelength, the emission wavelength range, and configure the light emitting device to emit the excitation wavelength.

In some examples, the contamination sensing system further comprises a processor configured to receive, from the sensor at a first time, a first measurement of light from the surface, receive, from the sensor at a second time, a second measurement of light from the surface, and determine, based on the first measurement and the second measurement, a change in contamination of the surface.

In some examples, the contamination sensing system further comprises a processor configured to determine, based on a target contamination, a digital filter configured to remove light outside a filtered wavelength range, wherein the filtered wavelength range corresponds to wavelengths of light emitted by the target contamination upon exposure to the excitation wavelength, and apply the digital filter to light detected by the sensor.

An example contamination sensing device may comprise a body, at least one light emitter disposed on the body and configured to emit a light comprising an excitation wavelength toward a surface, and a plurality of sensors disposed on the body and directed toward the surface, wherein each sensor of the plurality of sensors is configured to detect a different emission wavelength corresponding to respective wavelengths of light emitted by contamination upon exposure to the emitted light.

In some examples, the at least one light emitter comprises an array of light emitters, and the light comprises a plurality of different excitation wavelengths of light emitted by the respective emitters of the array of light emitters.

In some examples, the light emitted by the at least one light emitter comprises a plurality of excitation wavelengths.

In some examples, the contamination sensing device further comprises a plurality of filters, wherein each filter is associated with a different sensor of the plurality of sensors, and wherein each sensor of the plurality of sensors is configured to detect the different emission wavelength range based on the associated filter removing light outside of the different emission wavelength ranges.

In some examples, each sensor of the plurality of sensors comprises a camera.

In some examples, the contamination sensing device further comprises a processor configured to determine, based on a target contamination, a digital filter configured to remove light outside a filtered wavelength range, wherein the filtered wavelength range corresponds to wavelengths of light emitted by the target contamination upon exposure to the excitation wavelength, and apply the digital filter to light detected by the sensor 23.

In some examples, wherein the plurality of sensors is a first plurality of sensors, the contamination sensing device further comprises one or more groups of sensors, wherein each group of the one or more groups of sensors comprises at least one first sensor from the first plurality of sensors and at least one second sensor from a second plurality of sensors, and wherein the at least one first sensor and the at least one second sensor detect a same emission wavelength.

The above discussed embodiments are simply examples, and modifications may be made as desired for different implementations. For example, steps and/or components may be subdivided, combined, rearranged, removed, and/or augmented; performed on a single device or a plurality of devices; performed in parallel, in series; or any combination thereof. Additional features may be added.

We claim:
1. A contamination sensing device comprising:
a body;
at least one light emitter disposed on the body and configured to emit a light comprising an excitation wavelength toward a surface; and
a plurality of sensors disposed on the body and directed toward the surface;
wherein each sensor of the plurality of sensors is configured to detect a different emission wavelength range corresponding to respective wavelengths of light emitted by contamination upon exposure to the emitted light, and wherein at least one sensor of the plurality of sensors is configured to detect a concentration level of the contamination, and
wherein at least one sensor of the plurality of sensors comprises a camera and is further configured to capture an image of the surface, the contamination sensing device further comprising one or more processors configured to generate, based on the image and based on the at least one sensor detecting light within an emission wavelength range, and based on the at least one sensor of the plurality of sensors detecting the concentration level of the contamination, a contamination map.

2. The contamination sensing device of claim 1, wherein:
the at least one light emitter comprises an array of light emitters; and
the light comprises a plurality of different excitation wavelengths of light emitted by the respective emitters of the array of light emitters.

3. The contamination sensing device of claim 1, wherein the light emitted by the at least one light emitter comprises a plurality of excitation wavelengths.

4. The contamination sensing device of claim 1, further comprising:
a plurality of filters, wherein each filter is associated with a different sensor of the plurality of sensors, and wherein each sensor of the plurality of sensors is configured to detect the different emission wavelength range based on the associated filter removing light outside of the different emission wavelength range.

5. The contamination sensing device of claim 1, wherein at least one sensor of the plurality of sensors comprises a camera, a photodiode, a photodiode array, or a multi-spectral sensor.

6. The contamination sensing device of claim 1, wherein the one or more processors are further configured to:
determine, based on a target contamination, a digital filter configured to remove light outside a filtered wavelength range, wherein the filtered wavelength range corresponds to wavelengths of light emitted by the target contamination upon exposure to the excitation wavelength; and
apply the digital filter to light detected by at least one sensor of the plurality of sensors.

7. The contamination sensing device of claim 1, wherein the plurality of sensors is a first plurality of sensors, the contamination sensing device further comprising one or more groups of sensors, wherein each group of the one or more groups of sensors comprises at least one first sensor from the first plurality of sensors and at least one second sensor from a second plurality of sensors, and wherein the at least one first sensor and the at least one second sensor detect a same emission wavelength.

8. The contamination sensing device of claim 1, wherein:
the excitation wavelength is within an excitation range of 200-350 nanometers (nm); and
at least one sensor of the plurality of sensors is configured to detect an emission wavelength within an emission wavelength range of 330-350 nm.

9. The contamination sensing device of claim 1, wherein:
the excitation wavelength is within an excitation range of 385-405 nanometers (nm); and
at least one sensor of the plurality of sensors is configured to detect an emission wavelength within an emission wavelength range of 430-530 nm.

10. The contamination sensing device of claim 1, wherein at least one sensor of the plurality of sensors is configured to detect a distance between the at least one sensor and the surface, and wherein the at least one light emitter is configured to adjust, based on the distance between the at least one sensor and the surface, an intensity of the excitation wavelength of the light, wherein the one or more processors are further configured to determine contamination on the surface, wherein the contamination is determined based on:
a wavelength of light detected by the at least one sensor,
an emission intensity of the light detected by the at least one sensor, and
the intensity of the excitation wavelength.

11. The contamination sensing device of claim 1, wherein the one or more processors are further configured to:
determine, based on a database associating excitation spectra and emission spectra of microorganisms or surface materials, the excitation wavelength;
determine, based on an emission spectra associated with the determined excitation wavelength, emission wavelength ranges; and
configure the at least one light emitter to emit the excitation wavelength.

12. The contamination sensing device of claim 1, wherein the at least one light emitter comprises one of a light emitting diode (LED), an array of LEDs, a laser, an array of lasers, a vertical cavity surface emitting laser (VCSEL), or an array of VCSELs.

13. The contamination sensing device of claim 1, wherein the one or more processors are further configured to:
receive, from at least one sensor of the plurality of sensors at a first time, a first measurement of light from the surface;
receive, from the at least one sensor at a second time, a second measurement of light from the surface; and
determine, based on the first measurement and the second measurement, a change in contamination of the surface.

14. The contamination sensing device of claim 1, wherein the one or more processors are further configured to:
receive, from at least one sensor of the plurality of sensors, a measurement of light from the surface; and
determine, based on the measurement, the contamination on the surface.

15. The contamination sensing device of claim 1, wherein the one or more processors are further configured to:
determine, based on a target contamination, a digital filter configured to remove light outside a filtered wavelength range, wherein the filtered wavelength range corresponds to wavelengths of light emitted by the target contamination upon exposure to the excitation wavelength; and
apply the digital filter to light detected by the plurality of sensors.

16. The contamination sensing device of claim 1, wherein the generated contamination map comprises colors indicating the contamination.

17. The contamination sensing device of claim 1, wherein the one or more processors and a disinfecting lighting system are configured to:
turn off the at least one light emitter; determine, from at least one sensor of the plurality of sensors, a contamination on the surface in the dark; and adjust a wavelength of disinfecting light emitted, an irradiance of the disinfecting light emitted, and an amount of time the disinfecting light is emitted from the disinfecting lighting system.

18. A contamination sensing system comprising:
a light emitting device configured to emit a light comprising an excitation wavelength toward a surface; and
a light detecting device, in communication with the light emitting device, comprising a plurality of sensors directed towards the surface, wherein each sensor of the plurality of sensors is configured to detect a different emission wavelength corresponding to respective wavelengths of light emitted by contamination upon exposure to the emitted light, and wherein at least one sensor of the plurality of sensors is configured to detect a concentration level of the contamination, wherein at least one sensor of the plurality of sensors comprises a camera configured to capture an image of the surface, the contamination sensing device further comprising one or more processors configured to generate, based on the image and based on the at least one sensor detecting light within an emission wavelength range, and based on the at least one sensor of the plurality of sensors detecting the concentration level of the contamination, a contamination map.

19. The contamination sensing system of claim 18, wherein at least one sensor of the plurality of sensors comprises a camera, a photodiode, a photodiode array, or a multi-spectral sensor.

20. The contamination sensing system of claim 18, wherein the light emitting device comprises at least one of a light emitting diode (LED), an array of LEDs, a laser, an array of lasers, a vertical cavity surface emitting laser (VCSEL), or an array of VCSELs.

21. The contamination sensing system of claim 18, further comprising:
a plurality of filters, wherein each filter is associated with a different sensor of the plurality of sensors, and wherein each sensor of the plurality of sensors is configured to detect the different emission wavelength range based on the associated filter removing light outside of the different emission wavelength range.

22. The contamination sensing system of claim 18, wherein the one or more processors are further configured to:
determine, based on a target contamination, a digital filter configured to remove light outside a filtered wavelength range, wherein the filtered wavelength range corresponds to wavelengths of light emitted by the target contamination upon exposure to the excitation wavelength; and
apply the digital filter to light detected by at least one sensor of the plurality of sensors.

23. The contamination sensing system of claim 18, wherein:
the excitation wavelength is within an excitation range of 200-350 nanometers (nm) or 385-405 nm;
at least one first sensor of the plurality of sensors is configured to detect an emission wavelength within an emission wavelength range of 330-350 nm; and
at least one second sensor of the plurality of sensors is configured to detect an emission wavelength within an emission wavelength range of 430-530 nm.

24. The contamination sensing system of claim 18, wherein the one or more processors are further configured to:
receive, from at least one sensor of the plurality of sensors, a measurement of light from the surface; and
determine, based on the measurement, the contamination on the surface.

25. The contamination sensing system of claim 18, wherein the one or more processors and a disinfecting lighting system are configured to:
turn off the at least one light emitter; determine, from at least one sensor of the plurality of sensors, a contamination on the surface in the dark; and adjust a wavelength of disinfecting light emitted, an irradiance of the disinfecting light emitted, and an amount of time the disinfecting light is emitted from the disinfecting lighting system.

26. The contamination sensing device of claim 18, wherein the generated contamination map comprises colors indicating the contamination.

* * * * *